United States Patent
Schmidt et al.

(10) Patent No.: US 11,142,571 B2
(45) Date of Patent: *Oct. 12, 2021

(54) IL-6 ANTIBODIES

(71) Applicant: SESEN BIO, INC, Cambridge, MA (US)

(72) Inventors: Michael March Schmidt, Boston, MA (US); Alison Tisdale, Belmont, MA (US); Eric Steven Furfine, Lincoln, MA (US); Grigorios Zarbis-Papastoitsis, Watertown, MA (US)

(73) Assignee: SESEN BIO, INC., Cambridge, MA (US)

( * ) Notice: Subject to any disclaimer, the term of this patent is extended or adjusted under 35 U.S.C. 154(b) by 647 days.

This patent is subject to a terminal disclaimer.

(21) Appl. No.: 15/524,727

(22) PCT Filed: Nov. 6, 2015

(86) PCT No.: PCT/US2015/059532
§ 371 (c)(1),
(2) Date: May 5, 2017

(87) PCT Pub. No.: WO2016/073890
PCT Pub. Date: May 12, 2016

(65) Prior Publication Data
US 2019/0194312 A1    Jun. 27, 2019

Related U.S. Application Data

(60) Provisional application No. 62/077,105, filed on Nov. 7, 2014, provisional application No. 62/087,448, filed on Dec. 4, 2014, provisional application No. 62/247,705, filed on Oct. 28, 2015.

(51) Int. Cl.
| | |
|---|---|
| C07K 16/24 | (2006.01) |
| A61P 27/02 | (2006.01) |
| A61K 39/00 | (2006.01) |
| A61K 9/00 | (2006.01) |
| A61P 3/10 | (2006.01) |
| C07K 16/40 | (2006.01) |

(52) U.S. Cl.
CPC .......... *C07K 16/248* (2013.01); *A61K 9/0048* (2013.01); *A61P 27/02* (2018.01); *A61K 2039/505* (2013.01); *A61P 3/10* (2018.01); *C07K 16/40* (2013.01); *C07K 2317/24* (2013.01); *C07K 2317/33* (2013.01); *C07K 2317/34* (2013.01); *C07K 2317/565* (2013.01); *C07K 2317/71* (2013.01); *C07K 2317/76* (2013.01); *C07K 2317/92* (2013.01); *C07K 2317/94* (2013.01)

(58) Field of Classification Search
CPC .......... A61K 2039/505; A61K 39/3955; A61K 39/395; C07K 16/248; C07K 16/24; A61P 27/02

See application file for complete search history.

(56) References Cited

U.S. PATENT DOCUMENTS

| | | |
|---|---|---|
| 4,548,990 A | 10/1985 | Mueller et al. |
| 4,816,567 A | 3/1989 | Cabilly et al. |
| 5,223,409 A | 6/1993 | Ladner et al. |
| 5,225,539 A | 7/1993 | Winter |
| 5,476,996 A | 12/1995 | Wilson et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,762 A | 12/1997 | Queen et al. |
| 5,698,797 A | 12/1997 | Fontanille et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,839,430 A | 11/1998 | Cama et al. |
| 5,870,926 A | 2/1999 | Saito et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,180,370 B1 | 1/2001 | Queen et al. |
| 6,277,375 B1 | 8/2001 | Ward et al. |
| 6,358,058 B1 | 3/2002 | Strupat et al. |
| 7,820,155 B2 | 10/2010 | Way |
| 8,536,308 B2 | 9/2013 | Way et al. |
| 8,657,211 B2 | 2/2014 | Ueda et al. |
| 8,802,820 B2 | 8/2014 | Chamberlain et al. |
| 9,951,130 B2 * | 4/2018 | Schmidt .................. A61P 7/10 |

(Continued)

FOREIGN PATENT DOCUMENTS

| | | |
|---|---|---|
| CN | 101346395 | 1/2009 |
| CN | 102224169 | 10/2011 |

(Continued)

OTHER PUBLICATIONS

Fischer et al. The two faces of IL-6 in the tumor microenvironment. Semin Immunol. Feb. 2014; 26(1): 38-47 (Year: 2014).*

(Continued)

*Primary Examiner* — Vanessa L. Ford
*Assistant Examiner* — Sandra E Dillahunt
(74) *Attorney, Agent, or Firm* — McDonnell Boehnen Hulbert & Berghoff LLP

(57) ABSTRACT

Improved IL-6 antibodies are provided. Uses of the antibodies in the treatment of IL-6-related diseases, e.g., ocular diseases such as diabetic macular edema, are disclosed.

35 Claims, 25 Drawing Sheets
Specification includes a Sequence Listing.

(56) References Cited

U.S. PATENT DOCUMENTS

| | | |
|---|---|---|
| 2003/0082630 A1 | 5/2003 | Kolkman et al. |
| 2003/0138417 A1 | 7/2003 | Kaisheva et al. |
| 2003/0157561 A1 | 8/2003 | Kolkman et al. |
| 2004/0009222 A1 | 1/2004 | Chou et al. |
| 2007/0269868 A1 | 11/2007 | Carvalho Jensen et al. |
| 2009/0130114 A1 | 5/2009 | Qian et al. |
| 2009/0202526 A1 | 8/2009 | Pons |
| 2009/0226530 A1 | 9/2009 | Lassner et al. |
| 2010/0034809 A1 | 2/2010 | Diefenbach-Streiber et al. |
| 2010/0187601 A1 | 7/2010 | Masuoka et al. |
| 2011/0045025 A1 | 2/2011 | Middaugh et al. |
| 2011/0171241 A1 | 7/2011 | Dix et al. |
| 2012/0005773 A1 | 1/2012 | Aasen et al. |
| 2012/0034212 A1 | 2/2012 | Bowen et al. |
| 2012/0121594 A1 | 5/2012 | Smith |
| 2014/0017244 A1 | 1/2014 | Duerr et al. |
| 2015/0017163 A1 | 1/2015 | Patel et al. |
| 2015/0125468 A1 | 5/2015 | Schmidt et al. |
| 2015/0239970 A1 | 8/2015 | Bee et al. |

FOREIGN PATENT DOCUMENTS

| | | | |
|---|---|---|---|
| WO | 199117271 | 11/1991 | |
| WO | 199201047 | 1/1992 | |
| WO | 199203918 | 3/1992 | |
| WO | 199209690 | 6/1992 | |
| WO | 199215679 | 9/1992 | |
| WO | 199218619 | 10/1992 | |
| WO | 199220791 | 11/1992 | |
| WO | 199301288 | 1/1993 | |
| WO | 199306213 | 4/1993 | |
| WO | 199311161 | 6/1993 | |
| WO | 199312227 | 6/1993 | |
| WO | 199413804 | 6/1994 | |
| WO | 199425585 | 11/1994 | |
| WO | 199627011 | 9/1996 | |
| WO | 199703461 | 1/1997 | |
| WO | 199713852 | 4/1997 | |
| WO | 199823289 | 6/1998 | |
| WO | 199824884 | 6/1998 | |
| WO | 199850431 | 11/1998 | |
| WO | 199945962 | 9/1999 | |
| WO | 200034784 | 6/2000 | |
| WO | 200114424 | 3/2001 | |
| WO | 200243478 | 6/2002 | |
| WO | 2004045507 | 6/2004 | |
| WO | WO 2005062955 | 7/2005 | |
| WO | 2006028936 | 3/2006 | |
| WO | 2007076927 | 7/2007 | |
| WO | 2007104529 | 9/2007 | |
| WO | 2006020114 | 4/2008 | |
| WO | 2008144763 | 11/2008 | |
| WO | 2010/060768 | 6/2010 | |
| WO | WO 2012007896 | 1/2012 | |
| WO | 2014074905 | 5/2014 | |
| WO | WO-2014074905 A1 * | 5/2014 | ............ A61P 9/10 |
| WO | WO 2016073894 | 5/2016 | |

OTHER PUBLICATIONS

Hume et al. A Protective Role for IL-6 in Staphylococcal Microbial Keratitis. Investigative Ophthalmology & Visual Science, Nov. 2006, vol. 47, No. 11 (Year: 2006).*
Agarwal et al., "Rodent Models of Experimental Autoimmune Uveitis," Methods in Mol Biol, 2012, pp. 443-469, vol. 300.
Altschul et al., "Basic Local Alignment Search Tool," J. Mol. Biol., 1990, pp. 403-410, vol. 215.
Altschul et al., "Gapped BLAST and PSI-BLAST: a new generation of protein database search programs," Nucleic Acids Research, 1997, pp. 3389-3402, vol. 25, No. 17.
Asquith et al., "Animal models of Rheumatiod Arthritis," Euro. J. Immunol., 2009, pp. 2040-2044, vol. 39.
Barbas et al., "Assembly of combinatorial antibody libraries on phage surfaces: The gene III site," PNAS USA, 1991, pp. 7978-7982, vol. 88.
Boder et al., "Directed evolution of antibody fragments with monovalent femtomolar antigen-binding affinity," PNAS USA, 2000, pp. 10701-10705, vol. 97.
Brown et al., "Tolerance to Single, but Not Multiple, Amino Acid Replacements in Antibody Vh CDR2," J. Immunol., 1996, pp. 3285-3291, vol. 156.
Caspi et al., "Understanding Autoimmune Uveitis through Animal Models," Investigative Opthamology Visual Science, 2011, pp. 1873-1879, vol. 52, No. 3.
Chao et al., "Isolating and engineering human antibodies using yeast surface display," Nature Protocols, 2006, pp. 755-768, No. 1.
Chien et al., "Significant structural and functional change of an antigen-binding site by a distant amino acid substitution: Proposal of a structural mechanism," Proceedings of the National Academy of Sciences, 1989, pp. 5532-5536, vol. 86.
Chothia et al, "Canonical Structures for the Hypervariable Regions of Immunoglobulins," J. Mol. Biol., 1987, pp. 901-917, vol. 196.
Chothia et al, "Conformations of immunoglobulin hypervariable regions," Nature, 1989, pp. 878-883, vol. 342.
Einmahl et al., "Therapeutic applications of viscous and injectable poly(ortho esters)," Advanced Drug Delivery reviews, 2001, pp. 45-73, vol. 53.
Finch et al., "Whole-Molecule Antibody Engineering: Generation of a High-Affinity Anti-IL-6 Antibody with Extended Pharmacokinetics," Journal of Molecular Biology, 2011, pp. 791-807, vol. 411.
Funatsu, et al "Vitreous levels of interleukin-6 and vascular endothelial growth factor are related to diabetic macular adema," Ophthalmology, 2003, pp. 1690-1696, vol. 110, No. 9.
Ghelardi et al., "A Mucoadhesive Polymer Extracted from Tamarind Seed Improves the Intraocular Penetration and Efficacy of Rufloxacin in Topical Treatment of Experimental Bacterial Keratitis," Antimicrobial Agents and Thermotherapy, 2004, pp. 3396-3401, vol. 48, No. 9.
Gram et al., "In vitro selection and affinity maturation of antibodies from a naive combinatorial immunoglobulin library," PNAS USA, 1992, pp. 3576-3580, vol. 89.
Griffiths et al., "Human anti-self antibodies with high specificity from phage display libraries," The EMBO Journal, 1993, pp. 725-734, vol. 12, No. 2.
Haruta et al., "Blockade of Interleukin-6 Signaling Suppresses Not Only Th17 but Also Interphotoreceptor Retinoid Binding Protein-Specific Th1 by Promoting Regulatory T Cells in Experimental Autoimmune Uveoretinitis," Invest. Opthal. Vis. Sci., 2011, pp. 3264-3271, vol. 52, No. 6.
Hawkins et al., "Selection of phage antibodies by binding affinity: Mimicking affinity maturation," Journal of Molecular Thology, 1992, pp. 889-896, vol. 226, No. 3.
Hoogenboom et al. "Multi-subunit proteins on the surface of filamentour phage: methodologies for displaying antibody (Fab) heavy and light chains," Nucl. Acids. Res., 1991, pp. 4133-4137, vol. 19, No. 15.
Huse, et al., "Generation of a Large Combinatorial Library of the Immunoglobulin Repertoire in Phage Lambda," Science, 1989, pp. 1275-1281, vol. 246.
Izumi-Nagai et al., "Interleukin-6 Receptor-Mediated Activation of Signal Transducer and Activator of Transcription-3 (STAT3) Promotes Choroidal Neovascularization," American Journal of Pathology, 2007, pp. 2149-2158, vol. 170, No. 6.
Kalai et al., "Analysis of the mechanism of action of anti-human interleukin-6 and anti-human interleukin-6 receptor-neutralising monoclonal antibodies," Eur. J. Biochem., 1997, pp. 690-700, vol. 249.
Kauffmann et al., "Cytokines in Vitreous Humor: Interleukin-6 is Elevated in Proliferative Vitreoretinopathy," Invest Opthalmol Vis Sci., 1994, pp. 900-906, vol. 35, No. 3.
Kohler et al, "Continuous cultures of fused cells secreting antibody of predefined specificity," Nature, 1975, pp. 495-497, vol. 256.
Krzystolik et al., "Prevention of Experimental Choroidal Neovascularization with Intravitreal Anti-Vascular Endothelial Growth Factor Antibody Fragment," Arch Ophthalmol, 2002, 338-346, vol. 120.

(56) References Cited

OTHER PUBLICATIONS

Lissilaa, Rami et al. "Although IL-6 Trans-Signaling Is Sufficient to Drive Local Immune Responses, Classical IL-6 Signaling Is Obligate for the Induction of T Cell-Mediated Autoimmunity", J. Immunol., 2010, 185 (9) 5512-5521.
Brown, et al, "Tolerance of single, but not multiple, amino acid replacements in antibody VH CDR 2: a means of minimizing B cell wastage from somatic hypermutation?", J Immunol., 156(9):3285-91 (1998).
Tultseva S.N. et al., "The role of inflammation in the pathogenesis of post-thrombotic macular edema", Modem directions of drug treatment, Ophthalmological statements, 2012, vol. 5 (see pp. 37-40).
Lacroix, Marine et al. "Novel Insights into Interleukin 6 (IL-6) Cis- and Transsignaling Pathways by Differentially Manipulating the Assembly of the IL-6 Signaling Complex", J. Biol. Chem., Nov. 6, 2015;290(45):26943-53.
Rose-John, Stefan et al. "IL-6 Trans-Signaling via the Soluble IL-6 Receptor: Importance for the Pro-Inflammatory Activities of IL-6", International Journal of Biological Sciences, 2012;8(9):1237-1247.
Magdelaine-Beuzelin, et al., "Therapeutic antibodies in ophthalmology: Old is new again", mAbs, 2:176-180 (2010).
Martin et al., "Crystal Structure at 2.8 A of an FcRn/Heterodimeric Fc Complex: Mechanism of pH-Dependent Binding," Molecular Cell, 2001, pp. 867-877, vol. 7.
Miao et al., "Inflammatory cytokines in aqueous humor of patients with choroidal neovascularization," Molecular Vision, 2012, pp. 574-580, vol. 18.
Noma et al., "Aqueous humour levels of cytokines are correlated to vitreous levels and severity of macular oedema in branch retinal vein occlusion," Eye, 2008, pp. 42-48, vol. 22.
Pearson, William R., "Effective protein sequence comparison," Methods of Enzymology, 1996, pp. 227-268, vol. 266.
Pearson, William R., "Empirical statistical estimates for sequence similarity searches," Journal of Molecular Biology, 1998, pp. 71-84, vol. 276, No. 1.
Pearson, William R., "Rapid and Sensitive Sequence Comparison with FASTP and FASTA," Methods Enzymol, 1990, pp. 63-98, vol. 183.
Rudikoff et al., "Single amino acid substitution altering antigen-binding specificity,", Proceedings of the National Academy of Sciences, 1982, pp. 1979-1983, vol. 79.
Tomizuka et al., "Double trans-chromosomic mice: Maintenance of two individual human chromosome fragments aontaining Ig heavy and k loci and expression of fully human antibodies," PNAS USA, 2000, pp. 722-727, vol. 97.
Vajdos et al., "Comprehensive Functional Maps of the Antigenbinding Site of an Anti-ErbB2 Antibody Obtained with Shotgun Scanning Mutagenesis," J. Mol. Biol., 2002, pp. 415-528, vol. 320, No. 2.
Winkler et al., "Changing the antigen binding specificity by single point mutations of an anti-p24 (HIV-1) antibody," The Journal of Immunology, 2000, pp. 4505-4514, vol. 165.
Yoshimura et al., "Involvement of Th17 cells and the effect of anti-IL-6 therapy in autoimmune uveitis," Rheum., 2009, pp. 347-354, vol. 48.
Yuuki et al, "Inflammatory cytokines in vitreous fluid and serum of patients with diabetic vitreoretinopathy," Journal of Diabetes and its Complications, 2001, pp. 257-259, vol. 15, No. 5.
Dillon et al., "Structural and functional characterization of disulfide isoforms of the human IgG2 subclass," J Biol Chem. 283(23):16206-15 (2008).
International Search Report for PCT/US2013/069279, dated Mar. 7, 2014.
Murray et al., Biokhimiya cheloveka, «Mir», LANGE Medical book 1993, v.1, p. 34.
Padlan et al., "Identification of specificity-determining residues in antibodies," FASEB J, 9:133-139 (1995).
Tamura et al., "Structural correlates of an anticarcinoma antibody: identification of specificity-determining residues (SDRs) and development of a minimally immunogenic antibody variant by retention of SDRs only," J Immunol., 164:1432-1441 (2000).
Tenhumberg, et al. "Structure-guided Optimization of the Interleukin-6 Trans-signaling Antagonist," Journal of Biological Chemistry, 283:27200-27207 (2008).
Wilson et al., "Assessing annotation transfer for genomics: quantifying the relations between protein sequence, structure and function through traditional and probabilistic scores," JMol Biol. (2000) 297, 233-249.
Casset et al., "A peptide mimetic of an anti-CD4 monoclonal antibody by rational design," Biochemical and Biophysical Research Communications, 307: 198-205 (2003).
Chang, B.S. and Hershenson, S. Practical approaches to protein formulation development in "Rationale Design of stable protein formulations-theory and practice" (J.F. Carpenter and M.C. Manning eds.) Kluwer Academic/Plenum publishers, New York.pp. 1-25) (2002).
Colman, "Effects of amino acid sequence changes on antibody-antigen interactions," Research in Immunology, 145:33-36 (1994).
Maccallum et al., "Antibody-antigen interactions: contact analysis and binding site topography," Journal of Molecular Biology, 262:732-745, 1996 (1996).
Paul, Fundamental Immunology, 3rd Edition, Raven Press, New York, Chapter 8, pp. 292-295 (1993).
Abaza et al., "Effects of amino acid substitutions outside an antigenic site on protein binding to monocloncal antibodies of predetermined specificity obtained by peptide immunization: demonstration with region 94-100 (antigenic site 3) of myoglobin," J. Prat. Chem., 11 :433-444 (1992).
McGuinness et al., "Class 1 outer membrane protein of Neisseria meningitidis: epitope analysis of the antigenic diversity between strains, implications for subtype definition and molecular epidemiology," Mol. Microbiol., 7:505-514 (1993).
Moudallal et al., "Monoclonal antibodies as probes of the antigenic structure of tobacco mosaic virus," EMBO Journal 1: 1005-1010 (1982).
Panka, David J et al. "Defining the structural correlates responsible for loss or arsonate affinity in an IDCR antibody isolated from an autoimmune mouse" Mol Immunol., 30(11):1013-20 (1993).

* cited by examiner

```
              FR1            CDR1       FR2       CDR2      FR3
         <--------------><----------><--------><--------><-------->
              10        20        30        40        50        60        70
         ....|....|....|....|....|....|....|....|....|....|....|....|....|....|
EBI-029  QVQLVQSGAEVKKPGSSVKVSCKASGYALSNYLIEWVRQAPGQGLEWMGVITPGSGTINYAQKFQGRVTI
EBI-030  QVQLVQSGAEVKKPGSSVKVSCKASGYVLPNYLIEWVRQAPGQGLEWMGVTTPGGGTINYAQKFQGRVTI
EBI-031  QVQLVQSGAEVKKPGSSVKVSCKASGYVLPNYLIEWVRQAPGQGLEWMGVTTPGGGTINYAQKFQGRVTI
              FR3             CDR3      FR4         CH1
         <--------------><----------><--------><-------------->
              80        90       100       110       120       130       140
         ....|....|....|....|....|....|....|....|....|....|....|....|....|....|
EBI-029  TADESTSTAYMELSSLRSEDTAVYYCARSRWDPLYYYALEYWGQGTTVTVSSASTKGPSVFPLAPCSRST
EBI-030  TADESTSTAYMELSSLRSEDTAVYYCARSRWDPLYYYALEYWGQGTTVTVSSASTKGPSVFPLAPCSRST
EBI-031  TADESTSTAYMELSSLRSEDTAVYYCARSRWDPLYYYALEYWGQGTTVTVSSASTKGPSVFPLAPCSRST
                                        CH1
         <-------------------------------------------------------------------->
              150       160       170       180       190       200       210
         ....|....|....|....|....|....|....|....|....|....|....|....|....|....|
EBI-029  SESTAALGCLVKDYFPEPVTVSWNSGALTSGVHTFPAVLQSSGLYSLSSVVTVPSSNFGTQTYTCNVDHK
EBI-030  SESTAALGCLVKDYFPEPVTVSWNSGALTSGVHTFPAVLQSSGLYSLSSVVTVPSSNFGTQTYTCNVDHK
EBI-031  SESTAALGCLVKDYFPEPVTVSWNSGALTSGVHTFPAVLQSSGLYSLSSVVTVPSSNFGTQTYTCNVDHK
           CH1      Hinge                      CH2
         <-----><---------><-------------------------------------------------->
              220       230       240       250       260       270       280
         ....|....|....|....|....|....|....|....|....|....|....|....|....|....|
EBI-029  PSNTKVDKTVERKCCVECPPCPAPPVAGPSVFLFPPKPKDTLMISRTPEVTCVVVDVSHEDPEVQFNWYV
EBI-030  PSNTKVDKTVERKCCVECPPCPAPPVAGPSVFLFPPKPKDTLMISRTPEVTCVVVDVSHEDPEVQFNWYV
EBI-031  PSNTKVDKTVERKCCVECPPCPAPPVAGPSVFLFPPKPKDTLMISRTPEVTCVVVDVSHEDPEVQFNWYV
                                      CH2                               CH3
         <----------------------------------------------------------><-------->
              290       300       310       320       330       340       350
         ....|....|....|....|....|....|....|....|....|....|....|....|....|....|
EBI-029  DGVEVHNAKTKPREEQFNSTFRVVSVLTVVHQDWLNGKEYKCKVSNKGLPAPIEKTISKTKGQPREPQVY
EBI-030  DGVEVHNAKTKPREEQFNSTFRVVSVLTVVHQDWLNGKEYKCKVSNKGLPAPIEKTISKTKGQPREPQVY
EBI-031  DGVEVHNAKTKPREEQFNSTFRVVSVLTVVAQDWLNGKEYKCKVSNKGLPAPIEKTISKTKGQPREPQVY
                                        CH3
         <-------------------------------------------------------------------->
              360       370       380       390       400       410       420
         ....|....|....|....|....|....|....|....|....|....|....|....|....|....|
EBI-029  TLPPSREEMTKNQVSLTCLVKGFYPSDIAVEWESNGQPENNYKTTPPMLDSDGSFFLYSKLTVDKSRWQQ
EBI-030  TLPPSREEMTKNQVSLTCLVKGFYPSDIAVEWESNGQPENNYKTTPPMLDSDGSFFLYSKLTVDKSRWQQ
EBI-031  TLPPSREEMTKNQVSLTCLVKGFYPSDIAVEWESNGQPENNYKTTPPMLDSDGSFFLYSKLTVDKSRWQQ
              CH3
         <------------>
              430       440
         ....|....|....|....|....|...
EBI-029  GNVFSCSVMHEALHNHYTQKSLSLSPGK
EBI-030  GNVFSCSVMHEALHNHYTQKSLSLSPGK
EBI-031  GNVFSCSVMHEALHNHYTQKSLSLSPGK
```

Fig. 15A

SEQUENCE LISTING

<160> NUMBER OF SEQ ID NOS: 54

<210> SEQ ID NO 1
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Val Glu Pro Lys Ser
        210                 215                 220

Cys
225

<210> SEQ ID NO 2
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 3
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Ala Leu Ser Asn Tyr Leu Ile Glu
1               5                   10
```

```
<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Val Ile Thr Pro Gly Ser Gly Thr Ile Asn
1               5                   10

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ser Arg Trp Asp Pro Leu Tyr Tyr Tyr Ala Leu Glu Tyr
1               5                   10

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ala Ser Glu Ser Val Asp Asn Tyr Gly Ile Pro Phe Met Asn
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Ala Ser Asn Arg Gly Ser
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Gln Ser Glu Glu Val Pro Leu Thr
1               5

<210> SEQ ID NO 10
<211> LENGTH: 448
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 10
```

| | | | | | | | | | | | | | | | |
|---|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ser|
|1| | | |5| | | | |10| | | | |15| |

| | | | | | | | | | | | |
|---|---|---|---|---|---|---|---|---|---|---|---|
|Ser|Val|Lys|Val|Ser|Cys|Lys|Ala|Ser|Gly|Tyr|Ala|Leu|Ser|Asn|Tyr|
| | | |20| | | | |25| | | | |30| | |

Leu Ile Glu Trp Val Arg Gln Ala Pro Gly Gln Gly Leu Glu Trp Met
         35                  40                  45

Gly Val Ile Thr Pro Gly Ser Gly Thr Ile Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Trp Asp Pro Leu Tyr Tyr Ala Leu Glu Tyr Trp
             100                 105                 110

Gly Gln Gly Thr Thr Val Thr Val Ser Ser Ala Ser Thr Lys Gly Pro
             115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Asn Phe Gly Thr Gln Thr Tyr Thr Cys Asn Val Asp
             195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser His Glu Asp Pro
             260                 265                 270

Glu Val Gln Phe Asn Trp Tyr Val Asp Gly Val Glu Val His Asn Ala
             275                 280                 285

Lys Thr Lys Pro Arg Glu Glu Gln Phe Asn Ser Thr Phe Arg Val Val
             290                 295                 300

Ser Val Leu Thr Val Val Ala Gln Asp Trp Leu Asn Gly Lys Glu Tyr
305                 310                 315                 320

Lys Cys Lys Val Ser Asn Lys Gly Leu Pro Ala Pro Ile Glu Lys Thr
                 325                 330                 335

Ile Ser Lys Thr Lys Gly Gln Pro Arg Glu Pro Gln Val Tyr Thr Leu
             340                 345                 350

Pro Pro Ser Arg Glu Glu Met Thr Lys Asn Gln Val Ser Leu Thr Cys
             355                 360                 365

Leu Val Lys Gly Phe Tyr Pro Ser Asp Ile Ala Val Glu Trp Glu Ser
             370                 375                 380

```
Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 11
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285
```

-continued

```
Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 12
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 13
<211> LENGTH: 122
<212> TYPE: PRT
<213> ORGANISM: Mus sp.

<400> SEQUENCE: 13

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Arg Pro Gly Gln Gly Leu Glu Trp Ile
        35                  40                  45

Gly Val Ile Thr Pro Gly Ser Gly Thr Ile Asn Tyr Asn Glu Lys Phe
    50                  55                  60

Lys Gly Lys Ala Val Leu Thr Ala Asp Lys Ser Ser Ser Thr Val Tyr
65                  70                  75                  80

Met Gln Leu Ser Ser Leu Thr Ser Asp Asp Ser Ala Val Tyr Phe Cys
                85                  90                  95

Ala Lys Ser Arg Trp Asp Pro Leu Tyr Tyr Tyr Ala Leu Glu Tyr Trp
            100                 105                 110

Gly Gln Gly Thr Ser Val Thr Val Ser Ser
        115                 120

<210> SEQ ID NO 14
<211> LENGTH: 111
<212> TYPE: PRT
<213> ORGANISM: Mus sp.

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Leu Thr Phe Gly Ala Gly Thr Lys Leu Glu Leu Lys
            100                 105                 110

<210> SEQ ID NO 15
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser
            115                 120

<210> SEQ ID NO 16
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Arg Ala Ser Gly Ser Val Asp Asn Tyr
            20                  25                  30

Gly Ile Ser Phe Met Asn Trp Tyr Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Leu Thr Phe Gly Gln Gly Thr Lys Leu Glu Ile Lys
            100                 105                 110

<210> SEQ ID NO 17
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
                100                 105                 110

Gly Gln Gly Thr Thr Val Thr Val Ser Ser
            115                 120

<210> SEQ ID NO 18
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
                20                  25                  30

Gly Ile Pro Phe Met Asn Trp Tyr Gln Gln Lys Pro Gly Gln Pro Pro
            35                  40                  45

Lys Leu Leu Ile Tyr Ala Ala Ser Asn Arg Gly Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
                100                 105                 110

Thr Val

<210> SEQ ID NO 19
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
                20                  25                  30

Leu Ile Glu Trp Val Arg Gln Ala Pro Gly Gln Gly Leu Glu Trp Met
            35                  40                  45

Gly Val Ile Thr Pro Gly Ser Gly Thr Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 20
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 20

```
caagtgcagc tggtgcagtc aggggccgag gttaagaagc cagggagcag cgtcaaggta      60
tcttgtaaag cgtctggtta cgcccttca  aactacctga tcgaatgggt gaggcaggct     120
cccggccaag gcctggaatg gatgggagtt atcaccctg  ggagcggcac cattaattac     180
gcccagaaat tcagggacg  agtgacgatt accgccgacg agtccaccag tactgcctac     240
atggagctgt cctcactccg cagcgaggac acggcagttt actactgcgc cggagtcga     300
tgggaccctc tttactatta tgctctggaa tactggggcc agggaacgac cgttacagtg     360
tcatctgcta gcacaaaagg accatcagtc ttcccacttg ctccttcatc taagagcaca     420
agtggtggca ctgcagccct ggctgcctg  gtgaaagatt atttccccga acctgttaca     480
gtttcttgga actccggtgc actgacatcc ggagtacaca ctttcccagc tgtgctgcag     540
agctcaggac tgtatagcct gtcttcggtg gtcactgttc catcgtcgag tcttggcaca     600
cagacatata tttgcaacgt caatcacaag ccctccaaca caaaagtgga taagaaggtc     660
gagcccaaat cttgtgacaa gacccatacg tgtcctccct gtcccgcccc tgaactgctg     720
ggaggcccct tctgtgttcct gttcccacct aagccaaagg acactctgat gatcagccgg     780
actccccgagg ttacctgtgt ggtggtggat gtgtctcatg aagaccctga ggttaagttc     840
aattggtacg tggatggcgt cgaggtgcat aacgcaaaaa ccaagccgag agaggagcag     900
tacaatagca cctatagagt agtgagcgtc ctgactgtct acatcagga  ttggctcaat     960
ggtaaagaat ataagtgcaa ggtaagcaac aaggccctac ccgcaccaat agagaagacc    1020
atctccaagg cgaaaggtca gcccaggag  ccccaggttt atacactgcc tccctcacgc    1080
gacgaattaa caaagaatca ggtgtctctc acctgtctcg tcaagggctt ttaccttcc     1140
gacatcgccg tggagtggga atccaatggc cagcctgaga caattataa  gacaactccc    1200
ccagtcctgg attcagatgg gtcgttcttt ctatatagta agttgaccgt ggataagtct    1260
cgctggcaac agggaacgt  gttctcttgc tctgttatgc atgaagcgct gcacaatcat    1320
tatacccaga agtccctgtc cctgagcccc gggaag                              1356
```

<210> SEQ ID NO 21
<211> LENGTH: 212
<212> TYPE: PRT
<213> ORGANISM: Homo sapiens

<400> SEQUENCE: 21

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125
```

```
Leu Gln Asn Arg Phe Glu Ser Ser Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

<210> SEQ ID NO 22
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 23
<211> LENGTH: 448
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
            290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
            325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380
```

-continued

```
Asn Gly Gln Pro Glu Asn Asn Tyr Lys Thr Thr Pro Pro Met Leu Asp
            385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 24
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230

<210> SEQ ID NO 25
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 25

Ser Ala Ser Thr Lys Gly Pro Ser Val Phe Pro Leu Ala Pro Cys Ser
1               5                   10                  15

Arg Ser Thr Ser Glu Ser Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Asn Phe Gly Thr Gln
65                  70                  75                  80

Thr Tyr Thr Cys Asn Val Asp His Lys Pro Ser Asn Thr Lys Val Asp
                85                  90                  95

Lys Thr Val Glu Arg Lys Cys Cys Val Glu Cys Pro Pro Cys Pro Ala
            100                 105                 110

Pro Pro Val Ala Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Phe Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ala Pro Ile Glu Lys Thr Ile Ser Lys Thr Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 26
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 26

```
gacatagtga tgactcaaag tccggacagc ctggcggtgt cactcggcga acgggcaact    60
atcaactgcc gagccagcga gagcgtcgat aattacggca tccccttcat gaactggtat   120
cagcagaagc caggacagcc gcccaagctg cttatctacg ccgcttccaa ccggggatca   180
ggggtgcccg atcgatttag tggaagcggt agtgggaccg atttcacact gaccatcagc   240
tcccttcagg ccgaggatgt ggctgtctat tattgtcagc aatccgagga agtgccgctc   300
acgtttggtc agggaaccaa actggagatc aagcggaccg tagcggcgcc tagtgtcttc   360
atcttcccac cctccgacga acagctgaag tctggcactg cttccgtcgt gtgcctgctc   420
aacaactttt accctagaga ggcaaaagtt caatggaaag tagacaatgc cttgcagtcc   480
gggaactccc aggagtctgt cacagagcag gatagtaagg actcaaccta cagcctgtcc   540
agcacactga ccctctccaa agccgactac gagaagcaca aagtgtacgc ttgcgaagtt   600
acgcatcagg ggctgtcctc acccgttaca aaaagtttta acagagggga gtgc          654
```

<210> SEQ ID NO 27
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser
        115                 120
```

<210> SEQ ID NO 28
<211> LENGTH: 467
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30
```

-continued

```
Pro Gly Ser Ser Val Lys Val Ser Cys Lys Ala Ser Gly Tyr Ala Leu
            35                  40                  45
Ser Asn Tyr Leu Ile Glu Trp Val Arg Gln Ala Pro Gly Gln Gly Leu
        50                  55                  60
Glu Trp Met Gly Val Ile Thr Pro Gly Ser Gly Thr Ile Asn Tyr Ala
65                  70                  75                  80
Gln Lys Phe Gln Gly Arg Val Thr Ile Thr Ala Asp Glu Ser Thr Ser
                85                  90                  95
Thr Ala Tyr Met Glu Leu Ser Ser Leu Arg Ser Glu Asp Thr Ala Val
            100                 105                 110
Tyr Tyr Cys Ala Arg Ser Arg Trp Asp Pro Leu Tyr Tyr Ala Leu
        115                 120                 125
Glu Tyr Trp Gly Gln Gly Thr Thr Val Thr Val Ser Ser Ala Ser Thr
        130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Asn Phe Gly Thr Gln Thr Tyr Thr Cys
        210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Gln Phe Asn Trp Tyr Val Asp Gly Val Glu Val
        290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
        355                 360                 365
Tyr Thr Leu Pro Pro Ser Arg Glu Glu Met Thr Lys Asn Gln Val Ser
        370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
```

His Glu Ala Leu His Asn His Tyr Thr Gln Lys Ser Leu Ser Leu Ser
            450                 455                 460

Pro Gly Lys
465

<210> SEQ ID NO 29
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Gly Gly Gly Ser Gly Gly Gly Gly Ser Gly Gly Gly Gly Ser
1               5                   10                  15

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Asp Lys Thr His Thr
1               5

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Tyr Val Leu Pro Asn Tyr Leu Ile Glu
1               5                   10

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Val Thr Thr Pro Gly Gly Gly Thr Ile Asn
1               5                   10

<210> SEQ ID NO 33
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 33

Ser Arg Trp Asp Pro Leu Tyr Tyr Tyr Ala Leu Glu Tyr
1               5                   10

<210> SEQ ID NO 34
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Arg Ala Ser Glu Ser Val Asp Asn Tyr Gly Ile Pro Phe Met Asn
1               5                   10                  15

<210> SEQ ID NO 35
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ala Ala Ser Asn Arg Gly Ser
1               5

<210> SEQ ID NO 36
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gln Gln Ser Glu Glu Val Pro Leu Thr
1               5

<210> SEQ ID NO 37
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
        35                  40                  45

Gly Val Thr Thr Pro Gly Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser
        115                 120

<210> SEQ ID NO 38
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val

<210> SEQ ID NO 39
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
        35                  40                  45

Gly Val Thr Thr Pro Gly Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

-continued

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230

<210> SEQ ID NO 40
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
caagtgcagc tggtgcagtc aggggccgag gttaagaagc agggagcag cgtcaaggta      60 tcttgtaaag cgtctggtta cgtccttcca aactacctga tcgaatgggt gaggcaggct    120
cccggccaag gcctggaatg gatgggagtt accaccctg ggggcggcac cattaattac     180
gcccagaaat tcagggacg agtgacgatt accgccgacg agtccaccag tactgcctac    240
atggagctgt cctcactccg cagcgaggac acggcagttt actactgcgc ccggagtcga    300
tgggaccctc tttactatta tgctctggaa tactggggcc agggaacgac cgttacagtg    360
tcatctgcta gcacaaaagg accatcagtc ttcccacttg ctccttcatc taagagcaca    420
agtggtggca ctgcagccct ggctgcctg gtgaaagatt atttccccga acctgttaca     480
gtttcttgga actccggtgc actgacatcc ggagtacaca ctttcccagc tgtgctgcag    540
agctcaggac tgtatagcct gtcttcggtg gtcactgttc catcgtcgag tcttggcaca    600
cagacatata tttgcaacgt caatcacaag ccctccaaca caaagtgga taagaaggtc      660 gagcccaaat cttgtgacaa aacacacaca                                      690

<210> SEQ ID NO 41
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
                20                  25                  30

Leu Ile Glu Trp Val Arg Gln Ala Pro Gly Gln Gly Leu Glu Trp Met
            35                  40                  45

Gly Val Thr Thr Pro Gly Gly Gly Thr Ile Asn Tyr Ala Gln Lys Phe
        50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 42
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 43
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
caagtgcagc tggtgcagtc aggggccgag gttaagaagc agggagcag  cgtcaaggta      60 tcttgtaaag cgtctggtta cgtccttcca aactacctga tcgaatgggt gaggcaggct     120
cccggccaag gcctggaatg gatgggagtt accaccctg ggggcggcac cattaattac      180
gcccagaaat tcagggacg agtgacgatt accgccgacg agtccaccag tactgcctac     240
atggagctgt cctcactccg cagcgaggac acggcagttt actactgcgc ccggagtcga     300
tgggaccctc tttactatta tgctctggaa tactggggcc agggaacgac cgttacagtg     360
tcatctgcta gcaccaaggg cccatcggtc ttccccctgg cgcctgctc caggagcacc     420 tccgagagca cagcggccct gggctgcctg gtcaaggact acttccccga accggtgacg     480
gtgtcgtgga actcaggcgc tctgaccagc ggcgtgcaca ccttcccggc tgtcctacag     540

```
tcctcaggac tctactccct cagcagcgtg gtgaccgtgc cctccagcaa cttcggcacc    600
cagacctaca cctgcaacgt agatcacaag cccagcaaca ccaaggtgga caagacagtt    660
gagcgcaaat gttgtgtcga gtgcccaccg tgcccagcac cacctgtggc aggaccgtca    720
gtcttcctct tccccccaaa acccaaggac accctcatga tctcccggac ccctgaggtc    780
acgtgcgtgg tggtggacgt gagccacgaa gaccccgagg tccagttcaa ctggtacgtg    840
gacggcgtgg aggtgcataa tgccaagaca aagccacggg aggagcagtt caacagcacg    900
ttccgtgtgg tcagcgtcct caccgtcgtg caccaggact ggctgaacgg caaggagtac    960
aagtgcaagg tctccaacaa aggcctccca gcccccatcg agaaaaccat ctccaaaacc    1020
aaagggcagc cccgagaacc acaggtgtac accctgcccc catcccggga ggagatgacc    1080
aagaaccagg tcagcctgac ctgcctggtc aaaggcttct accccagcga catcgccgtg    1140
gagtgggaga gcaatgggca gccggagaac aactacaaga ccacacctcc catgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                          1344
```

<210> SEQ ID NO 44
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

```
gacatagtga tgactcaaag tccggacagc ctggcggtgt cactcggcga acgggcaact     60
atcaactgcc gagccagcga gagcgtcgat aattacggca tccccttcat gaactggtat    120
cagcagaagc caggacagcc gcccaagctg cttatctacg ccgcttccaa ccggggatca    180
ggggtgcccg atcgatttag tggaagcggt agtgggaccg atttcacact gaccatcagc    240
tcccttcagg ccgaggatgt ggctgtctat tattgtcagc aatccgagga agtgccgctc    300
acgtttggtc agggaaccaa actggagatc aagcggaccg tagcggcgcc tagtgtcttc    360
atcttcccac cctccgacga acagctgaag tctggcactg cttccgtcgt gtgcctgctc    420
aacaactttt accctagaga ggcaaaagtt caatggaaag tagacaatgc cttgcagtcc    480
gggaactccc aggagtctgt cacagagcag gatagtaagg actcaaccta cagcctgtcc    540
agcacactga ccctctccaa agccgactac gagaagcaca aagtgtacgc ttgcgaagtt    600
acgcatcagg gctgtcctc acccgttaca aaaagttta acagagggga gtgc            654
```

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid except Ala
<220> FEATURE:
<221> NAME/KEY: MOD_RES
<222> LOCATION: (5)..(5)
<223> OTHER INFORMATION: Any amino acid except Ser

```
<400> SEQUENCE: 45

Gly Tyr Xaa Leu Xaa Asn Tyr Leu Ile Glu
1               5                   10

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid except Ile
<220> FEATURE:
<221> NAME/KEY: MOD_RES
<222> LOCATION: (6)..(6)
<223> OTHER INFORMATION: Any amino acid except Ser

<400> SEQUENCE: 46

Val Xaa Thr Pro Gly Xaa Gly Thr Ile Asn
1               5                   10

<210> SEQ ID NO 47
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
        35                  40                  45

Gly Val Thr Thr Pro Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205
```

His Lys Pro Ser Asn Thr Lys Val Asp Lys Thr Val Glu Arg Lys Cys
        210                 215                 220
Cys Val Glu Cys Pro Pro Cys Pro Ala Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser His Glu Asp Pro
                260                 265                 270
Glu Val Gln Phe Asn Trp Tyr Val Asp Gly Val Glu Val His Asn Ala
                275                 280                 285
Lys Thr Lys Pro Arg Glu Glu Gln Phe Asn Ser Thr Phe Arg Val Val
        290                 295                 300
Ser Val Leu Thr Val Val Ala Gln Asp Trp Leu Asn Gly Lys Glu Tyr
305                 310                 315                 320
Lys Cys Lys Val Ser Asn Lys Gly Leu Pro Ala Pro Ile Glu Lys Thr
                325                 330                 335
Ile Ser Lys Thr Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
        420                 425                 430
Leu His Asn His Tyr Thr Gln Lys Ser Leu Ser Leu Ser Pro Gly Lys
        435                 440                 445

<210> SEQ ID NO 48
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 48
caagtgcagc tggtgcagtc aggggccgag gttaagaagc cagggagcag cgtcaaggta      60
tcttgtaaag cgtctggtta cgtccttcca aactacctga tcgaatgggt gaggcaggct     120
cccggccaag gcctggaatg gatgggagtt accacccctg ggggcggcac cattaattac     180
gcccagaaat ttcagggacg agtgacgatt accgccgacg agtccaccag tactgcctac     240
atggagctgt cctcactccg cagcgaggac acggcagttt actactgcgc ccggagtcga     300 tgggacccctc tttactatta tgctctggaa tactgggggcc agggaacgac cgttacagtg     360
tcatctgcta gcaccaaggg cccatcggtc ttccccctgg cgccctgctc caggagcacc     420
tccgagagca gcgcggccct gggctgcctg gtcaaggact acttccccga accggtgacg     480
gtgtcgtgga actcaggcgc tctgaccagc ggcgtgcaca ccttcccggc tgtcctacag     540
tcctcaggac tctactccct cagcagcgtg gtgaccgtgc cctccagcaa cttcggcacc     600
cagacctaca cctgcaacgt agatcacaag cccagcaaca ccaaggtgga caagacagtt     660

-continued

```
gagcgcaaat gttgtgtcga gtgcccaccg tgcccagcac cacctgtggc aggaccgtca    720
gtcttcctct tccccccaaa acccaaggac accctcatga tctcccggac ccctgaggtc    780
acgtgcgtgg tggtggacgt gagccacgaa gaccccgagg tccagttcaa ctggtacgtg    840
gacggcgtgg aggtgcataa tgccaagaca aagccacggg aggagcagtt caacagcacg    900
ttccgtgtgg tcagcgtcct caccgtcgtg gcccaggact ggctgaacgg caaggagtac    960
aagtgcaagg tctccaacaa aggcctccca gcccccatcg agaaaaccat ctccaaaacc   1020
aaagggcagc cccgagaacc acaggtgtac accctgcccc catcccggga ggagatgacc   1080
aagaaccagg tcagcctgac ctgcctggtc aaaggcttct accccagcga catcgccgtg   1140
gagtgggaga gcaatgggca gccggagaac aactacaaga ccacacctcc catgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 49
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 49

Met Asp Trp Thr Trp Arg Ile Leu Phe Leu Val Ala Ala Ala Thr Gly
1               5                   10                  15

Ala His Ser

<210> SEQ ID NO 50
<211> LENGTH: 227
<212> TYPE: PRT
<213> ORGANISM: Homo sapiens

<400> SEQUENCE: 50

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 51
<211> LENGTH: 223
<212> TYPE: PRT
<213> ORGANISM: Homo sapiens

<400> SEQUENCE: 51

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 52
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
        35                  40                  45

Gly Val Thr Thr Pro Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Gly Gly Gly Ser Gly
            115                 120                 125

Gly Gly Gly Ser Gly Gly Gly Ser Asp Ile Val Met Thr Gln Ser
130                 135                 140

Pro Asp Ser Leu Ala Val Ser Leu Gly Glu Arg Ala Thr Ile Asn Cys
145                 150                 155                 160

Arg Ala Ser Glu Ser Val Asp Asn Tyr Gly Ile Pro Phe Met Asn Trp
                165                 170                 175

Tyr Gln Gln Lys Pro Gly Gln Pro Pro Lys Leu Leu Ile Tyr Ala Ala
            180                 185                 190

Ser Asn Arg Gly Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Ser Glu Glu Val Pro Leu Thr Phe Gly
225                 230                 235                 240

Gln Gly Thr Lys Leu Glu Ile Lys Arg Thr Val
            245                 250

<210> SEQ ID NO 53
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65              70                  75                  80

Ser Leu Gln Ala Glu Asp Val Ala Val Tyr Tyr Cys Gln Gln Ser Glu
                85                  90                  95
```

```
Glu Val Pro Leu Thr Phe Gly Gln Gly Thr Lys Leu Glu Ile Lys Arg
                100                 105                 110

Thr Val Gly Gly Gly Ser Gly Gly Gly Ser Gly Gly Gly Gly
        115                 120                 125

Ser Gln Val Gln Leu Val Gln Ser Gly Ala Glu Val Lys Lys Pro Gly
130                 135                 140

Ser Ser Val Lys Val Ser Cys Lys Ala Ser Gly Tyr Val Leu Pro Asn
145                 150                 155                 160

Tyr Leu Ile Glu Trp Val Arg Gln Ala Pro Gly Gln Gly Leu Glu Trp
                165                 170                 175

Met Gly Val Thr Thr Pro Gly Gly Thr Ile Asn Tyr Ala Gln Lys
                180                 185                 190

Phe Gln Gly Arg Val Thr Ile Thr Ala Asp Glu Ser Thr Ser Thr Ala
                195                 200                 205

Tyr Met Glu Leu Ser Ser Leu Arg Ser Glu Asp Thr Ala Val Tyr Tyr
        210                 215                 220

Cys Ala Arg Ser Arg Trp Asp Pro Leu Tyr Tyr Tyr Ala Leu Glu Tyr
225                 230                 235                 240

Trp Gly Gln Gly Thr Thr Val Thr Val Ser Ser
                245                 250
```

<210> SEQ ID NO 54
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
                20                  25                  30

Leu Ile Glu Trp Val Arg Gln Ala Pro Gly Gln Gly Leu Glu Trp Met
            35                  40                  45

Gly Val Thr Thr Pro Gly Gly Thr Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys
210                 215                 220
```

IL-6 ANTIBODIES

RELATED APPLICATIONS

This application claims priority to International Patent Application No. PCT/US2015/059532, filed on Nov. 6, 2015, which claims priority to U.S. Provisional Application No. 62/077,105, filed Nov. 7, 2014; U.S. Provisional Application No. 62/087,448, filed Dec. 4, 2014; and U.S. Provisional Application No. 62/247,705, filed Oct. 28, 2015. The entire contents of each of these applications are incorporated herein by reference.

FIELD OF THE INVENTION

The field of the invention relates to IL-6. More particularly, the field relates to modulators of IL-6 and their uses in treating disease such as diseases of the eye.

BACKGROUND

IL-6 is a pleiotropic cytokine with reported roles in inflammation, hematopoiesis, angiogenesis, cell differentiation, and neuronal survival. The present invention relates to improved IL-6 antibodies and uses thereof.

SUMMARY

The invention relates to IL-6 antibodies and fragments (e.g., antigen-binding fragments) or derivatives thereof, as well as nucleic acids encoding the IL-6 antibodies and fragments. The invention also relates to uses of such antibodies, fragments, or derivatives. The antibodies and fragments or derivatives thereof can be used, for example, in the treatment of an IL-6 associated disease. In embodiments, the antibody, fragment, or derivative thereof can bind (e.g., specifically bind) to an IL-6, e.g., to a human IL-6. In embodiments, the antibody, fragment, or derivative thereof can bind (e.g., specifically bind) to site II of an IL-6 (e.g., site II of human IL-6).

In one aspect provided herein is an isolated antibody or antigen binding fragment comprising a heavy chain variable region comprising
(i) a VH CDR1 comprising the sequence of GYX$_1$LX$_2$NYLIE (SEQ ID NO:45),
(ii) a VH CDR2 comprising the sequence of VX$_3$TPGX$_4$GTIN (SEQ ID NO:46), and
(ii) a VH CDR3,
wherein one or more (e.g., 1, 2, 3, or all) of the following is true: X$_1$ is not A, X$_2$ is not S, X$_3$ is not I and X$_4$ is not S. In embodiments, X$_1$ is not A, X$_2$ is not S, X$_3$ is not I and X$_4$ is not S.

In embodiments, X$_1$ is V or a conservative substitution for V. In embodiments, X$_2$ is P or a conservative substitution for P. In embodiments, X$_3$ is T or a conservative substitution for T. In embodiments, X$_4$ is G or a conservative substitution for G. In embodiments, one, two, three or all of the following is true: X$_1$ is V or a conservative substitution for V, X$_2$ is P or a conservative substitution for P, X$_3$ is T or a conservative substitution for T, and X$_4$ is G or a conservative substitution for G. In embodiments, X$_1$ is V or a conservative substitution for V, X$_2$ is P or a conservative substitution for P, X$_3$ is T or a conservative substitution for T, and X$_4$ is G or a conservative substitution for G.

In embodiments, X$_1$ is selected from V, I, L and M. In embodiments, X$_1$ is selected from V, I and L. In embodiments, X$_2$ is selected from P, G, and A. In embodiments, X$_2$ is selected from P and G. In embodiments, X$_3$ is selected from T and S. In embodiments, X$_4$ is selected from G and P.

In embodiments, one or more (e.g., 1, 2, 3, or all) of the following is true: X$_1$ is V, X$_2$ is P, X$_3$ is T, and X$_4$ is G. In embodiments, X$_1$ is V, X$_2$ is P, X$_3$ is T, and X$_4$ is G.

In embodiments, the VH CDR3 comprises the sequence of SEQ ID NO:33.

In embodiments, the antibody or antigen binding fragment has increased affinity for human IL-6 and/or increased potency. In embodiments, the antibody or antigen binding fragment has increased affinity for human IL-6 and/or increased potency compared with an antibody or antigen binding fragment (e.g., an otherwise identical antibody or antigen binding fragment) comprising a sequence wherein one or more (e.g., 1, 2, 3, or all) of the following is true: X$_1$ is A, X$_2$ is S, X$_3$ is I and X$_4$ is S.

In some embodiments, the isolated antibody or antigen binding fragment thereof comprises a VH CDR1 comprising the sequence of SEQ ID NO:31, a VH CDR2 comprising the sequence of SEQ ID NO:32, and optionally a VH CDR3 comprising the sequence of SEQ ID NO:33.

In embodiments, the heavy chain variable region comprises a sequence that is at least 90, 91, 92, 93, 94, 95, 96, 97, 98, or 99% identical with SEQ ID NO:17. In embodiments, the heavy chain variable region consists of a sequence is at least 90, 91, 92, 93, 94, 95, 96, 97, 98, or 99% identical with SEQ ID NO:17 or differs by no more than 5, 4, 3, 2, or 1 amino acids from SEQ ID NO:17. In embodiments, the heavy chain variable region differs by no more than 5, 4, 3, 2, or 1 amino acids from SEQ ID NO:17. In embodiments, the heavy chain variable region differs by 1-5 amino acids from SEQ ID NO:17.

In embodiments, the heavy chain variable region comprises a sequence that is at least 90, 91, 92, 93, 94, 95, 96, 97, 98, or 99% identical to SEQ ID NO:37. In embodiments, the heavy chain variable region consists of a sequence is at least 90, 91, 92, 93, 94, 95, 96, 97, 98, or 99% identical to SEQ ID NO:37. In embodiments, the heavy chain variable region differs by no more than 5, 4, 3, 2, or 1 amino acids from SEQ ID NO:37. In embodiments, the antibody or antigen binding fragment comprises a heavy chain variable region sequence comprising SEQ ID NO:37.

In embodiments, the antibody or antigen binding fragment comprises a heavy chain variable region sequence consisting of SEQ ID NO:37.

In embodiments, the antibody or antigen binding fragment comprises a sequence that is at least 90, 91, 92, 93, 94, 95, 96, 97, 98, or 99% identical to SEQ ID NO:39. In embodiments, the antibody or antigen binding fragment comprises a sequence that differs by no more than 5, 4, 3, 2, or 1 amino acids from SEQ ID NO:39. In embodiments, the antibody or antigen binding fragment comprises SEQ ID NO:39. In embodiments, the antibody or antigen binding fragment is a Fab.

In embodiments, the antibody or antigen binding fragment comprises a sequence that is at least 90, 91, 92, 93, 94, 95, 96, 97, 98, or 99% identical to SEQ ID NO:54. In embodiments, the antibody or antigen binding fragment comprises a sequence that differs by no more than 5, 4, 3, 2, or 1 amino acids from SEQ ID NO:54. In embodiments, the antibody or antigen binding fragment comprises SEQ ID NO:54. In embodiments, the antibody or antigen binding fragment is a Fab.

In embodiments, the antibody or antigen binding fragment is an scFv. In embodiments, the antibody or antigen binding comprises or consists of the scFv sequence (SEQ ID NO: 52)
QVQLVQSGAEVKKPGSSVKVSCKASGYVLPNYLIEWVRQAPGQGLEWMGV

TTPGGGTINYAQKFQGRVTITADESTSTAYMELSSLRSEDTAVYYCARSR

WDPLYYALEYWGQGTTVTVSSGGGGSGGGGSGGGGSDIVMTQSPDSLAV

SLGERATINCRASESVDNYGIPFMNWYQQKPGQPPKLLIYAASNRGSGVP

DRFSGSGSGTDFTLTISSLQAEDVAVYYCQQSEEVPLTFGQGTKLEIKRT

V or (SEQ ID NO: 53)
DIVMTQSPDSLAVSLGERATINCRASESVDNYGIPFMNWYQQKPGQPPKL

LIYAASNRGSGVPDRFSGSGSGTDFTLTISSLQAEDVAVYYCQQSEEVPL

TFGQGTKLEIKRTVGGGGSGGGGSGGGGSQVQLVQSGAEVKKPGSSVKVS

CKASGYVLPNYLIEWVRQAPGQGLEWMGVTTPGGGTINYAQKFQGRVTIT

ADESTSTAYMELSSLRSEDTAVYYCARSRWDPLYYYALEYWGQGTTVTVS

S.

In embodiments, the antibody or antigen binding fragment comprises a sequence that is at least 90, 91, 92, 93, 94, 95, 96, 97, 98, or 99% identical to SEQ ID NO:52 or SEQ ID NO:53. In embodiments, the antibody or antigen binding fragment comprises SEQ ID NO:52 or SEQ ID NO:53. In embodiments, the antibody or antigen binding fragment is an scFv.

In embodiments, the antibody or antigen binding fragment comprises a heavy chain sequence that is at least 90, 91, 92, 93, 94, 95, 96, 97, 98, or 99% identical to SEQ ID NO:41. In embodiments, the antibody or antigen binding fragment comprises a heavy chain sequence that differs by no more than 5, 4, 3, 2, or 1 amino acids from SEQ ID NO:41. In embodiments, the antibody or antigen binding fragment comprises a heavy chain sequence comprising SEQ ID NO:41. In embodiments, the antibody or antigen binding fragment comprises a heavy chain sequence consisting of SEQ ID NO:41.

In embodiments, the antibody or antigen binding fragment has increased affinity for human IL-6 and/or increased potency compared with EBI-029 or a fragment thereof. In embodiments, the antibody or antigen binding fragment has increased affinity for human IL-6 and/or increased potency compared with an antibody or antigen binding fragment comprising a VH CDR1 comprising the sequence of SEQ ID NO:4, a VH CDR2 comprising the sequence of SEQ ID NO:5, and optionally a VH CDR3 comprising the sequence of SEQ ID NO:6. In embodiments, the antibody or antigen binding fragment has increased affinity for human IL-6 and/or increased potency compared with an antibody or antigen binding fragment comprising a heavy chain variable region sequence comprising or consisting of SEQ ID NO:17. In embodiments, the antibody or antigen binding fragment has increased affinity for human IL-6 and/or increased potency compared with an antibody or antigen binding fragment comprising SEQ ID NO:24. In embodiments, the antibody or antigen binding fragment has increased affinity for human IL-6 and/or increased potency compared with an antibody or antigen binding fragment comprising a heavy chain sequence comprising or consisting of SEQ ID NO: 11.

In embodiments, the antibody or antigen binding fragment comprises one or more sequences of EBI-030 or EBI-031 as provided in Table 4. In embodiments, the antibody or antigen binding fragment comprises one or more domains of EBI-030 or EBI-031 as shown in FIG. 15 (e.g., one or more of FR1, CDR1, FR2, CDR2, FR3, CDR3, FR4, CH1, hinge, CH2, and CH3 of the heavy chain sequence and/or FR1, CDR1, FR2, CDR2, FR3, CDR3, FR4, and CK of the light chain sequence). In embodiments, the antibody or antigen binding fragment comprises a heavy chain and a light chain. In embodiments, the heavy and light chains are linked by one or more disulfide bonds. In embodiments, the antibody or antigen binding fragment is a Fab. In embodiments, the antibody or antigen binding fragment is an scFv. In embodiments, the antibody or antigen binding fragment is Fab, Fab', F(ab')2, scFv or Fv fragment.

In embodiments, the antibody or antigen binding fragment has increased affinity for human IL-6 and/or increased potency compared with an antibody or antigen binding fragment comprising one or more corresponding sequences of EBI-029, or sequences of an antibody described in WO2014/074905, hereby incorporated by reference in its entirety. In embodiments, antibody or antigen binding fragment has increased affinity for human IL-6 and/or increased potency compared with tocilizumab.

TABLE 4

Summary overview of sequences of EBI-029, EBI-030, and EBI-031

| Description | SEQ ID NO: | Sequence | | | | |
|---|---|---|---|---|---|---|
| EBI-029 HC (IgG2) aa sequence | SEQ ID NO: 11 | QVQLVQSGAE PGQGLEWMGV TAVYYCARSR SESTAALGCL VTVPSSNFGT VFLFPPKPKD KPREEQFNST KCQPREPQVY EWESNGQPEN GNVFSCSVMH | VKKPGSSVKV ITPGSGTINY WDPLYYALE VKDYFPEPVT QTYTCNVDHK TLMISRTPEV FRVVSVLTVV TLPPεREEMT NYKTTPPMLD EALHNHYTQK | SCKASGYALS AQKFQGRVTI YWGQGTTVTV VSWNSGALTS PSNTKVDKTV TCVVVDVSHE HQDWLNGKEY KNQVεLTCLV SDGSFFLYSK SLSLSPGK | NYLIEWVRQA TADESTSTAY SSASTKGPSV GVHTFPAVLQ ERKCCVECPP DPEVQFNWYV KCKVSNKGLP KGFYPεDIAV LTVDKSRWQQ | MELSSLRSED FPLAPCSRST SSGLYSLSSV CPAPPVAGPS DGVEVHNAKT APIEKTISKT |
| EBI-029 HC - H311A | SEQ ID NO: 10 | QVQLVQSGAE PGQGLEWMGV TAVYYCARSR SESTAALGCL VTVPSSNFGT VFLFPPKPKD KPREEQFNST KGQPREPQVY | VKKPGSSVKV ITPGSGTINY WDPLYYALE VKDYFPEPVT QTYTCNVDHK TLMISRTPEV FRVVSVLTVV TLPPSREEMT | SCKASGYALS AQKFQGRVTI YWGQGTTVTV VSWNSGALTS PSNTKVDKTV TCVVVDVSHE AQDWLNGKEY KNQVSLTCLV | NYLIEWVRQA TADESTSTAY SSASTKGPSV GVHTFPAVLQ ERKCCVECPP DPEVQFNWYV KCKVSNKGLP KGFYPSDIAV | MELSSLRSED FPLAPCSRST SSGLYSLSSV CPAPPVAGPS DGVEVHNAKT APIEKTISKT |

TABLE 4-continued

Summary overview of sequences of EBI-029, EBI-030, and EBI-031

| Description | SEQ ID NO: | Sequence |
|---|---|---|
| | | EWESNGQPEN NYKTTPPMLD SDGSFFLYSK LTVDKSRWQQ GNVFSCSVMH EALHNHYTQK SLSLSPGK |
| EBI-029 LC aa sequence | SEQ ID NO: 12 | DIVMTQSPDS LAVSLGERAT INCRASESVD NYGIPFMNWY QQKPGQPPKL LIYAASNRGS GVPDRFSGSG SGTDFTLTIS SLQAEDVAVY YCQQSEEVPL TFGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| EBI-029 (IgG1) Fab HC sequence | SEQ ID NO: 24 | QVQLVQSGAE VKKPGSSVKV SCKASGYALS NYLIEWVRQA PGQGLEWMGV ITPGSGTINY AQKFQGRVTI TADESTSTAY MELSSLRSED TAVYYCARSR WDPLYYYALE YWGQGTTVTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSCDKTHT |
| EBI-029 VH aa sequence | SEQ ID NO: 17 | QVQLVQSGAEVKKPGSSVKVSCKASGYALSNYLIE WVRQAPGQGLEWMGVITPGSGTINYAQKFQGRVTIT ADESTSTAYMELSSLRSEDTAVYYCARSRWDPLYYYALEY WGQGTTVTVSS |
| EBI-029 VL aa sequence | SEQ ID NO: 18 | DIVMTQSPDSLAVSLGERATINCRASESVDNYGIPFMNWYQQ KPGQPPKLLIYAASNRGSGVPDRFSGSGSGTDFTLTISSLQAE DVAVYYCQQSEEVPLTFGQGTKLEIKRTV |
| EBI-029 HC CDR1 | SEQ ID NO: 4 | GYALSNYLIE |
| EBI-029 HC CDR2 | SEQ ID NO: 5 | VITPGSGTIN |
| EBI-029 HC CDR3 | SEQ ID NO: 6 | SRWDPLYYYALEY |
| EBI-029 LC CDR1 | SEQ ID NO: 7 | RASESVDNYGIPFMN |
| EBI-029 LC CDR2 | SEQ ID NO: 8 | AASNRGS |
| EBI-029 LC CDR3 | SEQ ID NO: 9 | QQSEEVPLT |
| EBI-030 HC (IgG2) aa sequence | SEQ ID NO: 41 | QVQLVQSGAE VKKPGSSVKV SCKASGYVLP NYLIEWVRQA PGQGLEWMGV TTPGGGTINY AQKFQGRVTI TADESTSTAY MELSSLRSED TAVYYCARSRWDPLYYYALE YWGQGTTVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| EBI-030 LC aa sequence | SEQ ID NO: 42 | DIVMTQSPDS LAVSLGERAT INCRASESVD NYGIPFMNWY QQKPGQPPKL LIYAASNRGS GVPDRFSGSG SGTDFTLTIS SLQAEDVAVY YCQQSEEVPLTFGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| EBI-030 (IgG1) Fab HC aa sequence | SEQ ID NO: 39 | QVQLVQSGAE VKKPGSSVKV SCKASGYVLP NYLIEWVRQA PGQGLEWMGV TTPGGGTINY AQKFQGRVTI TADESTSTAY MELSSLRSED TAVYYCARSR WDPLYYYALE YWGQGTTVTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSCDKTHT |
| EBI-030 (IgG2) Fab HC aa sequence | SEQ ID NO: 54 | QVQLVQSGAEVKKPGSSVKVSCKASGYVLPNYLIEWVRQAPGQGLEWMGV TTPGGGTINYAQKFQGRVTITADESTSTAYMELSSLRSEDTAVYYCARSWD PLYYYALEYWGQGTTVTVSSASTKGPSVFPLAPCSRSTSESTAALGCLVKDY FPEPVTVSWNSGALTSGVHTFPAVLQSSGLYSLSSVVTVPSSNFGTQTYTCN VDHKPSNTKVDKTVERK |
| EBI-030 VH aa sequence | SEQ ID NO: 37 | QVQLVQSGAE VKKPGSSVKV SCKASGYVLP NYLIEWVRQA PGQGLEWMGV TTPGGGTINY AQKFQGRVTI TADESTSTAY MELSSLRSED TAVYYCARSR WDPLYYYALE YWGQGTTVTV SS |

TABLE 4-continued

Summary overview of sequences of EBI-029, EBI-030, and EBI-031

| Description | SEQ ID NO: | Sequence |
|---|---|---|
| EBI-030 VL aa sequence | SEQ ID NO: 38 | DIVMTQSPDSLAVSLGERATINCRASESVDNYGIPFMNWYQQKPGQPPKWY AASNRGSGVPDRFSGSGSGTDFTLTISSLQAEDVAVYYCQQSEEVPLTFG QGTKLEIKRTV |
| EBI-030 HC CDR1 | SEQ ID NO: 31 | GYVLPNYLIE |
| EBI-030 HC CDR2 | SEQ ID NO: 32 | VTTPGGGTIN |
| EBI-030-HC CDR3 | SEQ ID NO: 33 | SRWDPLYYYALEY |
| EBI-030 LC CDR1 | SEQ ID NO: 34 | RASESVDNYGIPFMN |
| EBI-030 LC CDR2 | SEQ ID NO: 35 | AASNRGS |
| EBI-030 LC CDR3 | SEQ ID NO: 36 | QQSEEVPLT |
| EBI-031 IgG2 HC aa sequence | SEQ ID NO: 47 | QVQLVQSGAE VKKPGSSVKV SCKASGYVLP NYLIEWVRQA PGQGLEWMGV TTPGGGTINY AQKFQGRVTI TADESTSTAY MELSSLRSED TAVYYCARSR WDPLYYYALE YWGQGTTVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV DGVEVHNAKT KPREEQFNST FRVVSVLTVV AQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| scFv VH-VL aa sequence | SEQ ID NO: 52 | QVQLVQSGAEVKKPGSSVKVSCKASGYVLPNYLIEWVRQAPGQGLEWMGV TTPGGGTINYAQKFQGRVTITADESTSTAYMELSSLRSEDTAVYYCARSRWD PLYYYALEYWGQGTTVTVSSGGGGSGGGGSGGGGSDIVMTQSPDSLAVSL GERATINCRASESVDNYGIPFMNWYQQKPGQPPKLLIYAASNRGSGVPDRFS GSGSGTDFTLTISSLQAEDVAVYYCQQSEEVPLTFGQGTKLEIKRTV |
| scFv VL-VH aa sequence | SEQ ID NO: 53 | DIVMTQSPDSLAVSLGERATINCRASESVDNYGIPFMNWYQQKPGQPPKWY AASNRGSGVPDRFSGSGSGTDFTLTISSLQAEDVAVYYCQQSEEVPLTFGQ GTKLEIKRTVGGGGSGGGGSGGGGSQVQLVQSGAEVKKPGSSVKVSCKAS GYVLPNYLIEWVRQAPGQGLEWMGVTTPGGGTINYAQKFQGRVTITADEST STAYMELSSLRSEDTAVYYCARSRWDPLYYYALEYWGQGTTVTVSS | aa = amino acid;
na = nucleic acid;
HC = heavy chain;
LC = light chain;
VH = heavy chain variable region;
VL = light chain variable region Increased affinity and/or increased potency can be assessed using methods described herein and/or methods known in the art.

In embodiments, the affinity is assessed using surface plasmon resonance (SPR).

In embodiments, the affinity is increased by at least 1.5, 1.6, 1.7, 1.8. 1.9, 2, 3, or 4 fold.

In embodiments, the potency is increased. In embodiments, the potency is increased as indicated by a decrease in the IC50 and/or a decrease in the IC90. In embodiments, the IC50 is decreased by at least 5, 10, 20, 30, 40, or 50 fold. In embodiments, the IC50 is decreased by at least about 50 fold. In embodiments, the IC90 is decreased by at least 10, 20, 30, 40, 50, 60, 70, 80, 90, 100, 200, 300, 400, or 500 fold. In embodiments, the IC90 is decreased by at least about 100 fold.

In embodiments, the potency is assessed, e.g., by using a HEK-Blue™ assay or a T1165 proliferation assay.

In embodiments, the antibody or antigen binding fragment inhibits cis-IL-6 signaling, e.g., as assessed based on the IC50 or IC90 value obtained using a HEK-Blue™ assay described herein, e.g., with 20 pM free IL-6.

In embodiments, the antibody or antigen binding fragment has an IC50 of less than 47 pM and/or an IC90 of less than 4350 pM. In embodiments, the IC50 is less than 47 pM, e.g., less than 40, 30, 20, 10, 5, 4, 3, 2, or 1 pM. In embodiments, the IC90 is less than 4350 pM, e.g., less than 4000, 2000, 1000, 100, 50, 40, 30, 20, 15, 10, or 5 pM. In embodiments, the IC50 and/or IC90 is assessed in a HEK-Blue™ assay with 20 pM IL-6.

In embodiments, the antibody or antigen binding fragment blocks free IL-6 with greater potency compared to tocilizumab, e.g., as assessed based on the IC50 values obtained using a HEK-Blue™ assay with 20 pM IL-6. In embodiments, the antibody or antigen binding fragment inhibits IL-6 with more than 900 fold greater potency compared to tocilizumab. In embodiments, the antibody or antigen binding fragment is EBI-031 or an antigen binding fragment thereof. In embodiments, the antibody or antigen binding fragment has an IC50 of less than 15 pM, e.g., an IC50 of 14.2 pM, for inhibition of IL-6.

In embodiments, the antibody or antigen binding fragment blocks trans-IL-6 signaling, e.g., as assessed using a HEK-Blue™ assay described herein, e.g., with 200 pM hyper IL-6. In embodiments, the antibody or antigen binding fragment inhibits signaling by hyper IL-6. In embodiments, the antibody or antigen binding fragment inhibits signaling by hyper IL-6 with greater potency than tocilizumab, e.g., with more than 900 fold greater potency compared to tocilizumab. In embodiments, the antibody or antigen binding fragment inhibits signaling by hyper IL-6 with an IC50 of less than 1 pM. In embodiments, the antibody or antigen binding fragment inhibits signaling by hyper IL-6 with an IC50 of less than 1 nM. In embodiments, the antibody or antigen binding fragment inhibits signaling by hyper IL-6 with an IC50 of less than 100 pM or less than 50 pM, e.g., with an IC50 of about 14-15 pM. In embodiments, the antibody or antigen binding fragment is EBI-031 or an antigen binding fragment thereof.

In embodiments, the antibody or antigen binding fragment inhibits cis-IL-6 signaling and trans-IL-6 signaling.

In embodiments, the antibody or antigen binding fragment is effective in blocking IL-6 signaling in the eye for at least 1 month, 2 months, 3 months, 4 months, 5 months, or 6 months, e.g., following intravitreal administration. In embodiments, the antibody or antigen binding fragment blocks 95% of IL-6 signaling in the eye for at least 1 month, 2 months, 3 months, 4 months, 5 months, or 6 months, e.g., following intravitreal administration. In embodiments, the antibody or antigen binding fragment blocks 95% of IL-6 signaling in the eye for about 150 days.

In another aspect provided herein is an isolated antibody or antigen binding fragment comprising a heavy chain variable region sequence that is at least 90, 91, 92, 93, 94, 95, 96, 97, 98, or 99% identical to SEQ ID NO:37, wherein said heavy chain sequence comprises one or more (e.g., 1, 2, 3, or 4) amino acids selected from V28, P30, T51, and G55 (numbering of amino acids is according to SEQ ID NO:41).

In a further aspect provided herein is an isolated antibody or antigen binding fragment comprising a sequence that is at least 90, 91, 92, 93, 94, 95, 96, 97, 98, or 99% identical to SEQ ID NO:39, wherein said sequence comprises one or more (e.g., 1, 2, 3, or 4) amino acids selected from V28, P30, T51, and G55 (numbering of amino acids is according to SEQ ID NO:41).

In a further aspect provided herein is an isolated antibody or antigen binding fragment comprising a sequence that is at least 90, 91, 92, 93, 94, 95, 96, 97, 98, or 99% identical to SEQ ID NO:54, wherein said sequence comprises one or more (e.g., 1, 2, 3, or 4) amino acids selected from V28, P30, T51, and G55 (numbering of amino acids is according to SEQ ID NO:41).

Also provided herein is an isolated antibody or antigen binding fragment comprising a heavy chain sequence that is at least 90, 91, 92, 93, 94, 95, 96, 97, 98, or 99% identical to SEQ ID NO:41, wherein said heavy chain sequence comprises one or more (e.g., 1, 2, 3, or 4) amino acids selected from V28, P30, T51, and G55 (numbering of amino acids is according to SEQ ID NO:41).

In embodiments, the antibody or antigen binding fragment has increased affinity for human IL-6 relative to a control antibody, e.g., relative to EBI-029 or a fragment thereof. In embodiments, the antibody or antigen binding fragment has increased affinity for human IL-6 relative to an antibody or antigen binding fragment that is otherwise identical except that it does not comprise said one or more amino acids selected from V28, P30, T51, and G55 and instead comprises one or more (e.g., 1, 2, 3, or 4) amino acids selected from A28, S30, I51, and S55. In embodiments, the affinity is increased by at least 1.5, 1.6, 1.7, 1.8, 1.9, 2, 3, or 4 fold. In embodiments, the affinity is assessed using surface plasmon resonance (SPR).

In embodiments, the antibody or antigen binding fragment has increased potency relative to a control antibody, e.g., e.g., relative to EBI-029 or a fragment thereof. In embodiments, the antibody or antigen binding fragment has increased potency relative to an antibody or antigen binding fragment that is otherwise identical except that it does not comprise said one or more amino acids selected from V28, P30, T51, and G55 and instead comprises one or more (e.g., 1, 2, 3, or 4) amino acids selected from A28, S30, I51, and S55.

In embodiments, the potency is increased as indicated by a decrease in the IC50 and/or a decrease in the IC90. In embodiments, the IC50 is decreased by at least 5, 10, 20, 30, 40, or 50 fold. In embodiments, the IC50 is decreased by at least about 50 fold. In embodiments, the IC90 is decreased by at least 10, 20, 30, 40, 50, 60, 70, 80, 90, 100, 200, 300, 400, or 500 fold. In embodiments, the IC90 is decreased by at least about 100 fold.

In embodiments, the potency is assessed using a HEK-Blue™ assay or a T1165 proliferation assay.

In embodiments, the antibody or antigen binding fragment has an IC50 of less than 47 pM and/or an IC90 of less than 4350 pM. In embodiments, the IC50 is less than 47 pM, e.g., less than 40, 30, 20, 10, 5, 4, 3, 2, or 1 pM. In embodiments, the IC90 is less than 4350 pM, e.g., less than 4000, 2000, 1000, 100, 50, 40, 30, 20, 15, 10, or 5 pM. In embodiments, the IC50 and/or IC90 is assessed in a HEK-Blue assay with 20 pM IL-6.

In some embodiments, the antibody or antigen binding fragment comprises V28, P30, T51, and G55 and the antibody or antigen binding fragment shows improved affinity for human IL-6 and/or improved potency compared with an antibody or antigen binding fragment that is otherwise identical except that it comprises A28, S30, I51, and S55.

In embodiments, an antibody or antigen binding fragment described herein further comprises a light chain variable region or antigen binding fragment thereof, comprising a VL CDR1, a VL CDR2, and a VL CDR3.

In embodiments, the VL CDR1 comprises the sequence of SEQ ID NO:34, the VL CDR2 comprises the sequence of SEQ ID NO:35, and the VL CDR3 comprises the sequence of SEQ ID NO:36.

In embodiments, the antibody or antigen binding fragment further comprises a light chain variable region sequence that is at least 90, 91, 92, 93, 94, 95, 96, 97, 98, or 99% identical to SEQ ID NO:38.

In embodiments, the antibody or antigen binding fragment further comprises a light chain variable region sequence that comprises SEQ ID NO:38 or that differs from SEQ ID NO:38 by no more than 5, 4, 3, 2, or 1 amino acids.

In embodiments, the antibody or antigen binding fragment further comprises a light chain variable region sequence comprising SEQ ID NO:38. In embodiments, the light chain variable region sequence consists of SEQ ID NO:38.

In embodiments, the antibody or antigen binding fragment further comprises a light chain sequence that is at least 90, 91, 92, 93, 94, 95, 96, 97, 98, or 99% identical to SEQ ID NO:42.

In embodiments, the antibody or antigen binding fragment further comprises a light chain sequence that differs by no more than 5, 4, 3, 2, or 1 amino acids from SEQ ID NO:42.

In embodiments, the antibody or antigen binding fragment further comprises a light chain sequence comprising SEQ ID NO:42.

In embodiments, the antibody or antigen binding fragment further comprises a light chain sequence comprising SEQ ID NO:42 or a sequence that differs by no more than 5, 4, 3, 2, or 1 amino acids from SEQ ID NO:42. In embodiments, the light chain sequence consists of SEQ ID NO:42.

In embodiments, the antibody or antigen binding fragment comprises
(i) a VH CDR1 comprising the sequence of SEQ ID NO:31, a VH CDR2 comprising the sequence of SEQ ID NO:32, and a VH CDR3 comprising the sequence of SEQ ID NO:33 and
(ii) a VL CDR1 comprising the sequence of SEQ ID NO:34, a VL CDR1 comprising the sequence of SEQ ID NO:35, and a VL CDR3 comprising the sequence of SEQ ID NO:36. In embodiments, the antibody or antigen binding fragment comprises the foregoing CDRs except that it has a mutation, e.g., a total of at most 1, 2, or 3 mutations in all six of the CDRs. In embodiments, the mutation(s) does not decrease the affinity and/or potency of the antibody or antigen binding fragment.

In embodiments, the antibody or antigen binding fragment is an IgG1, an IgG2, an IgG3, or an IgG4 antibody or fragment thereof. In embodiments, the antibody or antigen binding fragment is an IgG1 or an IgG2 antibody or fragment thereof. In embodiments, the antibody or antigen binding fragment is an IgG1 Fab or an IgG2 Fab. In embodiments, the antibody or antigen binding fragment is an IgG2 antibody or antigen binding fragment.

In embodiments, the antibody or antigen binding fragment is engineered to reduce or eliminate ADCC activity.

In embodiments, the antibody or antigen binding fragment is a monoclonal antibody or an antigen binding fragment thereof. In embodiments, the antibody or antigen binding fragment is a humanized or human monoclonal antibody or an antigen binding fragment thereof.

In embodiments, the antibody or antigen binding fragment comprises a heavy chain variable region comprising or consisting of SEQ ID NO:37 and a light chain variable region comprising or consisting of SEQ ID NO:38. In embodiments, the antibody or antigen binding fragment comprises the foregoing heavy and light chain variable regions except that it has a mutation, e.g., a total of at most 1, 2, or 3 mutations. In embodiments, the mutation(s) does not decrease the affinity and/or potency of the antibody or antigen binding fragment.

In embodiments, the antibody or antigen binding fragment comprises a heavy chain sequence comprising SEQ ID NO:41 and optionally a light chain sequence comprising SEQ ID NO:42.

In embodiments, the antibody or antigen binding fragment comprises a heavy chain sequence consisting of SEQ ID NO:41 and optionally a light chain sequence consisting of SEQ ID NO:42.

In embodiments, the antibody or antigen binding fragment comprises a heavy chain sequence comprising SEQ ID NO:47 and optionally a light chain sequence comprising SEQ ID NO:42.

In embodiments, the antibody or antigen binding fragment comprises a heavy chain sequence that is identical to SEQ ID NO:41 and a light chain sequence that is identical to SEQ ID NO:42, except that the antibody or antigen binding fragment comprises a mutation (e.g., 1, 2, 3, 4, or 5 total mutations relative to SEQ ID NO:41 and/or SEQ ID NO:42). In embodiments, the mutation(s) is in the framework region(s). In embodiments, the mutation does not decrease the affinity and/or potency of the antibody or antigen binding fragment relative to an antibody or antigen binding fragment that does not comprise said mutation.

In embodiments, the antibody or antigen binding fragment comprises a heavy chain sequence that is identical to SEQ ID NO:47 and a light chain sequence that is identical to SEQ ID NO:42, except that the antibody or antigen binding fragment comprises a mutation (e.g., 1, 2, 3, 4, or 5 total mutations relative to SEQ ID NO:47 and/or SEQ ID NO:42). In embodiments, the mutation(s) is in the framework region(s). In embodiments, the mutation does not decrease the affinity and/or potency of the antibody or antigen binding fragment relative to an antibody or antigen binding fragment that does not comprise said mutation In one embodiment, the antibody or antigen binding fragment is a Fab.

In one embodiment, the antibody or antigen binding fragment is an IgG1 Fab.

In one embodiment, the antibody or antigen binding fragment is an isolated Fab comprising a heavy chain sequence comprising SEQ ID NO:39 and a light chain sequence comprising SEQ ID NO:42. In one embodiment, the antibody or antigen binding fragment is an isolated Fab comprising a heavy chain sequence consisting of SEQ ID NO:39 and a light chain sequence consisting of SEQ ID NO:42.

In one embodiment, the antibody or antigen binding fragment is an IgG2 Fab.

In one embodiment, the antibody or antigen binding fragment is an isolated Fab comprising a heavy chain sequence comprising SEQ ID NO:54 and a light chain sequence comprising SEQ ID NO:42. In one embodiment, the antibody or antigen binding fragment is an isolated Fab comprising a heavy chain sequence consisting of SEQ ID NO:54 and a light chain sequence consisting of SEQ ID NO:42.

In embodiments, the antibody or antigen binding fragment comprises a heavy chain sequence that is identical to SEQ ID NO:39 and a light chain sequence that is identical to SEQ ID NO:42, except that the antibody or antigen binding fragment comprises a mutation (e.g., 1, 2, 3, 4, or 5 total mutations relative to SEQ ID NO:39 and/or SEQ ID NO:42). In embodiments, the mutation(s) is in the framework region(s). In embodiments, the mutation does not decrease the affinity and/or potency of the antibody or antigen binding fragment relative to an antibody or antigen binding fragment that does not comprise said mutation.

In embodiments, the antibody or antigen binding fragment comprises a heavy chain sequence that is identical to SEQ ID NO:54 and a light chain sequence that is identical to SEQ ID NO:42, except that the antibody or antigen binding fragment comprises a mutation (e.g., 1, 2, 3, 4, or 5 total mutations relative to SEQ ID NO:54 and/or SEQ ID NO:42). In embodiments, the mutation(s) is in the framework region(s). In embodiments, the mutation does not decrease the affinity and/or potency of the antibody or antigen binding fragment relative to an antibody or antigen binding fragment that does not comprise said mutation.

In some embodiments, the antibody or antigen binding fragment can bind to at least one of R24, K27, Y31, D34, S118, or V121 of human IL-6. In embodiments, the antibody or antigen binding fragment can bind to R24, K27, Y31, D34, S118, and V121 of human IL-6. In embodiments, the antibody or antigen binding fragment can bind to at least 1, at least 2, at least 3, at least 4, or at least 5 of R24, K27, Y31, D34, S118, and V121 of human IL-6.

In embodiments, the antibody or antigen binding fragment can bind (e.g., can specifically bind) to site II of a human IL-6.

In embodiments, the antibody or an antigen binding fragment thereof can bind to an IL-6 with a $T_m$ of 70° C. or greater.

In embodiments, the antibody or antigen binding fragment thereof can bind to an IL-6 with a $T_m$ of 80° C. or greater.

In embodiments, the antibody or fragment thereof (e.g., an antigen binding fragment thereof) binds to at least one of R24, K27, Y31, D34, S118, and V121 of a human IL-6.

In embodiments, the antibody or an antigen binding fragment thereof binds to at least two of R24, K27, Y31, D34, S118, and V121 of a human IL-6. In embodiments, the antibody an antigen binding fragment thereof binds to at least three of R24, K27, Y31, D34, S118, and V121 of a human IL-6. In embodiments, the antibody or antigen binding fragment thereof binds to at least four of R24, K27, Y31, D34, S118, and V121 of a human IL-6. In embodiments, the antibody or antigen binding fragment thereof binds to at least five of R24, K27, Y31, D34, S118, and V121 of a human IL-6. In embodiments, the antibody or antigen binding fragment thereof binds to R24, K27, Y31, D34, S118, and V121 of human IL-6.

In embodiments, the antibody or antigen binding fragment is a monoclonal antibody or an antigen binding fragment thereof. In embodiments, the antibody or antigen binding fragment is a humanized monoclonal antibody. In embodiments, the antibody or antigen binding fragment human monoclonal antibody.

In embodiments, the antibody or antigen binding fragment exhibits <10% aggregation at a concentration of 100-150 mg/mL, e.g., at a concentration of about 142 mg/mL. in PBS, pH 7.4.

In embodiments, the antibody or antigen binding fragment has improved pharmacokinetic properties compared with another therapeutic agent, e.g., compared with tocilizumab, bevacizumab, ranibizumab, and/or Eylea. In embodiments, the antibody or antigen binding fragment has improved retention in the eye when administered to the eye, e.g., intravitreally, e.g., by intravitreal injection. In embodiments, improved retention in the eye is indicated by an increased half life in the eye, e.g., in the vitreous, retina, aqueous humor, choroid and/or sclera.

In embodiments, the antibody or antigen binding fragment has a half life in the vitreous of at least 6, 7, 8, 9, 10, 11, 12, 13, 14, 15, 16, 17, 18, 19, or 20 days. In embodiments, the half life in the vitreous is at least 10 days. In embodiments, the half in the vitreous is assessed in an animal, e.g., in a rabbit or a monkey. In embodiments, the half life in the vitreous is assessed in a human.

In embodiments, an antibody or antigen binding fragment described herein has a reduced systemic half life (e.g., a lower $T_{1/2\beta}$) and/or an improved systemic clearance, e.g., a reduced systemic half life or faster systemic clearance compared with that of another therapeutic agent, e.g., tocilizumab, bevacizumab, ranibizumab, and/or aflibercept (Eylea®). In embodiments, the systemic half life (e.g., $T_{1/2\beta}$) is lower than that of tocilizumab and/or aflibercept (Eylea@).

In embodiments, the antibody or antigen binding fragment comprises an Fc domain comprising a mutation (e.g., at 1, 2, 3, or 4 mutations) at one or more positions corresponding to H311, D313, I254, or H436 (numbering as in SEQ ID NO:41). In embodiments, the mutation is selected from one or more of H311A, H311E, H311N, D313T, I254A, I254R, and H436A. In embodiments, the antibody or antigen binding fragment comprises an Fc domain comprising a mutation corresponding to H311A (numbering as in SEQ ID NO:41). In embodiments, the Fc domain is an IgG1 Fc domain. In embodiments, the Fc domain is an IgG2 Fc domain.

In embodiments, the Fc domain is a human IgG1 Fc domain having the sequence of SEQ ID NO:50 and optionally comprises a mutation at one or more of the underlined positions: (H90, D92,I33, and H215):

(SEQ ID NO: 50)
DKTHTCPPCPAPELLGGPSVFLFPPKPKDTLM<u>I</u>SRTPEVTCVVVDVSHED

PEVKFNWYVDGVEVHNAKTKPREEQYNSTYRVVSVLTVL<u>H</u>Q<u>D</u>WLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHN<u>H</u>YTQKSLSLSPGK.

In embodiments, the IgG1 Fc domain comprises a mutation corresponding to one or more of H90A, H90E, H90N, D92T, I33A, I33R, and H215A (numbering according to SEQ ID NO:50).

In embodiments, the Fc domain is a human IgG2 Fc domain having the sequence of SEQ ID NO:51 and optionally comprises a mutation at one or more of the underlined positions (H86, D88,I29, and H211):

(SEQ ID NO: 51)
VECPPCPAPPVAGPSVFLFPPKPKDTLM<u>I</u>SRTPEVTCVVVDVSHEDPEVQ

FNWYVDGVEVHNAKTKPREEQFNSTFRVVSVLTVV<u>H</u>Q<u>D</u>WLNGKEYKCKVS

NKGLPAPIEKTISKTKGQPREPQVYTLPPSREEMTKNQVSLTCLVKGFYP

SDIAVEWESNGQPENNYKTTPPMLDSDGSFFLYSKLTVDKSRWQQGNVFS

CSVMHEALHN<u>H</u>YTQKSLSLSPGK.

In embodiments, the IgG2 Fc domain comprises a mutation corresponding to one or more of H86A, H86E, H86N, D88T, I29A, I29R, and H211A (numbering according to SEQ ID NO:51).

In embodiments, the Fc mutation reduces the systemic accumulation of the antibody or antigen binding fragment (e.g., increases clearance or decreases half life, e.g., the $T_2\beta$) of the antibody or antigen binding fragment. In embodiments, the systemic accumulation is reduced compared with that of another therapeutic agent (e.g., tocilizumab, bevacizumab, ranibizumab, and/or aflibercept). In embodiments, the systemic accumulation is reduced compared with that of tocilizumab and/or aflibercept. In embodiments, the systemic accumulation is reduced compared with the systemic accumulation of a corresponding antibody or antigen binding fragment that does not comprise the mutation. In embodiments, the systemic accumulation is assessed following intravitreal administration of the antibody or antigen binding fragment.

In another aspect provided herein is a method of reducing systemic effects of inhibiting an IL-6 in a subject, the method comprising administering to the subject an antibody or fragment thereof comprising a mutated Fc domain as described herein. In embodiments, the antibody or antigen binding fragment can inhibit an activity of IL-6 and has reduced Fc activity (e.g., reduced binding to FcRn) compared to a corresponding antibody or fragment thereof having a wild type Fc domain. In some cases, the method of reducing systemic effects of inhibiting an IL-6 in a subject include administering to the subject an IL-6 antagonist that comprises a mutated Fc domain as described herein.

In a further aspect, provided herein is a nucleic acid comprising a sequence encoding an antibody or antigen binding fragment described herein. In embodiments, the nucleic acid encodes an amino acid sequence disclosed herein. In embodiments, the nucleic acid comprises SEQ ID NO:40, SEQ ID NO:43, or SEQ ID NO:48. In embodiments, the nucleic acid encodes a sequence disclosed in Table 4.

Also provided herein is a vector comprising the nucleic acid. Also provided herein is a cell comprising the nucleic acid or the vector.

In embodiments, an IL-6 antibody or antigen binding fragment described herein is for use in the treatment of a subject (e.g., a human) with an IL-6 associated disease. In embodiments, the disease is an ocular disease, e.g., an ocular disease characterized by an elevated level of IL-6, e.g., in the vitreous.

In embodiments, the antibody or antigen binding fragment is for use in the treatment of a subject (e.g., a human) with diabetic macular edema (DME), diabetic retinopathy, uveitis, glaucoma, dry eye (e.g., dry eye disease or dry eye syndrome), allergic conjunctivitis, ocular pain, rhegmatogenous retinal detachment (RRD), age-related macular degeneration (AMD), proliferative diabetic retinopathy (PDR), retinal vein occlusion (RVO), neuromyelitis optica (NMO), corneal transplant, corneal abrasion, or physical injury to the eye. In embodiments, the antibody or antigen binding fragment is for use in the treatment of a subject (e.g., a human) with DME.

In embodiments, an IL-6 antibody or antigen binding fragment described herein is for use in the preparation of a medicament for the treatment an IL-6 associated disease. In embodiments, the disease is an ocular disease, e.g., an ocular disease characterized by an elevated level of IL-6 in the vitreous. In embodiments, the IL-6 associated disease is diabetic macular edema (DME), diabetic retinopathy, uveitis, dry eye (e.g., dry eye disease or dry eye syndrome), age-related macular degeneration (AMD), proliferative diabetic retinopathy (PDR), rhegmatogenous retinal detachment (RRD), retinal vein occlusion (RVO), neuromyelitis optica (NMO), corneal transplant, corneal abrasion, or physical injury to the eye. In embodiments, the IL-6 associated disease is diabetic macular edema. In embodiments, the medicament is formulated for delivery to the vitreous of the subject's eye (e.g., for intravitreal injection).

Also provided herein is a composition comprising an antibody or antigen binding fragment described herein. In embodiments, the composition further comprises a pharmaceutically acceptable carrier and one or more pharmaceutically acceptable excipients.

In embodiments, the composition is for use in the treatment of an IL-6 associated disease. In embodiments, the disease is an ocular disease, e.g., an ocular disease characterized by an elevated level of IL-6 in the vitreous. In embodiments, the composition is for use in the treatment of diabetic macular edema (DME), diabetic retinopathy, uveitis, dry eye (e.g., dry eye disease or dry eye syndrome), age-related macular degeneration (AMD), proliferative diabetic retinopathy (PDR), Rhegmatogenous retinal detachment (RRD), retinal vein occlusion (RVO), neuromyelitis optica (NMO), corneal transplant, corneal abrasion, or physical injury to the eye.

Also provided herein is a method of treating an IL-6 associated disease, the method comprising administering to a subject a therapeutically effective amount of an IL-6 antibody or fragment described herein. In embodiments, the IL-6 associated disease is an ocular disease, e.g., an ocular disease characterized by an elevated level of IL-6 in the vitreous. In embodiments, the IL-6 associated disease is diabetic macular edema (DME), diabetic retinopathy, uveitis, dry eye (e.g., dry eye disease or dry eye syndrome), age-related macular degeneration (AMD), proliferative diabetic retinopathy (PDR), Rhegmatogenous retinal detachment (RRD), retinal vein occlusion (RVO), neuromyelitis optica (NMO), corneal transplant, corneal abrasion, or physical injury to the eye. In embodiments, the IL-6 associated disease is diabetic macular edema.

In embodiments, the antibody or antigen binding fragment, or the composition comprising the antibody or antigen binding fragment, is delivered to the vitreous of the subject's eye (e.g., by intravitreal injection). In embodiments, the antibody or antigen binding fragment, or the composition comprising the antibody or antigen binding fragment, is for intravitreal injection.

In embodiments, the IL-6 associated disease is diabetic macular edema and the antibody or fragment, or the composition comprising the antibody or antigen binding fragment, is delivered to the vitreous of the subject's eye.

Also provided herein is an antibody or fragment (e.g., an antigen binding fragment) thereof (e.g., an IL-6 antibody or fragment thereof as described herein), or a composition comprising such an antibody or fragment thereof, for use in the treatment of an IL-6 associated disease (e.g., for use in the treatment of a subject, e.g. a human subject, having an IL-6 associated disease).

In embodiments, said disease is an ocular disease characterized by an elevated level of IL-6, e.g., in the vitreous. In embodiments, said disease is diabetic macular edema (DME), diabetic retinopathy, uveitis, dry eye (e.g., dry eye disorder or dry eye disease), allergic conjunctivitis, age-related macular degeneration (AMD), proliferative diabetic retinopathy (PDR), Rhegmatogenous retinal detachment (RRD), retinal vein occlusion (RVO), neuromyelitis optica (NMO), corneal transplant, corneal abrasion, or physical injury to the eye. In embodiments, said disease is DME. In embodiments, said disease is dry eye disease. In embodiments, said disease is dry eye syndrome. In embodiments, said disease is uveitis. In embodiments, said disease is AMD. In embodiments, said disease is PDR. In embodiments, said disease is corneal transplant, corneal abrasion, or physical injury to the eye. In embodiments, the antibody or fragment (e.g., the antigen binding fragment) thereof is suitable for delivery to the vitreous of the eye. In embodiments, the antibody or fragment (e.g., the antigen binding fragment) thereof is delivered to the vitreous of the eye.

Also provided herein is a method of treating an IL-6 associated disease, the method comprising administering to a subject an IL-6 antibody or fragment thereof (e.g., an antigen binding fragment thereof), e.g., an IL-6 antibody or fragment thereof as described herein. In embodiments, the IL-6 antibody or fragment thereof (e.g., an antigen binding fragment thereof), is administered in a therapeutically effective amount. In embodiments, the IL-6 associated disease is an ocular disease characterized by an elevated level of IL-6 in the vitreous. In embodiments, the IL-6 associated disease is diabetic macular edema (DME), diabetic retinopathy, uveitis, dry eye syndrome, dry eye disease, age-related macular degeneration (AMD), proliferative diabetic retinopathy (PDR), retinal vein occlusion (RVO), neuromyelitis optica (NMO), corneal transplant, corneal abrasion, or physical injury to the eye.

In embodiments, the antibody or fragment thereof (e.g., the antigen binding fragment thereof), is suitable for delivery to the vitreous of the eye. In embodiments, the antibody or fragment thereof (e.g., the antigen binding fragment thereof), is delivered to the vitreous of the subject's eye. In embodiments, the IL-6 associated disease is diabetic macular edema and the antibody or fragment thereof is delivered to the vitreous of the subject's eye.

Also provided herein is a kit comprising an IL-6 antibody or composition disclosed herein and optionally, instructions for use.

Also provided herein is a container or device, e.g., a drug delivery device, comprising an IL-6 antibody or composition disclosed herein. In embodiments, said device is configured for delivery of the antibody or composition to the eye, e.g., to the vitreous. Also provided herein is a kit comprising said container or device.

As used herein, the term "antibody" is synonymous with immunoglobulin and is to be understood as commonly known in the art. The term antibody is not limited by any particular method of producing the antibody. For example, the term antibody includes, inter alia, recombinant antibodies, monoclonal antibodies, and polyclonal antibodies. As used herein, an antibody is a tetramer, and unless otherwise disclosed, each is composed of two identical pairs of polypeptide chains, each pair having one light chain and one heavy chain. The amino terminus of each chain comprises a variable region of about 100 to 120 or more amino acids that play a primary role in antigen recognition. The carboxyterminal portion of each chain comprises a constant region with a primary role in antibody effector function. Classes of human light chains are termed kappa and lambda light chains. Heavy chain classes are mu, delta, gamma, alpha, or epsilon, and define the isotype of an antibody. Antibody isotypes are IgM, IgD, IgG, IgA, and IgE, respectively. Within light and heavy chains, the variable and constant regions are joined by a "J" region of about 12 or more amino acids, with the heavy chain also including a "D" region of about three or more amino acids.

The variable regions of each heavy/light chain pair (VH and VL), respectively, form the antigen binding site. Accordingly, an intact IgG antibody, for example, has two binding sites. Except in bifunctional or bispecific antibodies, the two binding sites are the same.

Variable regions of antibody heavy and light chains exhibit the same general structure of relatively conserved framework regions (FR) joined by three hypervariable regions, also termed complementary determining regions or CDRs. The term "variable" refers to the fact that certain portions of the variable domains differ extensively in sequence among antibodies and are involved in the binding and specificity of each particular antibody for its particular antigen. Variability lies primarily in the CDRs, which are separated by the more highly conserved framework regions (FRs). The assignment of amino acids to each domain is made in accordance with the definitions of Kabat Sequences of Proteins of Immunological Interest (National Institutes of Health, Bethesda, Md. (1987 and 1991)), or Chothia and Lesk, J Mol Biol 196:901-917 (1987); Chothia et al., Nature 342:878-883 (1989), which describe methods known in the art.

"Wild type" can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

The term "antibody fragment" refers to a portion of an intact or a full-length chain or an antibody, generally the target binding or variable region. Examples of antibody fragments include, but are not limited to, Fab, Fab', F(ab')2 and Fv fragments. A "functional fragment" or "analog of an anti-IL-6 site II antibody" is a fragment that can prevent or substantially reduce the ability of IL-6 to bind to a receptor, reduce the ability of IL-6/IL-6R complex to bind to gp130, or reduce the ability of ligand to bind to gp130 or to initiate signaling. As used herein, "an antigen binding fragment" or "functional fragment" generally is synonymous with "antibody fragment" and can refer to fragments, such as Fv, Fab, F(ab')2 and so on which can prevent or substantially reduce the ability of IL-6 to bind to a receptor, reduce the ability of IL-6/IL-6R complex to bind to gp130, or to initiate signaling.

A "derivative" of an antibody is a polypeptide that includes at least one CDR of an antibody disclosed herein. Typically, the derivative can bind to site II of IL-6. "Compete" means that a first antibody, or fragment thereof can compete for binding with a second antibody or a fragment thereof, such that binding of the first antibody with its epitope is detectably decreased in the presence of the second antibody compared to the binding of the first antibody in the absence of the second antibody. In some cases, the term can also refer to the binding of the second antibody to its epitope which is detectably decreased in the presence of the first antibody. The mechanism of such competition can be via, in non-limiting examples, steric hindrance, conformational change, binding to a common epitope.

The term "percent sequence identity" in the context of nucleic acid sequences means the residues in two sequences that are the same when aligned for maximum correspondence. The length of sequence identity comparison may be over at least about nine nucleotides, for example, at least about 18 nucleotides, at least about 24 nucleotides, at least about 28 nucleotides, at least about 32 nucleotides, at least about 36 nucleotides, or at least about 48 or more nucleotides.

Algorithms known in the art can be used to measure nucleotide sequence identity. For example, polynucleotide sequences can be compared using FASTA, Gap or Bestfit (Wisconsin Package Version 10.0, Genetics Computer Group (GCG), Madison, Wis.). FASTA, includes, e.g., the programs FASTA2 and FASTA3, provides alignments and percent sequence identity of the regions of the best overlap between the query and search sequences (Pearson, Methods Enzymol 183:63-98 (1990); Pearson, Methods Mol Biol 132:185-219 (2000); Pearson, Methods Enzymol 266:227-258 (1996); Pearson, J Mol Biol 276:71-84 (1998); incorporated herein by reference). Default parameters for a particular program or algorithm are typically used. For example, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

The term "percent sequence identity" in the context of amino acid sequences means the residues in two sequences that are the same when aligned for maximum correspondence. The length of sequence identity comparison may be over at least about five amino acid residues, for example, at least about 20 amino acid residues, at least about 30 amino acid residues, at least about 50 amino acid residues, at least about 100 amino acid residues, at least about 150 amino acid residues, or at least about 200 or more amino acid residues. Sequence identity for polypeptides is typically measured using sequence analysis software. Algorithms for determination of percent sequence identity are known in the art. For example, amino acid sequences can be compared using FASTA, Gap or Bestfit (Wisconsin Package Version 10.0, Genetics Computer Group (GCG), Madison, Wis.). Protein analysis software matches sequences using measures of similarity assigned to various substitutions, deletions and other modifications, including conservative amino acid substitutions. For example, GCG contains programs such as "Gap" and "Bestfit," which can be used with default parameters as specified by the programs to determine sequence homology or sequence identity between closely related polypeptides, such as homologous polypeptides from different species of organisms or between a wild type protein and an analog thereof. See, e.g., GCG Version 6.1 (University of Wisconsin, Madison, Wis.). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, Methods Enzymol 183:63-98 (1990); Pearson, Methods Mol Biol 132:185-219 (2000)). Another algorithm that can be used when comparing a sequence to a database containing a large number of sequences from different organisms is the computer program BLAST, e.g., blastp or tblastn, using default parameters as supplied with the programs. See, e.g., Altschul et al., J Mol Biol 215:403-410 (1990); Altschul et al., Nucleic Acids Res 25:3389-402 (1997).

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein can comprise about 50%, 60%, 70%, 80%, 90%, 95%, 98%, or 99% pure; for example, a substantially pure polypeptide or protein is 50%, 60%, 70%, 80%, 90%, 95%, 98%, or 99% pure. Protein purity or homogeneity can be assessed by any appropriate means, such as polyacrylamide gel electrophoresis of a protein sample followed by visualizing one or more bands associated with the protein or polypeptide (e.g., upon staining the gel), size-exclusion HPLC, cation-exchange HPLC, reduced capillary electrophoresis in SDS, peptide mapping, or glycan mapping. Higher resolution can be achieved using methods known in the art, for example, or other means of purification.

The term "substantial similarity" when referring to a nucleic acid or fragment thereof, means that when optimally aligned with appropriate nucleotide insertions or deletions with another nucleic acid (or its complementary strand), there is nucleotide sequence identity in at least about 85%, at least about 90%, and at least about 95%, 96%, 97%, 98% or 99% of the nucleotide bases, for example, 85%, 90%, 95%, 96%, 98%, or 99% sequence identity as measured by any known algorithm of sequence identity, such as FASTA, BLAST or Gap.

As applied to polypeptides, the term "substantial identity" or "substantial similarity" means that two amino acid sequences, when optimally aligned, such as by the programs GAP or BESTFIT using default gap weights as supplied with the programs, share at least about 70%, 75%, 80%, 90%, 95%, 96%, 97%, 98%, or 99% sequence identity; e.g., 70%, 75%, 80%, 90%, 95%, 96%, 97%, 98%, or 99% sequence identity. In certain embodiments, residue positions that are not identical differ by conservative amino acid substitutions.

"Therapeutically effective amount" refers to that amount of a therapeutic agent being administered that will ameliorate at least one sign or symptom of a disease being treated or enhance or improve the prophylactic and or therapeutic effect(s) of another therapy (e.g., another therapeutic agent) useful for treating an IL-6 associated disease. It is understood that the therapeutically effective amount may be administered in multiple doses over a limited amount of time or as a chronic treatment.

"Treat", "treating" and "treatment" refer to a method of ameliorating one or more signs or symptoms of a disease.

As used herein, the term "disease" includes diseases and disorders.

The entire disclosure of each patent document and scientific article referred to herein, and those patent documents and scientific articles cited thereby, is expressly incorporated by reference herein for all purposes.

Additional features and advantages of the invention are more particularly described below.

BRIEF DESCRIPTION OF THE DRAWINGS

FIG. 15A depicts the locations of FR1, CDR1, FR2, CDR2, FR3, CDR3, FR4, CH1, hinge, CH2, and CH3 in the heavy chain sequences of EBI-029 (SEQ ID NO: 11), EBI-030 (SEQ ID NO: 41), and EBI-031 (EBI-031 is also referred to herein as EBI-030-H311A) (SEQ ID NO: 47).

DETAILED DESCRIPTION

Figure 1:
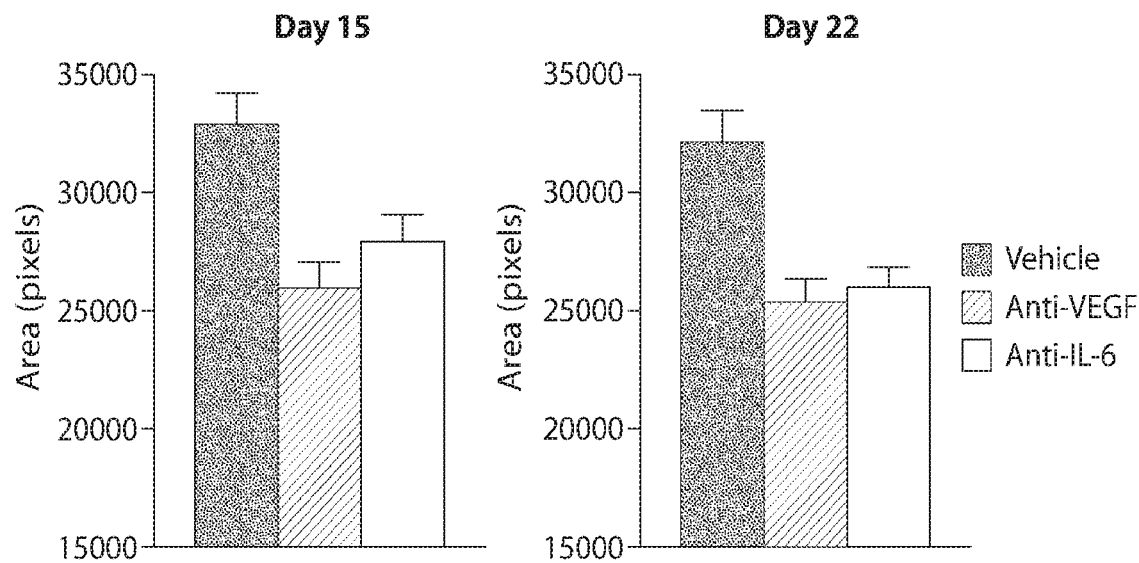
FIG. 1 is a graph illustrating results of an experiment in which an anti-IL-6 antibody was administered IVT in rat CNV model. Anti-VEGF antibody was administered as a positive control and the negative control was vehicle alone. p=0.0054 on Day 15 and p=0.0005 on Day 22 for anti-IL-6 vs. vehicle control.

IL-6 has been implicated as playing a role in a number of diseases such as rheumatoid arthritis, and has been reported to be significantly up-regulated in a number of diseases, including ocular diseases. IL-6 can act via both cis- and trans-mechanisms. In the cis mechanism, it is believed that free IL-6 binds to membrane bound IL-6 receptor (IL-6R is also referred to as IL-6Rα and CD126), and the IL-6/IL-6R complex then interacts with gp130 (also referred to as CD130, oncostatin M receptor, IL-6Rbeta, and IL-6 signal transducer), to activate signaling in the cell containing the complex. In the trans mechanism, free IL-6 binds to soluble IL-6 receptor (sIL-6R). The IL-6/sIL-6R complex can then bind to gp130 present in a cell membrane. A key difference between these mechanisms is that more cell types express gp130 than express IL-6R, whose expression is more limited. Therefore, in diseases for which it is desirable to inhibit IL-6 signaling, for example in those in which it is desirable to broadly inhibit IL-6 signaling, it is useful to inhibit both cis- and trans-IL-6 signaling. Applicants have engineered IL-6 antagonists, e.g., anti-IL-6 antibodies, fragments, and derivatives that can inhibit both cis and trans signaling by IL-6. In addition, applicants have engineered such IL-6 antagonists to achieve more rapid systemic clearance. IL-6 antagonists, e.g., IL-6 antibodies and fragments or derivatives thereof, are described in WO2014/074905, the entire content of which is hereby incorporated herein by reference. The present invention relates to improved IL-6 antibodies and uses thereof.

As used herein, singular terms, including but not limited to "a," "an", or "the," include the plural, unless the context clearly indicates otherwise.

Features of IL-6 antagonists (IL-6a)

In general, an IL-6 antagonist (IL-6a) described herein specifically binds to site II (site 2) of an IL-6 and is useful for treatment of IL-6 related eye disease and certain other diseases. An IL-6 related eye disease is one in which an undesirable symptom or biological activity of the disease is associated with the expression or presence of IL-6. In some embodiments the IL-6a has high affinity for both free and bound IL-6, is relatively stable in an organism, can inhibit binding to gp130 of an IL-6 bound to an IL-6R (termed herein an IL-6/IL-6R complex or IL-6/IL-6R), and can have a therapeutic effect. In general, the IL-6a is an antibody or is derived from an antibody. For example, an IL-6a is a high affinity, humanized Fab that can specifically bind to site II of an IL-6 and potently blocks both cis- and trans-IL-6 signaling. In another example, the IL-6a is a full length antibody, e.g., an IgG1 or IgG2 antibody.

In some embodiments, the Fab is also configured as an Fc-engineered sequence or is in a full-length antibody. In some embodiments, the Fc-engineered IL-6a (e.g., the Fc-engineered Fab) has more rapid systemic clearance compared with an appropriate control, e.g., compared with the corresponding antibody, fragment, or derivative thereof that does not have the engineered Fc. These and other features of an IL-6a are further described herein.

Applicants have designed IL-6 antagonists that selectively bind to site II of IL-6 to provide broad inhibition of IL-6 signaling because such molecules can inhibit the binding of gp130 to IL-6, regardless of whether the IL-6 is free or bound to membrane IL-6R or sIL-6R. Furthermore, targeting the ligand (IL-6) as opposed to the IL-6 receptor can avoid receptor mediated clearance and toxicity due to ADCC (antibody-dependent cell-mediated cytotoxicity). Because IL-6 plays both pathologic and protective roles in disease, use of an IL-6 antagonist (IL-6a) to treat a disease associated with increased IL-6 can improve certain aspects of a condition, but may also cause significant adverse effects, e.g., systemic effects. This duality of IL-6 pathways (i.e., the ability to have desirable and/or undesirable effects) can make it undesirable to treat an IL-6 associated disorder with a systemic inhibitor. Accordingly, the compositions and methods provided herein can be useful for treatments that inhibit at least one IL-6 activity, but do not have an undue effect on positive activities of IL-6, in part because the compositions can be formulated for local delivery, e.g., for local delivery to the eye. For example, in certain aspects, the IL-6a is designed to be of a size suitable for delivery to a particular site. In some embodiments, the IL-6a is a full-length antibody. In some embodiments, the IL-6a is derived from an antibody and is in a format that may have longer residency in the vitreous of the eye and limited systemic leakage. In some embodiments, the IL-6a is a modified antibody (e.g., an antibody with a modified Fc domain) that has longer residency in the vitreous of the eye and/or more limited systemic leakage compared with a corresponding unmodified antibody. In some embodiments, the IL-6a is an IgG2 antibody.

In some aspects, the IL-6a is a relatively small IL-6a such as a fragment of an antibody or other derivative of an antibody that is less than a full length antibody, e.g., a Fab that is derived from an IL-6 antibody. In some cases, an IL-6a is in a format that can pass from one part of a tissue to another with increased kinetics compared to a corresponding full-length IL-6 antibody. In some embodiments, the IL-6a is a Fab that has been engineered to be a larger molecule, which is more likely to have increased residence in the location to which it was delivered compared to the Fab alone, e.g., the IL-6a is dimerized through Fc domain. In certain embodiments, the Fc domain has been engineered such that the Fc moiety has ablated or reduced FcRn binding that can reduce systemic accumulation compared to the same IL-6 binding entity that includes a wild-type Fc. The engineered Fc domain can be, e.g., an IgG1 domain or an IgG2 domain.

Typically, the IL-6 antagonists described herein have a sufficiently high affinity for their target, IL-6, to be effective in ameliorating at least one undesirable effect of IL-6 and are sufficiently stable to be useful as therapeutics.

In general, the PK of an IL-6a, e.g., an IL-6a suitable for use in the eye has a sufficiently long half life in the site of delivery, e.g., the vitreous, to provide a therapeutic effect. In non-limiting examples, the PK can be a half-life of at least 8 days, 10 days, 14 days, 21 days, 28 days, or 30 days.

Identification of IL-6 antagonists binding to site II

In general, any method known in the art can be used to generate a molecule that can bind to an IL-6, for example, polypeptide libraries or molecular libraries can be screened for candidate compounds in an assay for the ability of a polypeptide or compound to bind to IL-6. Once such a candidate compound is identified, the binding site of the compound can be determined using methods known in the art. For example, a molecule can be tested for the ability to bind to wild type IL-6 and the binding compared to the ability of the compound to bind to an IL-6 mutated in site I, site II, or site III. In embodiments, an IL-6a as described herein retains the ability to bind to an IL-6/IL-6Rα complex and to IL-6, and prevents binding of IL-6/IL-6Rα to gp130. In embodiments, an IL-6a as described herein can compete with gp130 for binding to IL-6/IL-6Rα complex, e.g., by binding to site II of IL-6. Such binding activities can be assayed using methods known in the art.

IL-6a candidates can be tested, for example, using an HEK-Blue™ IL-6 assay system (InvivoGen, San Diego). HEK-Blue™ IL-6 cells are HEK293 cells that are stably transfected with human IL-6R and a STAT3-inducible SEAP reporter gene. In the presence of IL-6, STAT3 is activated and SEAP is secreted. SEAP is assessed using, for example, QUANTI-Blue™ (InvivoGen, San Diego). Addition of an IL-6 antagonist to the cells prevents secretion or decreases the level of SEAP as a result of inhibiting both free and soluble receptor bound IL-6.

$K_D$ refers to the binding affinity equilibrium constant of a particular antibody-antigen interaction or antibody fragment-antigen interaction. In embodiments, an antibody or antigen binding fragment described herein binds to an antigen (e.g., IL-6) with a $K_D$ that is less than or equal to 250 pM, e.g., less than or equal to 225 pM, 220 pM, 210 pM, 205 pM, 150 pM, 100 pM, 50 pM, 20 pM, 10 pM, or 1 pM. $K_D$ can be determined using methods known in the art, for example using surface plasmon resonance, for example, using the BiaCore™ system.

$K_{off}$ refers to the dissociation rate constant of a particular antibody-antigen interaction or antibody fragment-antigen complex. The dissociation rate constant can be determined using surface plasmon resonance, for example using the BiaCore™ system. A relatively slow $K_{off}$ can contribute to desirable features of a therapeutic, e.g., permitting less frequent administration of the inhibitor to a subject in need of such treatment.

Specificity

In some embodiments, an IL-6a described herein binds specifically to a target, e.g., an IL-6. In general, "specific binding" as used herein indicates that a molecule preferentially binds to a selected molecule and displays much lower binding affinity for one or more other molecules. In embodiments, the binding affinity for another molecule is 1, 2, 3 or more orders of magnitude lower than the binding affinity for the target.

As discussed supra, IL-6 can be present as free IL-6 and as IL-6 bound to soluble IL-6Rα. Applicants have identified site II of IL-6 as an optimal target for an IL-6 antagonist compared to an inhibitor that that binds to site I of an IL-6. A site I inhibitor may inhibit binding of free IL-6 to IL-6Rα. However, such an inhibitor cannot prevent activity initiated by pre-existing IL-6/IL-6R complexes except by replacement limited by the $k_{off}$ of the complex. Another alternative, an inhibitor that binds to an IL-6Rα, is less suitable because it may have limited ability to prevent IL-6 activity unless it is present in saturating concentrations. Because the amount of IL-6 receptor is generally quite high compared to the amount of IL-6, this approach may require the administration of an undesirably large amount of a composition that inhibits IL-6 activity by binding to the receptor. In embodiments, the IL-6 antagonists described herein (e.g., the antibodies and fragments and derivatives thereof described herein) can block the activity of IL-6 even when IL-6 is bound to IL-6R. Accordingly, an advantage of an IL-6a as described herein is that relatively less of the composition may need to be administered to achieve a therapeutic effect compared to an inhibitor targeting an IL-6 receptor. Anti-receptor antibodies have been reported to be cleared rapidly by receptor mediated clearance significantly limiting their PK, therefore requiring larger doses, more frequent dosing, or both. Additionally, both anti-receptor and anti-site I IL-6 antibodies pose a problem in that they significantly increase the tissue concentration of IL-6 by disrupting the normal receptor mediated clearance pathway of the ligand, thereby exposing the subject to potentially undesirable levels of IL-6 in a tissue. Furthermore, use of an inhibitor targeting IL-6Rα may necessitate the presence of the inhibitor near both sites at which inhibition is sought and a site at which it is not desirable, e.g., systemic treatment. Use of an IL-6a that binds site II, the site to which gp130 binds, permits inhibition via free IL-6 as well as IL-6 that is bound to an IL-6R, but has not yet activated an IL-6 pathway via gp130. Accordingly, without wishing to be bound by theory, the IL-6 antagonists described herein are designed to bind to both forms of IL-6 (soluble and receptor bound), specifically the IL-6 antagonists bind to site II of IL-6, which is accessible in both forms. Compositions containing an IL-6a as described herein can inhibit both cis and trans signaling by IL-6.

In some cases compounds and methods provided herein are designed to provide an effective IL-6 blockade sufficient to treat at least one sign or symptom of an IL-6 associated disorder, for example, inhibiting angiogenesis and/or inflammation.

Compounds described herein are useful for treating eye diseases characterized by an undesirably high level of IL-6, e.g., in the vitreous (see Yuuki et al., J Diabetes Compl 15:257 (2001); Funatsu et al., Ophthalmology 110: 1690, (2003); Oh et al., Curr Eye Res 35:1116 (2010); Noma et al., Eye 22:42 (2008); Kawashima et al., Jpn J Ophthalmol 51:100 (2007); Kauffman et al., Invest Ophthalmol Vis Sci 35:900 (1994); Miao et al., Molec Vis 18:574(2012)).

In general, an IL-6a as described herein is a potent antagonist of IL-6 signaling. In some embodiments, an IL-6a described herein has a high affinity for IL-6, for example, an IC50 less than or equal to 100 pM in an HEK-Blue IL-6 assay using 10 pM IL-6. High affinity of an IL-6a can be determined based on the $K_D$ of the IL-6a, for example, a $K_D$ of less than or equal to 1 nM, less than or equal to 500 pM, less than or equal to 400 pM, less than or equal to 300 pM, less than or equal to 240 pM, or less than or equal to 200 pM.

To produce a biologic IL-6a (e.g., a protein or polypeptide such as an antibody, fragment, or derivative thereof) that is useful for treating a disorder associated with increased IL-6 expression or activity, typically it is desirable that the biologic IL-6a have high productivity. For example, a suitable productivity is greater than or equal to 1 g/L (e.g., greater than or equal to 2 g/L, greater than or equal to 5 g/L, or greater than or equal to 10 g/L).

To effectively administer an IL-6 antagonist, it is necessary that the inhibitor have solubility compatible with the concentration at which it will be administered. For example, in the case of a full-length antibody IL-6a, the solubility is greater than or equal to 20 mg/ml, greater than or equal to 10 mg/ml, greater than or equal to 5 mg/ml, or greater than or equal to 1 mg/ml.

Furthermore, to be a viable treatment, the inhibitor must have high stability at the body temperature of the delivery and activity sites as well as storage stability. In embodiments, the inhibitor has a $T_m$ of greater than or equal to 60° C. (e.g., greater than or equal to 60° C., greater than or equal to 62.5° C., greater than or equal to 65° C., greater than or equal to 70° C., greater than or equal to 73° C., or greater than or equal to 75° C.). In embodiments, the inhibitor has a $T_{onset}$ of greater than or equal to 45° C., e.g., greater than or equal to 50° C., greater than or equal to 51° C., greater than or equal to 55° C., or greater than or equal to 60° C. Methods of determining the $T_m$ and $T_{onset}$ can be determined using methods known in the art.

Antagonists having the desired features can be selected from suitable types of molecules known in the art, for example antibodies, including fragments and derivatives of an IL-6 site II targeted antibody that generally retains or maintains sufficient features of the parent IL-6 antibody (e.g., desired binding properties). Such antagonists include $F_{ab}$ fragments, scFvs, $F_{ab}$ fragments engineered to include an Fc moiety, and full-length antibodies engineered to have a framework different from the parent IL-6 site II targeted antibody.

In some aspects, the IL-6a disclosed herein comprises a human antibody antigen-binding site that can compete or cross-compete with an antibody or fragment thereof that can bind to site II of IL-6. For example, the antibody or fragment thereof can be composed of a VH domain and a VL domain disclosed herein, and the VH and VL domains comprise a set of CDRs of an IL-6/site 11 binding antibody disclosed herein.

Any suitable method may be used to determine the domain and/or epitope bound by an IL-6a, for example, by mutating various sites on an IL-6. Those sites in which mutations prevent or decrease binding of the IL-6a and the IL-6 ligand are involved either directly in binding to the IL-6a or indirectly affect the binding site, e.g., by affecting conformation of the IL-6. Other methods can be used to determine the amino acids bound by an IL-6a. For example, a peptide-binding scan can be used, such as a PEPSCAN-based enzyme linked immuno assay (ELISA). In a peptide-binding scan of this type, short overlapping peptides derived from the antigen are systematically screened for binding to a binding member. The peptides can be covalently coupled to a support surface to form an array of peptides. Peptides can be in a linear or constrained conformation. A constrained conformation can be produced using peptides having a terminal cysteine (cys) residue at each end of the peptide sequence. The cys residues can be covalently coupled directly or indirectly to a support surface such that the peptide is held in a looped conformation. Accordingly, a peptide used in the method may have a cys residue added to each end of a peptide sequence corresponding to a fragment of the antigen. Double looped peptides can also be used, in which a cys residue is additionally located at or near the middle of the peptide sequence. The cys residues can be covalently coupled directly or indirectly to a support surface such that the peptides form a double-looped conformation, with one loop on each side of the central cys residue. Peptides can be synthetically generated, and cys residues can therefore be engineered at desired locations, despite not occurring naturally in the IL-6 site II sequence. Optionally, linear and constrained peptides can both be screened in a peptide-binding assay. A peptide-binding scan may involve identifying (e.g., using an ELISA) a set of peptides to which the binding member binds, wherein the peptides have amino acid sequences corresponding to fragments of an IL-6a (e.g., peptides that include about 5, 10, or 15 contiguous residues of an IL-6a), and aligning the peptides in order to determine a footprint of residues bound by the binding member, where the footprint comprises residues common to overlapping peptides. Alternatively or additionally the peptide-binding scan method can be used to identify peptides to which the IL-6a binds with at least a selected signal:noise ratio.

Other methods known in the art can be used to determine the residues bound by an antibody, and/or to confirm peptide-binding scan results, including for example, site directed mutagenesis (e.g., as described herein), hydrogen deuterium exchange, mass spectrometry, NMR, and X-ray crystallography.

Typically, an IL-6a useful as described herein is a human antibody molecule, a humanized antibody molecule, or binding fragment thereof. In general, the antibody is a monoclonal antibody. The origin of such an antibody can be human, murine, rat, camelid, rabbit, ovine, porcine, or bovine and can be generated according to methods known to those in the art.

In general, an IL-6a comprises at least the CDRs of an antibody that can specifically bind to an IL-6 (e.g., a human IL-6), e.g., to site II of an IL-6. The structure for carrying a CDR or a set of CDRs of the invention can be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains can be determined by reference to Kabat, et al., 1983 (National Institutes of Health), and updates thereof findable under "Kabat" using any internet search engine.

An IL-6a, as disclosed herein, is typically an antibody that generally comprises an antibody VH domain and/or VL domain. A VH domain comprises a set of heavy chain CDRs (VHCDRs), and a VL domain comprises a set of light chain CDRs (VLCDRs). Examples of such CDRS are provided herein in the Examples. An antibody molecule can comprise an antibody VH domain comprising a VHCDR1, VHCDR2 and VHCDR3 and a framework. It can alternatively or also comprise an antibody VL domain comprising a VLCDR1, VLCDR2 and VLCDR3 and a framework.

Disclosed herein are IL-6 antagonists comprising a VHCDR1 and/or VHCDR2 and/or VHCDR3 such as those disclosed herein and/or a VLCDR1 and/or VLCDR2 and/or VLCDR3 such as those disclosed herein. The IL-6a can comprise one or more CDRs of any of the antibodies, fragments or derivatives described herein. The IL-6a can comprise a set of VHCDRs (e.g., VHCDR1, VHCDR2, and VHCDR3), and optionally it can also comprise a set of VLCDRs (e.g., VLCDR1, VLCDR2, and VLCDR3). The CDRs can be derived from one or more antibodies, fragments, or derivatives described herein. For example, the VLCDRs can be derived from the same or a different antibody as the VHCDRs.

In general, a VH domain is paired with a VL domain to provide an antibody antigen-binding site. For example, the HC domain of SEQ ID NO:1 or SEQ ID NO:3 is paired with the LC domain of SEQ ID NO:2. In some cases, a VH or VL domain alone can be used as an IL-6a.

In some aspects, the IL-6a is an antibody molecule, fragment, or derivative thereof that comprises (i) a VH domain sequence that has at least 60, 70, 80, 85, 90, 95, 98 or 99% amino acid sequence identity with a VH domain described herein (e.g., SEQ ID NO:37), or (ii) a set of VHCDRs (e.g., VHCDR1, VHCDR2, and/or VHCDR3) from the VH domain sequence. In embodiments, the antibody molecule, fragment, or derivative thereof comprises a VHCDR1, VHCDR2, and VHCDR3 of SEQ ID NO:37. In embodiments, the antibody molecule, fragment, or derivative thereof comprises a VHCDR1, VHCDR2, and VHCDR3 that collectively differ from the VHCDR1, VHCDR2, and VHCDR3 of SEQ ID NO:37 by no more than 1, no more than 2, no more than 3, no more than 4, or no more than 5 amino acids.

The antibody molecule, fragment, or derivative thereof can optionally also comprise (i) a VL domain sequence that has at least 60, 70, 80, 85, 90, 95, 98 or 99% amino acid sequence identity with a VL domain described herein, e.g., a VL domain of SEQ ID NO: 38, or (ii) a set of VLCDRs (e.g., VLCDR1, VLCDR2, and/or VLCDR3) from the VL domain. In embodiments, the antibody molecule, fragment or derivative thereof comprises VLCDR1, VLCDR2, and VLCDR3 of SEQ ID NO: 38. In embodiments, the antibody molecule, fragment, or derivative comprises a VLCDR1, VLCDR2, and VLCDR3 that collectively differ from the VLCDR1, VLCDR2, and VLCDR3 of SEQ ID NO:38 by no more than 1, no more than 2, no more than 3, no more than 4, or no more than 5 amino acids. Algorithms that can be used to calculate percent identity of two amino acid sequences include e.g., BLAST, FASTA, or the Smith-Waterman algorithm, e.g., employing default parameters.

An IL-6a as described herein can comprise antibody constant regions or parts thereof, e.g., human antibody constant regions or parts thereof. For example, a VL domain may be attached at its C-terminal end to antibody light chain constant domains including human CK or CL chains. Similarly, an IL-6a based on a VH domain can be attached at its C-terminal end to all or part (e.g., a CH1 domain) of an immunoglobulin heavy chain derived from any antibody isotype, e.g. IgG, IgA, IgE and IgM and any of the isotype sub-classes, particularly IgG1, IgG2, IgG3 and IgG4. In embodiments, the antibody or antigen binding fragment is engineered to reduce or eliminate ADCC activity.

In an embodiment, the antibody of the invention is an IgG2 antibody. In an embodiment, the antibody of the invention comprises an IgG2 framework, IgG2 constant region, or IgG2 Fc region as described herein.

IgG2 antibodies can exist as three major structural isoforms: IgG2-A, IgG2-B, and IgG2-A/B (Wypych J. et al. *Journal of Biological Chemistry.* 2008, 283:16194-16205). This structural heterogeneity is due to different configurations of the disulfide bonds that link the Fab arms to the heavy chain hinge region. In the IgG2-A isoform, there are no disulfide bonds linking the Fab arms to the hinge region.

In the IgG2-B isoform, both Fab arms have disulfide bonds linking the heavy and light chain to the hinge region. The IgG2-A/B isoform is a hybrid between the IgG2-A and IgG2-B isoforms, with only one Fab arm having disulfide bonds linking the heavy and light chain of the one Fab arm to the hinge region. The conversion of an IgG2 antibody between two or all of the different structural isoforms, also referred to as disulfide shuffling, occurs naturally in vivo and in vitro for both naturally-occurring and recombinant antibodies. As a result, formulations of IgG2 antibodies in the art comprise a heterogeneous mixture of IgG2-A, IgG2-B, and IgG2-A/B isoforms. The different IgG2 isoforms can have unique and different functional properties, such as differences in stability, aggregation, viscosity, Fc receptor binding, or potency. Presence of multiple isoforms or increased levels of a particular isoform in a IgG2 antibody formulation can negatively affect stability, aggregation, or potency.

The present invention provides an antibody with the advantage of primarily existing in the IgG2-A or IgG2-A/B isoform. The antibody of the present invention does not exist in the IgG2-B isoform, or does not exist in the IgG2-B isoform for a substantial amount of time. Thus, compositions and formulations comprising the antibody of the invention are less heterogeneous than other IgG2 antibodies known in the art, and therefore, more preferred for use in a therapeutic application.

Compositions comprising the antibody of the invention comprise primarily IgG2-A and/or IgG2-A/B isoforms of the antibody. In an embodiment, a composition comprising an antibody described herein comprises at least 50, 60, 70, 80, 90, 95, 96, 97, 98, or 99% of the IgG2-A or IgG2-A/B isoforms of the antibody. In an embodiment, a composition comprising an antibody described herein comprises at least 60, 70, 80, 90, 95, 96, 97, 98, or 99% of the IgG2-A and IgG2-AB isoforms collectively. In such embodiments, a composition comprising an antibody described herein does not comprise a substantial amount of the IgG2-B isoforms of the antibody. For example, the composition comprises less than 10%, 5%, 2%, 1%, 0.5%, or 0.1% of the IgG2-B isoforms of the antibody.

In some cases, an antibody of the invention is further modified using methods known in the art create a sequence having a specific allotype, for example an allotype that predominates in a population having a particular geographic origin. In some cases, the human heavy chain constant region is modified for this purpose.

An IL-6a can be an antibody molecule, binding fragment thereof, or variant, having one or more CDRs, for example, a set of CDRs, within an antibody framework. For example, one or more CDRs or a set of CDRs of an antibody (e.g., an antibody or fragment or derivative thereof as described herein) may be grafted into a framework (e.g., human framework) to provide an antibody molecule. The framework regions can be derived from human germline gene sequences, or be non-germline in origin.

VH and/or VL framework residues can be modified as discussed and exemplified herein e.g., using site-directed mutagenesis.

Amino acid changes can be made in one or more framework regions and/or one or more CDRs derived from an antibody IL-6a targeted to site II of IL-6 (termed herein a "reference IL-6 antibody") using methods and parameters known in the art. Also included herein is a resulting IL-6 antagonist that retains binding to site II of an IL-6 (e.g., site II of a human IL-6) and typically has at least the same binding or increased affinity compared to the reference IL-6 antibody. In some cases, to improve a parameter such as stability, a change that results in a decrease in binding affinity of the derived IL-6a compared to the reference IL-6a (e.g., the reference antibody) can be introduced to create a useful IL-6a. In some embodiments, e.g., in some cases in which the reference relates to FcRn binding or a pharmacokinetic (PK) parameter such as half-life in the vitreous or systemic half-life (e.g., in blood, plasma, serum, lymph, liver, kidney, other tissue, or body fluid), a reference antibody may be an antibody that does not specifically bind an IL-6.

A change in the amino acid sequence of an IL-6a polypeptide can include substituting one or more amino acid residue(s) with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, and N-acetylserine. Those amino acid residues that are derivatized at their N-alpha position will only be located at the N-terminus of an amino-acid sequence. The amino acid is typically an L-amino acid. In some cases the amino acid is a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention can comprise non-natural or non-standard amino acids as discussed herein. Non-standard amino acids (e.g., D-amino acids) can be incorporated into an amino acid sequence using methods known in the art, for example in synthesis of the molecule or by post-synthesis modification or replacement of an amino acid. In some cases, a D-amino acid is used to increase PK of an IL-6a.

Novel VH or VL regions carrying CDR-derived sequences of the invention may be generated using random mutagenesis of one or more selected VH and/or VL nucleic acid sequences to generate mutations within the entire variable domain. For example, error-prone PCR can be used (Chao et al., Nature Protocols, 1:755-768 (2006)). In some embodiments one or two amino acid substitutions are made within an entire variable domain or set of CDRs. Other methods know in the art can be used to generate mutations, for example site-directed mutagenesis, typically in one or more CDRs.

One method for producing an antibody IL-6a, is to alter a VH domain such as those disclosed herein by adding, deleting, substituting or inserting one or more amino acids. The altered VH domain can be combined with a VL domain (e.g., a VL domain disclosed herein), which can also be altered as described herein and using methods known in the art. Such altered molecules are tested for their ability to bind to site II of IL-6 and optionally for other desired properties such as increased affinity compared to a reference molecule.

In some cases, a variant VH or VL domain can have 1, 2, 3, 4, or 5 such alterations (e.g., 1, 2, 3, 4, or 5 amino acid substitutions).

In embodiments, an IL-6a of the invention is a fragment of an antibody that binds to site II of an IL-6 and comprises an antigen binding site, e.g., can bind to site II of an IL-6. Antibody fragments of the invention are generally obtained starting with a reference (parent) antibody molecule, such as an antibody molecule comprising SEQ ID NO:41 and SEQ ID NO:42. Antibody fragments can be generated using methods known in the art such as recombinant DNA, enzymatic cleavage (for example, using pepsin or papain), chemical cleavage of an antibody (for example, chemical reduction of disulfide bridges). Antibody fragments that comprise an antibody antigen-binding site include, but are not limited to, molecules such as Fab, Fab', Fab'-SH, scFv, Fv, dAb, Fd, and disulfide stabilized variable region (dsFv). Various other antibody molecules including one or more antibody antigen-binding sites can be engineered, including for example F(ab')2, F(ab)3, diabodies, triabodies, tetrabodies, and minibodies. Examples of antibody molecules and methods for their construction and use are described in Holliger and Hudson, 2005, Nat Biotechnol 23:1126-1136. Non-limiting examples of binding fragments are a Fab fragment composed of VL, VH, constant light chain domain (CL) and constant heavy chain domain 1 (CH1) domains; an Fd fragment composed of VH and CH1 domains; an Fv fragment composed of the VL and VH domains of a single antibody; a dAb fragment composed of a VH or a VL domain; isolated CDR regions; an F(ab')2 fragment, a bivalent fragment comprising two linked Fab fragments; a single chain Fv molecule (scFv), in which a VH domain and a VL domain are linked by a peptide linker which allows the two domains to associate to form an antigen binding site; a bispecific single chain Fv dimer (for example as disclosed in WO 1993/011161) and a diabody, which is a multivalent or multispecific fragment constructed using gene fusion (for example as disclosed in WO94/13804). Fv, scFv, or diabody molecules can be stabilized by the incorporation of disulfide bridges linking the VH and VL domains. Minibodies comprising an scFv joined to a CH3 domain can also be used as an IL-6a. Other fragments and derivatives of an antibody that can be used as an IL-6a include a Fab', which differs from a Fab fragment by the addition of a few amino acid residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

In some cases, an IL-6a that is an antibody fragment has been chemically modified to improve or introduce a desirable property, for example PEGylation to increase half-life or incorporation.

A dAb (domain antibody) is a small monomeric antigen-binding fragment of an antibody (the variable region of an antibody heavy or light chain. VH dAbs occur naturally in camelids (e.g., camels and llamas) and can be produced by immunizing a camelid with a target antigen, isolating antigen-specific B cells and directly cloning dAb genes from individual B cells. An IL-6a of the present invention can be a dAb comprising a VH or VL domain substantially as set out herein, or a VH or VL domain comprising a set of CDRs substantially as set out herein.

Antibodies of the invention include bispecific antibodies in which two different variable regions are combined in the same molecule. An Il-6a can be incorporated as part of a bispecific antibody prepared using methods known in the art, for example, prepared chemically or from hybrid hybridomas. Such a molecule can be a bispecific antibody fragment of a type discussed above. One non-limiting example of a method for generating a bispecific antibody is BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, are useful, in part because they can be constructed and expressed in *E. coli*. Diabodies (and many other polypeptides, such as antibody fragments) of appropriate binding specificities can be readily selected using phage display (WO 1994/13804) from libraries. If one arm of the diabody is to be kept constant, for example, with a specificity directed against site II of IL-6, then a library can be made where the other arm is varied and an antibody of appropriate specificity selected.

Bispecific whole antibodies may be made by alternative engineering methods as described in described in WO 1996/27011, WO 1998/50431 and WO 2006/028936.

In some cases, an IL-6a of the invention comprises an antigen-binding site within a non-antibody molecule, for example, by incorporating one or more CDRs, e.g. a set of CDRs, in a non-antibody protein scaffold, as discussed further below. In some cases, the CDRs are incorporated into a non-antibody scaffold. An IL-6 site II binding site can be provided by an arrangement of CDRs on non-antibody protein scaffolds, such as fibronectin or cytochrome B, or by randomizing or mutating amino acid residues of a loop within a protein scaffold to confer binding specificity for an IL-6 site II. Scaffolds for engineering novel binding sites in proteins are known in the art. For example, protein scaffolds for antibody mimics are disclosed in WO200034784, which describes proteins (antibody mimics) that include a fibronectin type III domain having at least one randomized loop. A suitable scaffold into which to graft one or more CDRs, e.g., a set of HCDRs, can be provided by any domain member of the immunoglobulin gene superfamily. The scaffold can be a human or non-human protein. An advantage of a non-antibody protein scaffold is that it can provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g., using the 10th fibronectin type III domain), lipocalins as well as gamma-crystalline and other Affilin™ scaffolds (Scil Proteins, Halle, Germany). Examples of other approaches include synthetic microbodies based on cyclotides—small proteins having intra-molecular disulfide bonds, microproteins (e.g., Versabodies™, Amunix Inc., Mountain View, Calif.) and ankyrin repeat proteins (DARPins, e.g., from Molecular Partners AG, Zurich-Schlieren, Switzerland). Such proteins also include small, engineered protein domains such as, for example, immuno-domains (see for example, U.S. Patent Publication Nos. 2003/082630 and 2003/157561). Immuno-domains contain at least one complementarity determining region (CDR) of an antibody.

An IL-6a can comprise additional amino acids, e.g., to impart to the molecule another functional characteristic in addition to ability to bind antigen.

In some cases, an IL-6a carries a detectable label, or is conjugated to a toxin or a targeting moiety or enzyme (e.g., via a peptidyl bond or linker). For example, an IL-6a can comprise a catalytic site (e.g., in an enzyme domain) as well as an antigen binding site (e.g., binding site for site II of an IL-6), such that the antigen binding site binds to the antigen and thus targets the catalytic site to IL-6 or IL-6/IL-6R complex. The catalytic site can, in some cases, further inhibit a biological function of an IL-6, e.g., by cleavage of the IL-6, IL-6R, or other molecule that is associated with the IL-6a/IL-6 complex.

In some aspects, the invention includes an antibody IL-6a that has been modified compared to a reference antibody to alter, for example, increase, decrease, or eliminate, the biological effect function of the IL-6a. In one example, the Fc region is modified or the parental Fc domain is replaced with a modified Fc domain to alter the pharmacokinetics of the modified IL-6a compared to the unmodified parent. In some embodiments, the IL-6a is engineered to have an IgG2 framework. In other embodiments, the IL-6a is in an IgG1 or IgG2 framework and has a modified Fc that increases the binding affinity of the IL-6a at pH 6.0 and does not substantially alter the binding affinity at pH 7.0 compared to a parent or other reference IL-6a. In embodiments, the Fc domain is modified and the IL-6a has reduced systemic accumulation, a decreased half-life, and/or increased systemic clearance compared to a parent or other reference IL-6a.

In some embodiments, an antibody IL-6a is modified to increase complement fixation and complement-dependent cytotoxicity. In other aspects, the antibody IL-6a is modified to increase the ability of the antibody compared to a reference antibody to activate effector cells and participate in antibody-dependent cytotoxicity (ADCC). In some cases, the antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the antibodies disclosed herein are modified to reduce their ability to fix complement and participate in complement-dependent cytotoxicity (CDC). In other embodiments, the antibodies are modified to reduce their ability to activate effector cells and participate in antibody-dependent cytotoxicity (ADCC). In yet other embodiments, an antibody as disclosed herein can be modified both to reduce its ability to activate effector cells and participate in antibody-dependent cytotoxicity (ADCC) and to reduce its ability to fix complement and participate in complement-dependent cytotoxicity (CDC).

It is generally advantageous to avoid frequent delivery of a dose of an IL-6a, for example, when delivered by injection into the eye. To facilitate this feature, in certain embodiments, the half-life at the site of delivery, e.g., the vitreous, of an IL-6a as disclosed herein is at least 4 days, for example, at least 7 days, at least 9 days, at least 11 days, or at least 14 days. In certain embodiments, the mean half-life of an IL-6a is at least 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 25 days, 30 days, 40 days, 50 days, or 60 days. Methods of increasing the half-life of an antibody are known in the art, for example as described in U.S. Pat. No. 6,277,375 and International Publication Nos. WO 1998/23289 and WO 1997/3461. In some embodiments, the half-life of an IL-6a is greater at the target delivery site, e.g., the vitreous, than systemic half-life, e.g., half-life in blood, serum, plasma, lymph, liver, kidney, or other tissue or body fluid.

In another embodiment, the invention provides an article of manufacture including a container. The container includes a composition containing an IL-6a as disclosed herein, and a package insert or label indicating that the composition can be used to treat an IL-6 related disorder. Typically, the composition is an IL-6a in a composition comprising a pharmaceutically acceptable excipient.

In some cases, the invention is a kit comprising a composition containing an IL-6a as disclosed herein, and instructions to administer the composition to a subject in need of treatment.

In embodiments in which a large IL-6a is desirable, e.g., to enhance retention of the IL-6a at or near its site of delivery, a moiety that increases size but does not significantly adversely affect function of the IL-6a (e.g., binding affinity of the IL-6 for IL-6 or IL-6/IL-6R complex) can be associated with the Il-6a. For example, a Fab can be genetically engineered to be expressed as single polypeptides containing a Fab and an Fc moiety.

In embodiments in which a relatively small size for the IL-6a is desirable, fragments of an IL-6 antibody can be used, for example, an scFv or a Fab fragment. An IgG antibody is about 150 kD in size, a Fab is about 50 kD and an scFv is about 25 kD. In some embodiments, an IL-6a as described herein is less than about 50 kD in size. Such an antagonist can be, for example, less than or equal to 50 kD and greater than 10 kD, less than or equal to 50 kD and greater than 20 kD, or less than or equal to 50 kD and greater than or equal to 25 kD.

In some cases, stability of an IL-6 antagonist, e.g., an antibody or other inhibitor having disulfides, is improved by creating variant in which one or more of the disulfide bridges are more stable than in the parent molecule.

Another advantage of certain IL-6a molecules described herein can be the availability of effective molecules having a size suitable for their mode of delivery, site of delivery, or mode of activity. For example, an IL-6a in a Fab format may be used for a topical application. Methods of engineering such molecules are described herein and are known in the art.

Indications/IL-6 Associated Disease

Diseases that can be treated with an IL-6a of the invention include those diseases in which elevated IL-6 is associated with the disease state or as a prerequisite to the disease state. Such diseases include those in which angiogenesis and inflammation driven by IL-6 contribute to disease pathology. This includes diseases in which IL-6 is elevated compared to normal levels, e.g., diseases in which IL-6 is elevated in the vitreous (such as, e.g., diabetic macular edema, diabetic retinopathy, and uveitis) or tissues of the eye. Examples include certain eye diseases including, without limitation, dry eye (e.g., dry eye disease or dry eye syndrome), allergic conjunctivitis, uveitis, age-related macular degeneration (AMD), proliferative diabetic retinopathy (PDR), diabetic macular edema (DME), Rhegmatogenous retinal detachment (RRD), retinal vein occlusion (RVO), neuromyelitis optica (NMO). Other ocular disorders that can be treated include those caused by trauma such as corneal transplant, corneal abrasion, or other such physical injury to the eye. Accordingly, the invention includes treating a subject having an IL-6 related disease with an IL-6a described herein.

In some embodiments, the IL-6 associated disease is an inflammatory disease. In some embodiments, the disease is glaucoma.

In some embodiments, the disease is ocular pain.

In some embodiments, treatment of a subject also includes determining whether the subject has an IL-6 associated disease, and optionally, whether the subject is resistant to other non-IL-6 inhibitory treatments such as steroids or anti-VEGF therapeutics.

One problem with certain antibody-based therapeutics that are effective at a specific locus such as the eye, for example in the vitreous, is adverse effects that result from systemic administration. One solution is to provide therapeutics that can be delivered locally as opposed to systemically as exemplified by molecules described herein. Because some therapeutics that are locally delivered, e.g., to the vitreous, will, to some extent, appear systemically, it is advantageous to design a molecule that will have relatively rapid systemic turnover. Applicants have engineered examples of IL-6 antibodies designed for rapid systemic turnover, e.g., compared to the parental molecule or a reference antibody. This was accomplished by mutating the Fc domain to modify FcRn binding of the molecule, e.g., to reduce FcRn mediated recycling of the IL-6a.

Diabetic macular edema (DME). Diabetic macular edema (DME) involves occlusion and leakage of retinal blood vessels, causing reduced visual acuity and potentially blindness. Standard treatments for DME include local administration of steroids or anti-VEGF antibodies. However, many patients are refractory to these therapies. The pathogenesis of diabetic macular edema involves components of angiogenesis, inflammation, and oxidative stress. IL-6 is induced by hypoxia and hyperglycemia and can increase vascular inflammation, vascular permeability, and pathologic angiogenesis. IL-6 can directly induce VEGF expression and can promote choroidal neovascularization in animal models. In DME patients, ocular IL-6 levels are positively correlated with macular thickness and disease severity. IL-6 levels are reportedly elevated in patients who fail anti-VEGF therapy while decreasing in anti-VEGF responsive patients. Accordingly, administration of an IL-6a as described herein is useful for treatment of diabetics in combination with an anti-VEGF therapeutic or as an alternative to anti-VEGF treatment, including for patients who do not respond to anti-VEGF therapy. Treatment of macular edema with an IL-6a may also improve safety by removing the need to completely inhibit either mechanism to inhibit the pathology, thus preserving some of the desired, physiological roles of each cytokine. Accordingly, local IL-6a treatment in combination with VEGF inhibition can decrease the dose frequency and reduce adverse effects of treatment.

In DME there are positive correlations between vitreal IL-6 levels and both disease severity and VEGF refractory subjects. Accordingly, an IL-6a as described herein can be used to treat DME subjects who are refractive to steroid therapy, anti-VEGF therapy, or both. In some cases, an IL-6a is used in combination with anti-VEGF therapy or steroid therapy, e.g., to treat DME.

An IL-6a described herein can also be used to treat disorders such as cancer, e.g., prostate cancer, leukemia, multiple myeloma, inflammatory (such as chronic inflammatory proliferative diseases) and autoimmune disease, e.g., rheumatoid arthritis, Castleman's disease (giant or angiofollicular lymph node hyperplasia, lymphoid hamartoma, angiofollicular lymph node hyperplasia), juvenile idiopathic arthritis (including polyarticular juvenile idiopathic arthritis and systemic juvenile idiopathic arthritis), Still's disease (encompassing juvenile idiopathic arthritis and adult onset Still's disease), adult onset Still's disease, amyloid A amyloidosis, polymyalgia rheumatica, remitting seronegative symmetrical synovitis with pitting edema, spondyloarthritides, Behçet's disease (including treatment of ocular manifestations), atherosclerosis, psoriasis, systemic lupus erythematosis, polymyositis (an inflammatory myopathy), relapsing polychondritis, acquired hemophilia A, multiple sclerosis, anemia of inflammation, and Crohn's disease.

IL-6 antagonists are also useful for treatment of certain neurologic diseases, for example, depression, and Alzheimer's disease.

Other diseases that can be treated with an IL-6a described herein include, without limitation, systemic sclerosis, Takayasu arteritis, giant cell arteritis, graft versus host disease, and TNF-receptor-associated periodic syndrome (TRAPS).

Dosing

An IL-6 antibody or fragment thereof can be administered to a subject (e.g., a patient) who expresses, e.g., abnormally high levels of IL-6. The antibody or fragment thereof can be administered once, or can be administered multiple times. The antibody may be administered, for example, from three times daily to once every six months or longer. The administration can be on a schedule such as three times daily, twice daily, once daily, once every two days, once every three days, once weekly, once every two weeks, once every month, once every two months, once every three months and once every six months. The antibody or fragment thereof can be administered continuously via a minipump or other route such as an implantable slow-release capsule or by an encapsulated cell producing the antibody or fragment thereof. The antibody or fragment thereof can be administered via a mucosal, buccal, intranasal, inhalable, intravenous, subcutaneous, intramuscular, parenteral, intraocular, or intratumor route. The antibody or fragment thereof can be administered once, at least twice or for at least the period of time until the condition is treated, palliated or cured. The antibody or fragment thereof generally will be administered for as long as the condition is present. The antibody or fragment thereof, it will generally be administered as part of a pharmaceutical composition as described herein. The dosage of antibody will generally be in the range of 0.1 to 100 mg/kg, 0.5 to 50 mg/kg, 1 to 20 mg/kg, and 1 to 10 mg/kg. The serum concentration of the antibody or fragment thereof can be measured by any suitable method. One feature of certain compounds described herein is that they require relatively infrequent dosing, for example, once per week, twice per week, three times per week, once every four weeks, once every two weeks, once every 8 weeks, once every 12 weeks, once every 16 weeks, once every 32 weeks, once per month, once per two months, once per three months, or once per six months. In some cases the compound is administered on an as needed basis, determined, for example by a subject's condition. It is a feature of the IL-6 antagonists described herein that permits relatively infrequent dosing is the combination of high potency which is accomplished, at least in part, by a slow off rate once bound to an IL-6 and the ability to deliver a relatively high concentration of the compound.

In some cases, the IL-6a is administered as a monotherapy. In other embodiments, the IL-6a is administered concomitantly with methotrexate or other disease modifying anti-arthritic drug.

Generation of Antibodies

An antibody IL-6a or derivative or fragment thereof can be produced using methods known in the art such as monoclonal antibody methodology (e.g., see Kohler and Milstein (1975) Nature 256: 495). Other techniques for producing monoclonal antibodies can also be employed such as viral or oncogenic transformation of B lymphocytes.

Chimeric or humanized antibodies can be prepared based on the sequence of a murine monoclonal antibody prepared using methods known in the art. DNA encoding the heavy and light chain immunoglobulins can be obtained from a murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567). To create a humanized antibody, the murine CDR regions can be inserted into a human framework using methods known in the art (see e.g., U.S. Pat. Nos. 5,225,539, and 5,530,101; 5,585,089; 5,693,762; and 6,180,370).

In embodiments, an IL-6a described herein (e.g., an anti-IL-6 antibody or derivative or fragment thereof) can specifically bind human IL-6. In embodiments, the IL-6a can specifically bind to site II of IL-6 (e.g., site II of human IL-6).

In some embodiments, an IL-6a antibody is a human monoclonal antibody. Such antibodies can be generated using transgenic or transchromosomic mice comprising portions of a human immune system rather than the mouse system. These transgenic and transchromosomic mice include "human Ig mice" such as the HuMAb Mouse® and KM Mouse® (See, e.g., U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; PCT Publication Nos.: WO 92/03918, WO 93/12227, WO 94/25585, WO 97/13852, WO 98/24884 and WO 99/45962; and PCT Publication No. WO 01/14424).

In another aspect, human anti-IL-6 antibodies can be raised using a mouse that carries human immunoglobulin sequences on transgenes and transchomosomes, such as a mouse that carries a human heavy chain transgene and a human light chain transchromosome. Such mice are described in detail in PCT Publication No. WO 02/43478.

Other transgenic animal systems expressing human immunoglobulin genes are available in the art and can be used to raise an antibody IL-6a. For example, an alternative transgenic system referred to as the Xenomouse™ (Abgenix, Inc.) can be used; such mice are described in, for example, U.S. Pat. Nos. 5,939,598; 6,075,181; 6,114,598; 6,150,584; and 6,162,963. Moreover, transchromosomic animal systems expressing human immunoglobulin genes are available in the art and can be used to raise an antibody IL-6a. For example, mice carrying both a human heavy chain transchromosome and a human light chain transchromosome are described in Tomizuka et al. (2000, Proc Natl Acad Sci USA 97:722-727). Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767.

Phage Display Libraries

In some cases, an antibody IL-6a antibody or derivative or fragment thereof is produced in a method that involves synthesizing a library of human antibodies using phage, screening the library with an IL-6, e.g., a human IL-6, or a fragment thereof, isolating phage that bind IL-6, and obtaining the antibody from the phage.

Recombinant human antibody IL-6a can also be isolated by screening a recombinant combinatorial antibody library. In general, the library is a scFv phage display library, generated using human VL and VH cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). Other methods and reagents that can be used in generating and screening antibody display libraries are known in the art (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum Antibod Hybridomas 3:81-85 (1992); Huse et al., Science 246:1275-1281 (1989); McCafferty et al., Nature 348:552-554 (1990); Griffiths et al., EMBO J 12:725-734 (1993); Hawkins et al., J Mol Biol 226:889-896 (1992); Clackson et al., Nature 352:624-628 (1991); Gram et al., Proc Natl Acad Sci USA 89:3576-3580 (1992); Garrad et al., Bio/Technology 9:1373-1377 (1991); Hoogenboom et al., Nuc Acid Res 19:4133-4137 (1991); and Barbas et al., Proc Natl Acad Sci USA 88:7978-7982 (1991), all incorporated herein by reference.

In an example for isolating and producing human IL-6 antibodies with the desired characteristics, a human IL-6 antibody is first used to select human heavy and light chain sequences having similar binding activity toward IL-6, using epitope imprinting methods described in PCT Publication No. WO 93/06213, incorporated herein by reference. The antibody libraries used in this method are generally scFv libraries prepared and screened as described in PCT Publication No. WO 92/01047; McCafferty et al., Nature 348: 552-554 (1990); and Griffiths et al., EMBO J 12:725-734 (1993), all incorporated herein by reference.

Once initial human VL and VH domains are selected, "mix and match" experiments are performed, in which different pairs of the initially selected VL and VH segments are screened for IL-6 binding to select preferred VL/VH pair combinations. To select for desirable features of an IL-6a, the VL and/or VH segments of a selected pair can be randomly mutated. This in vitro affinity maturation can be accomplished, for example, by amplifying VH and VL domains using PCR primers complimentary to a CDR of one or both of the selected VH and VL domains, which primers contain a random mixture of the four nucleotide bases at certain positions such that the resultant PCR products encode VH and VL segments into which random mutations have been introduced into the VH and/or VL. Such randomly mutated VH and VL segments can be re-screened for binding to IL-6, e.g., to site II of IL-6.

Following screening and isolation of an antibody IL-6a from a recombinant immunoglobulin display library, nucleic acids encoding the selected antibody can be recovered from the display package (e.g., from the phage genome) and subcloned into other expression vectors using recombinant DNA techniques known in the art. Such antibodies can be further manipulated to produce an antibody fragment such as those described herein.

Pharmacokinetics (PK)

Testing for PK can be performed using methods described herein and/or methods known in the art. One barrier to determinations requiring the use of an animal, for example determination of PK, is that human IL-6 has less than 50% homology with that of some animals commonly used for such testing. One method of testing PK is therefore to use a transgenic mouse expressing human IL-6. In some embodiments, a non-human primate is used to determine PK.

In some embodiments, an anti-IL6 antibody is mutated to alter its PK, e.g., by altering the pH sensitivity of FcRn binding. A method of obtaining such mutations is described in the Examples. Accordingly, in some embodiments, the IL-6a has altered systemic PK compared to a parental IL-6a or a reference molecule. In some cases, the PK is not altered or is improved in the vitreous. In some embodiments, the IL-6a has reduced systemic PK (e.g., decreased half life and/or increased clearance, e.g., as assayed in a circulatory fluid such as blood, plasma, lymph, or serum) compared to a parental IL-6a or a reference molecule.

Models for Testing an IL-6 Antagonist

IL-6 antagonists can be tested in models of disease for IL-6 associated delivery, particularly for the efficacy of treatment and limited deleterious effects on advantageous IL-6 properties. For example, uveitis can be tested in an experimental autoimmune uveitis model in rats or mice (Caspi, Invest Ophthalmol Vis Sci 52:1873; Agarwal et al., 900:443-69, 2012) using interphotoreceptor retinoid-binding protein (IRBP) in complete Freund's adjuvant (CFA) immunization. Other models include those known in the art for dendritic cell-induced uveitis, adoptive transfer of cultured effector T cells, spontaneous EAU in IRBP TCR Tg mice, endotoxin-induced uveitis, autoimmune uveoretinitis (Haruta et al., Invest Ophthalmol Vis Sci 53:3264 (2011); Yoshimura et al., Rheumatology 48:347-354 (2009)).

Other model systems that can be used to examine the effects of an IL-6a in the treatment of IL-6 associated disease are, for example, a choroidal neovascularization (CNV) model (Izumi-Nagai et al., Am J Pathol 170:6 (2007); Krzystolik et al., Arch Ophthalmol 120:338 (2002)) and diabetic models such as those described in Kern et al. (Animal Models Of Diabetic Complications Consortium (P01 DK57733), Update Report (September 2001-January 2004)). Animal models useful for testing an IL-6a in rheumatoid arthritis are known in the art, e.g., see Asquith et al. (Eur J Immunol 39:2040-4 (2009)) and Kollias et al. (Ann Rheum Dis 70:1357-62 (2011).

CNV models are representative, e.g., of the human conditions of AMD and DME. Retinal neovascularization models are useful, e.g., for studying ischemic retinopathies, e.g., diabetic retinopathy or retinopathy of prematurity. Various choroidal and retinal neovascularization models are known in the art (see, e.g., Grossniklaus, H. E. et al. Prog Retin Eye Res. 2010 November; 29(6):500-19. doi: 10.1016/j.preteyeres.2010.05.003. Epub 2010 May 19; Saisin, Y et al. (2003) Journal of Cellular Physiology, 195:241-248; Takahashi, K. et al. (2003) Investigative Ophthalmology & Visual Science, 44(1):409-415; Lima e Silva, R. et al. (2007) FASEB Journal, 21:3219-3230; Tobe et al. (1998) American Journal of Pathology, 153(5):1641-1646; Dong, A et al. (2011) PNAS, 108(35): 14614-14619; Dong et al. (2009) J Cell Physiol 219:544-552; Smith, L E et al. 1994 Invest Ophthalmol Vis Sci 1994; 35:101-111; Shen, J. et al. (2007) Investigative Ophthalmology & Visual Science, 48(9):4335-4341) and can be used to investigate the efficacy of an IL-6a. Choroidal neovascularization (CNV) can be induced, e.g., by lasers, light, surgery, or genetic modifications. Models of oxygen-induced retinal neovascularization are known in the art and are described, e.g., in Smith, L E et al. 1994 Invest Ophthalmol Vis Sci 1994; 35:101-111; Shen, J. et al. (2007) Investigative Ophthalmology & Visual Science, 48(9):4335-4341.

An ischemia/reperfusion model can also be used. See, e.g., Zheng, L et al. Investigative Ophthalmology & Visual Science, vol. 48 no. 1 pp. 361-367, 2007. For example, on Day 1, a 30 gauge needle attached to a fluid bag is inserted into the cornea of anesthetized mice and the intraocular pressure (IOP) is elevated to approximately 120 mmHg to generate ischemia. After 30-90 minutes, the needle is removed, IOP is normalized, and reflow of the retinal circulation occurs. Expression of inflammatory markers including TNF-α and ICAM-1 can be assessed by western blot and qPCR on Day 2-6. Additionally, ganglion cell loss can be assessed by histology on Day 3-14 and capillary degeneration is measured by trypsin digest technique on Day 10-14. For therapeutic studies, test article (e.g., 1 L of an appropriate concentration, e.g., 20 mg/mL, of an IL6a) is injected intravitreally either shortly before or after the induction of ischemia.

Combination Therapies

In some embodiments, an IL-6a is administered in combination with a second therapeutic entity. For example, an IL-6a is administered in a treatment regime that includes a VEGF inhibitor such as, e.g., ranibizumab. In some embodiments, an IL-6a is administered in a treatment regime that includes a PDGF inhibitor such as, e.g., an anti-PDGF antibody or anti-PDGF receptor antibody (e.g., imatinib). In some embodiments, an IL-6a is administered in combination with a complement pathway inhibitor, e.g., lampalizumab (Factor D inhibitor) or a C5 inhibitor.

Delivery of IL-6 Antagonist

An IL-6 antagonist or composition described herein can be delivered locally, either in direct contact with or near a cell or tissue being targeted for IL-6 inhibition. Non-limiting examples of such delivery methods include injection, infusion, or implantation of a substance containing an IL-6 antagonist.

In embodiments, the IL-6a or composition is administered intraocularly, e.g., intravitreally, e.g., via intravitreal injection, an ophthalmic insert, or genetic delivery.

In some embodiments, the IL-6a composition is administered as an ophthalmic formulation. The methods can comprise administration of the IL-6a composition and an ophthalmically acceptable carrier. In some embodiments, the ophthalmic formulation is a liquid, semi-solid, insert, film, microparticle, or nanoparticle. The IL-6a composition can be administered, e.g., topically or by injection (e.g., intravitreal injection).

In some embodiments, the IL-6a composition is formulated for intravitreal administration.

In some embodiments, the IL-6a composition is formulated for topical administration, e.g., to the eye. The topical formulation can be a liquid formulation or semi-solid, for example, a topical formulation can include an aqueous solution, an aqueous suspension, an ointment or a gel. An ophthalmic IL-6a formulation can be topically applied to the front of the eye, under the upper eyelid, on the lower eyelid and in the cul-de-sac. Typically, the ophthalmic formulation is sterile. An IL-6a ophthalmic formulation can contain one or more pharmaceutical excipients suitable for the preparation of ophthalmic formulations. Examples of such excipients are preserving agents, buffering agents, chelating agents, antioxidant agents and salts for regulating the osmotic pressure. Ophthalmic formulations, including both ointments and suspensions, typically have a viscosity that is suited for the selected route of administration. In some embodiments, the ophthalmic formulation has a viscosity of from about 1,000 to about 30,000 centipoise.

In some embodiments, the formulation is a liquid formulation comprising a polymer. Such a polymer can be used to improve the bioavailability, raise viscosity, or reduce drainage from the eye of a liquid formulation. Suitable polymers include, but are not limited to, those described in Wagh et al. (Asian J Pharm, 2:12-17, 2008). In non-limiting examples, the polymer is sodium hyaluronase, chitosan, a cyclodextrin (e.g., hydroxypropyl-β-cyclodextrin), polygalactoronic acid, xyloglucan, xanthan gum, gellan gum, a thiomer, a poly (ortho ester) (e.g., Einmahl, Adv Drug Deliv Rev 53:45-73, 2001), or a tamarind seed polysaccharide (e.g., Ghelardi et al., Antimicrob Agents Chemother 48:3396-3401, 2004).

In some embodiments, a formulation comprising a IL-6a composition for ophthalmic delivery can comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

In some embodiments, purified or deionized water is used in the composition. The pH can be adjusted by adding any physiologically and ophthalmically acceptable pH adjusting acids, bases or buffers to within the range of about 5.0 to 8.5, e.g., pH 7.0, pH 7.3, pH, 7.4, or pH 7.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Examples of salts and buffers that can be used in a formulation include citrate/dextrose, sodium bicarbonate, ammonium chloride and mixtures of the aforementioned acids and bases.

In some embodiments, the osmotic pressure of the ophthalmic composition may be from about 10 milliosmolar (mOsM) to about 400 mOsM, for example, 200 to 400 mOsM, or 220 to 370 mOsM. Generally, the osmotic pressure can be adjusted using physiologically and ophthalmically acceptable salts or excipients. In some embodiments, sodium chloride is included in a formulation, for example, sodium chloride is present in a formulation in a concentration ranging from 0.01% to 1% by weight, or from 0.05% to 0.45% by weight, based on the total weight of the composition. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the desired range. In some embodiments, a sugar such as mannitol, dextrose, sorbitol, glucose and the like is also used to adjust osmolality.

In some embodiments, the methods involve forming or supplying a depot of the agent in contact with the external surface of the eye. A depot refers to a source of agent that is not rapidly removed by tears or other eye clearance mechanisms. This allows for continued, sustained high concentrations of agent be present in the fluid on the external surface of the eye by a single application. In some embodiments, the depot can remain for up to eight hours or more. In some embodiments, the ophthalmic depot formulation includes, but is not limited to, aqueous polymeric suspensions, ointments, and solid inserts.

In some embodiments, a semi-solid composition is a liquid formulation that increases in viscosity upon application to the eye, typically due to the presence of a polymer in the liquid formulation for which an increase is viscosity occurs with a change in temperature, pH, or electrolyte concentration. The polymer can be, for example, celluloseacetophthalate, polyacrylic acid, gellan gum, hyaluronase, chitosan, salts of alginic acid (e.g., sodium alginate), or a block copolymer of ethylene oxide and propylene oxide (e.g., Pluronic®, BASF; poloxamer). In some embodiment, the polyacrylic acid is cross-linked acrylic acid (e.g., Carbopol®). In some embodiments, the semi-solid composition comprises a mixture of carbopol and a block copolymer of ethylene oxide and propylene oxide; a mixture of methyl cellulose and hydroxyethyl cellulose; or a mixture of polyethylene glycol and a block copolymer of ethylene oxide and propylene oxide.

In some embodiments, the IL-6a containing ophthalmic formulation is an ointment or gel. In some embodiment, the ophthalmic formulation is an oil-based delivery vehicle. For example, the formulation can comprises a petroleum or lanolin base to which the IL-6a composition is added (for example at 0.1 to 2%), and excipients. Common bases can include, but are not limited to, mineral oil, petrolatum and combinations thereof. In some embodiments, the ointment is applied as a ribbon onto the lower eyelid.

In some cases, the ophthalmic composition is an ophthalmic insert. In embodiments, the composition is administered intravitreally via an ophthalmic insert.

For example, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the IL-6a composition is dispersed within the matrix or bonded to the polymer matrix. In some embodiments, the agent is slowly released from the matrix through dissolution or hydrolysis of a covalent bond. In some embodiments, the polymer is bio-erodible (soluble) and the dissolution rate thereof can control the release rate of the agent dispersed therein. In another form, the polymer matrix is a biodegradable polymer that breaks down such as by hydrolysis to thereby release the agent bonded thereto or dispersed therein. In further embodiments, the matrix and agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly(dl-lactide-co-glycolide) (PLGA), or a copolymer of any of these. In some cases, the agent is dispersed into the matrix material or dispersed amongst the monomer composition used to make the matrix material prior to polymerization. In some embodiments, the amount of agent is from about 0.1 to about 50%, or from about 2 to about 20%. The biodegradable or bioerodible polymer matrix can be used so that the spent insert does not have to be removed from the eye. As the biodegradable or bioerodible polymer is degraded or dissolved, the agent is released.

In further embodiments, the ophthalmic insert comprises a polymer, including, but are not limited to, those described in Wagh, et al., "Polymers used in ocular dosage form and drug delivery systems", Asian J. Pharm., pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit@family of polymers from Rohm or Degussa), hydroxymethyl cellulose, polyacrylic acid, poly(amidoamine) dendrimers, poly(dimethylsiloxane), polyethylene oxide, poly(lactide-co-glycolide), poly(2-hydroxyethylmethacrylate), polyvinyl alcohol), or poly(propylene fumarate). In some embodiments, the insert comprises Gelfoam. In some embodiments, the insert is a polyacrylic acid of 450 kDa-cysteine conjugate.

The insert can comprise a core that contains the IL-6a composition and an outer tube (e.g., as described in U.S. Patent Pub. No. 20040009222). In some cases, the outer tube can be permeable, semi-permeable, or impermeable to the drug. In some embodiments, the core includes a polymer matrix that does not have a significant effect on the rate of IL-6a composition release. In some cases, the outer tube, the polymer matrix of the core, or both is bioerodible. The co-extruded product can be segmented into drug delivery devices. In some embodiments, the device is uncoated so that the respective ends are open, or the device is coated with, for example, a layer that is permeable to the IL-6a composition, semi-permeable to the IL-6a composition, or bioerodible. In certain embodiments, the IL-6a composition and at least one polymer are admixed in powder form.

In some embodiments, the ophthalmic composition is an ophthalmic film. Polymers suitable for such films include, but are not limited to, those described in Wagh, et al. (supra). In some embodiments, the film is a soft-contract lens, for example, a lens composed of copolymers of N,N-diethylacrylamide and methacrylic acid cross-linked with ethyleneglycol dimethacrylate.

In certain embodiments, the IL-6a is in an insert that is in a tubular form, and may be segmented.

In some embodiments, the IL-6a composition is formulated in a therapeutically effective amount, coated by or dispersed in a polymer matrix, such that the IL-6a composition is in granular or particulate form. In some embodiments, the IL-6a composition is released from the formulation as drug from the granules dissolves into or within the matrix, diffuses through the matrix, and is released into the surrounding physiological fluid. In some embodiments, the rate of release is limited primarily by the rate of dissolution of the IL-6a composition from the granules/particles into the matrix; the steps of diffusion through the matrix and dispersion into the surrounding fluid are primarily not release-rate-limiting. In certain embodiments, the polymer matrix is non-bioerodible, while in other embodiments it is bioerodible. Exemplary non-bioerodible polymer matrices can be formed from polyurethane, polysilicone, poly(ethylene-co-vinyl acetate) (EVA), polyvinyl alcohol, and derivatives and copolymers thereof. Exemplary bioerodible polymer matrices can be formed from polyanhydride, polylactic acid, polyglycolic acid, polyorthoester, polyalkylcyanoacrylate, and derivatives and copolymers thereof.

In some cases, the IL-6a composition is formulated in a collagenous material. For example, the insert can be a soluble ophthalmic drug insert (e.g., a polymeric oval film that can be introduced in the upper conjuctival sac for drug delivery; an elliptical insert such as OCUSERT® (pilocarpine ocular therapeutic system, developed by Alza Corporation) which is made of ethylene vinyl acetate; Lacrisert®, a rod shaped insert made of cellulose; New Ophthalmic Drug Delivery Systems (NODS), made of poly (vinyl alcohol); or inserts such as those described in Fabrizio (Adv Drug Deliv Rev 16: 95-106, 1998). In some cases, the insert comprises collagen, gelatin, or a polymer, wherein the polymer is selected from polycaprolactone (PCL), an ethylene/vinyl acetate copolymer (EVA), polyalkyl cyanoacrylate, polyurethane, a nylon, poly(dl-lactide-co-glycolide) (PLGA), or a copolymer of any of these. In some cases, the insert is implanted under the upper eyelid. In some cases, the insert is implanted in the posterior segment of the eye, in the choroidal space, or in the sclera. In some embodiments, the insert is implanted intravitreally or sub-retinally. In some embodiments, the insert is injected sub-retinally. Methods of administration and techniques for their preparation are set forth in *Remington's: The Practice of Science of Pharmacy*. 20$^{th}$ edition (Lippincott Williams & Wilkins, 2006), which is incorporated herein by reference in its entirety.

In other embodiments, an insert containing an IL-6a composition provides a sustained release of the agent to the vitreous of the eye. As used herein, "sustained release" means that the composition releases the agent over an extended period of time in a controlled fashion. In some embodiments, the insert releases the agent at a rate such that the aqueous agent concentration remains less than the vitreous agent concentration during the release. In some embodiments, the aqueous agent concentration is from about 0.002 μg/mL to about 0.01 pg/mL or from about 0.01 pg/mL, to about 0.05 μg/mL, or less than about 0.05 pg/mL. In some embodiments, the agent is released at a rate of about 1 pg/day to about 50 μg/day, or from about 1 μg/day to about 10 g/day. In some embodiments, the insert further comprises an additional therapeutic agent, as detailed above, e.g., fluocinolone acetonide (such as that found in the ophthalmic insert Retisert®).

In some embodiments, the ophthalmic composition comprises microspheres or nanoparticles. In some embodiment, the microspheres comprise gelatin. In some embodiments, the microspheres are injected to the posterior segment of the eye, in the choroidal space, in the sclera, intravitreally or sub-retinally. In some embodiments, the microspheres or nanoparticles comprises a polymer including, but not limited to, those described in Wagh, et al. (Asian J Pharm 2:12-17, 2008). In some embodiments, the polymer is chitosan, a polycarboxylic acid such as polyacrylic acid, albumin particles, hyaluronic acid esters, polyitaconic acid, poly(butyl) cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, an IL-6a composition comprises an ion-exchange resin. In some embodiments, the ion-exchange resin is an inorganic zeolite or synthetic organic resin. In some embodiments, the ion-exchange resin includes, but is not limited to, those described in Wagh, et al., supra, which is incorporated herein by reference in its entirety. In some embodiments, the ion-exchange resin is a partially neutralized polyacrylic acid.

An IL-6a composition can be provided in an aqueous polymeric suspension. In some embodiments, the IL-6a composition or a polymeric suspending agent is suspended in an aqueous medium (e.g., having the properties as described above). Examples of polymeric suspending agents include, but are not limited to, dextrans, polyethylene glycols, polyvinylpyrrolidone, polysaccharide gels, Gelrite®, cellulosic polymers like hydroxypropyl methylcellulose, and carboxy-containing polymers such as polymers or copolymers of acrylic acid, as well as other polymeric demulcents. In some embodiments, the polymeric suspending agent is a water swellable, water insoluble polymer, especially a cross-linked carboxy-containing polymer. In some embodiments, the polymeric suspending agent comprises from at least about 90% to about 99.9%, or from about 95% to about 99.9%, by weight based on the total weight of monomers present, of one or more carboxy-containing monoethylenically unsaturated monomers. In some embodiments, the carboxy-containing monoethylenically unsaturated monomer includes acrylic acid, methacrylic acid, ethacrylic acid, methylacrylic acid (crotonic acid), cis-.alpha.-methylcrotonic acid (angelic acid), trans-α-methylcrotonic acid (tiglic acid), α-butylcrotonic acid, .alpha.-phenylacrylic acid, α-benzylacrylic acid, α-cyclohexylacrylic acid, phenylacrylic acid (cinnamic acid), coumaric acid (o-hydroxycinnamic acid), and umbellic acid (p-hydroxycoumaric acid). In some embodiments, the polymer is cross-linked by a polyfunctional crosslinking agent (e.g., a difunctional crosslinking agent). In some embodiments, the crosslinking agent is contained in an amount of from about 0.01% to about 5%, or from about 0.1% to about 5.0%, or from about 0.2% to about 1%, based on the total weight of monomers present. In some embodiments, the crosslinking agents are nonpolyalkenyl polyether difunctional crosslinking monomers such as divinyl glycol, 2,3-dihydroxyhexa-1,5-diene, 2,5-dimethyl-1,5-hexadiene, divinylbenzene, N,N-diallylacrylamide, N,N-diallylmethacrylamide; polyalkenyl polyether crosslinking agents containing two or more alkenyl ether groupings per molecule, e.g., alkenyl ether groupings containing terminal $H_2C=C$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; diolefinic non-hydrophilic macromeric crosslinking agents having molecular weights of from about 400 to about 8,000, such as insoluble diacrylates and polyacrylates and methacrylates of diols and polyols, diisocyanate hydroxyalkyl acrylate or methacrylate reaction products of isocyanate terminated prepolymers derived from polyester diols, polyether diols or polysiloxane diols with hydroxyalkylmethacrylates, and the like.

In some embodiments, the cross-linked polymers are made from a carboxy-containing monoethylenically unsaturated monomer or monomers as the sole monoethylenically unsaturated monomer present, together with a crosslinking agent or agents. In some embodiments, the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrrolidone, and the like (e.g., Mueller et al. U.S. Pat. No. 4,548,990). In some embodiments, the polymers include polycarbophil (Noveon AA-1), Carbopol®, and DuraSite®. In some embodiments, the cross-linked polymers are prepared by suspension or emulsion polymerizing the monomers, using conventional free radical polymerization catalysts, to a dry particle size of not more than about 50 µm in equivalent spherical diameter. In some embodiments, the average dry particle size is from about 1 to about 30 µm, or from about 3 to about 20 µm in equivalent spherical diameter. In some embodiments, the polymer particles are obtained by mechanically milling larger polymer particles. In further embodiments, such polymers will have a molecular weight from about 250,000 to about 4,000,000, and from 3,000,000,000 to 4,000,000,000. In other embodiments, the particles of cross-linked polymer are monodisperse, meaning that they have a particle size distribution such that at least about 80%, about 90% or about 95%, of the particles fall within a µm band of major particle size distribution. In further embodiments, the monodisperse particle size means that there is no more than about 20%, about 10%, or about 5% particles of a size below 1 µm. In some embodiments, the aqueous polymeric suspension comprises from about 0.05 to about 1%, from about 0.1 to about 0.5%, or from about 0.1 to about 0.5%, of the agent and from about 0.1 to about 10%, from about 0.5 to about 6.5%, from about 0.5 to about 2.0%, from about 0.5% to about 1.2%, from about 0.6 to about 0.9%, or from about 0.6 to about 0.8% of a polymeric suspending agent. Although referred to in the singular, it should be understood that one or more species of polymeric suspending agent can be used with the total amount falling within the stated ranges. In one embodiment, the amount of insoluble lightly cross-linked polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm. In some embodiments, the viscosity is from about 10 to about 400 centipoise, from about 10 to about 200 centipoises or from about 10 to about 25 centipoise.

In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid. For instance, when a formulation containing DuraSite® or other similar polyacrylic acid-type polymer is administered to the eye at a pH of less than about 6.7, the polymer may swell upon contact with tear fluid since it has a higher pH (around 7). This gelation or increase in gelation may lead to entrapment of the suspended particles, thereby extending the residence time of the composition in the eye. In some embodiments, the agent is released slowly as the suspended particles dissolve over time. In some embodiments, this delivery route increases patient comfort and increased agent contact time with the eye tissues, thereby increasing the extent of drug absorption and duration of action of the formulation in the eye. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present.

In some embodiments, an IL-6 antagonist is provided to a subject using genetic delivery, e.g., local genetic delivery. Such delivery can be via a transient expression system, a stable (e.g., integrated) expression system such as a lentiviral delivery system manufactured by Bluebird Bio (Cambridge, Mass.), or delivery in a cell factory such as those manufactured by Neurotech (Cumberland, R.I.).

All technical features can be individually combined in all possible combinations of such features.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

The following non-limiting examples further illustrate embodiments of the inventions described herein.

Example 1: Validation of Local IL-6 Blockade in Choroidal Neovascularization (CNV) Model To determine whether local IL-6 blockade could be effective for treating eye disease, e.g., diabetic macular edema (DME) or wet AMD, an anti-IL-6 antibody was locally administered using a model system for choroidal neovascularization. A laser-induced CNV model (eyecro.com/in-vivo/laser-induced-choroidal-neovascularization-cnv/) reproduces many of the pathologic processes underlying DME including inflammation and angiogenesis. Studies were performed in rats at EyeCRO (Oklahoma City, Okla.). Six animals in each group underwent bilateral laser treatment on Day 0 to produce three lesions per eye. On days 3 and 10, 3 g of a polyclonal anti-rat-IL-6 antibody (R&D Systems AF506; Minneapolis, Minn.) was administered to the test group by intravitreal (IVT) injection, while PBS or an anti-VEGF polyclonal antibody (R&D Systems AF564) was administered to the vehicle and positive control groups, respectively. In vivo angiography was performed on days 15 and 22 to measure the lesion area.

On both days 15 and 22, the anti-IL-6 treated group had significantly reduced neovascularization compared to the vehicle control. There was no significant difference in response between the anti-IL-6 treated group and the anti-VEGF positive control. FIG. 1 shows the results of such an experiment. These data demonstrate that an IL-6a, e.g., an anti-IL6 antibody, administered IVT can reduce neovascularization in a rat CNV model to similar levels as an anti-VEGF positive control (p=0.0054 on Day 15 and p=0.0005 on Day 22 for anti-IL-6 vs. vehicle control).

These data indicate that local blockade of IL-6 can be useful for treating eye disease such as diseases involving vascular leakage, e.g., macular edema.

Example 2: Candidate Antibody IL-6 Antagonists

Candidate antibody IL-6 antagonists were developed using a process that first involved immunizations. Immunizations were performed at the direction of the inventors by a contract research organization (CRO). Five BALB/C mice were injected subcutaneously with 80 μg human IL-6 (R&D Systems, cat#206-IL/CF, Minneapolis, Minn.) in PBS containing 1 M NaCl with Freud's adjuvant. Two boosts were performed with 80 μg and 50 μg IL-6. Spleen cells were harvested from the highest titer mouse and fused with P3x763Ag8.653 myeloma cells to form hybridomas.

Hybridoma supernatants were screened for IL-6 binding and antagonism. For the binding ELISA, Costar 9018 plates were coated with 1 μg/mL human IL-6 in PBS overnight at 4° C. Wells were blocked with PBS containing 2% BSA, washed, and then incubated with 50 μL of each hybridoma supernatant diluted 1:2 with PBS containing 2% BSA. After 60 minutes, wells were washed three times with 300 μl PBS containing 0.1% Tween-20. Anti-mouse-HRP diluted 1:3000 in PBS-BSA was then added to each well and incubated for 30 minutes. Wells were washed as above then 3,3',5,5'-tetramethylbenzidine (TMB) substrate was added and the signal measured at 450 and 550 nm. For antagonism studies, HEK-Blue™-IL6 reporter cells (InvivoGen, San Diego, Calif.) were incubated with increasing concentrations of human IL-6 in the presence of 1:10 diluted hybridoma supernatant. After 20-24 hours, 20 μl of supernatant was mixed with 180 μl QuantiBlue™ (InvivoGen) and the absorbance measured at 655 nm.

Figure 2:
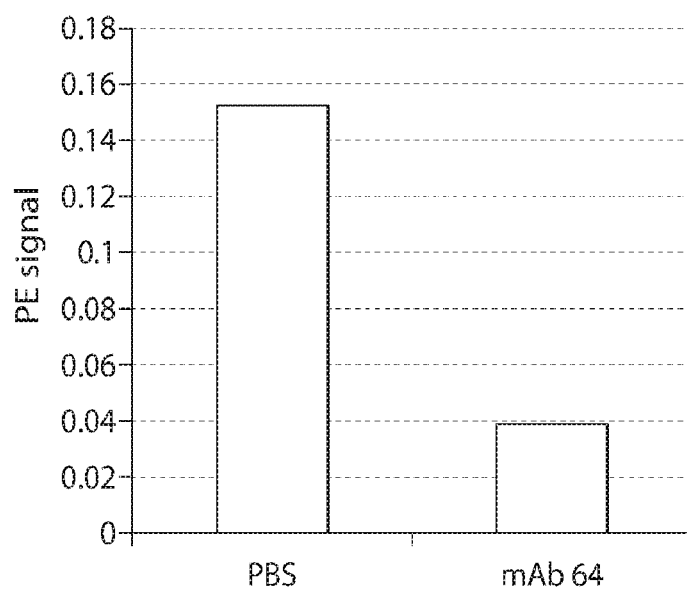
FIG. 2 is a graph illustrating results of a binding experiment testing the ability of the murine 64 antibody to inhibit binding of IL-6/IL-6R to gp130.

Based on binding and antagonism studies, hybridoma 64 was selected by applicants as a lead and subcloned at the CRO. Hybridoma 64 (a murine monoclonal) was further tested for the ability to inhibit binding of IL-6/IL-6Rα complex to gp130 using an enzyme-linked immunosorbant assay (ELISA). Hybridoma 64 at a concentration of 1.5 μg/ml significantly reduced binding of an IL-6/IL-6Rα complex to immobilized gp130 by ELISA (FIG. 2).

The subclones were rescreened and the variable domains of subclone 64.58 were amplified by 5' RACE PCR and sequenced. The mouse variable domain sequences (referred to as m64) are as follows:

```
m64 VH (variable heavy chain)
                                         (SEQ ID NO: 13)
QVQLQQSGAELVRPGTSVKVSCKASGYAFSNYLIEWVKQRPGQGLEWIGV

ITPGSGTINYNEKFKGKAVLTADKSSSTVYMQLSSLTSDDSAVYFCAKSR

WDPLYYYALEYWGQGTSVTVSS m64 VL (variable light chain)
                                         (SEQ ID NO: 14)
DIVLTQSPASLAVSLGQRATISCRASESVDNYGISFMNWFQQKPGQPPKL

LIYAASNQGSGVPARFSGSGSGTDFSLNIHPMEEDDTAMYFCQQSKEVPL

TFGAGTKLELK
```

To create humanized sequences, the m64 complementarity determining regions (CDRs) were grafted into a human germline framework selected for similarity to the mouse sequence by a computational algorithm. The humanized sequences (referred to as h64) were as follows (altered residues compared to the m64 sequences are underlined) and have about 79.5% identity (VH) and 84.4% identity (VL) with the murine sequences:

```
h64 VH
                                         (SEQ ID NO: 15)
QVQLVQSGAEVKKPGSSVKVSCKASGYAFSNYLIEWVRQAPGQGLEWMGV

ITPGSGTINYAQKFQGRVTITADESTSTAYMELSSLRSEDTAVYYCARSR

WDPLYYYALEYWGQGTTVTVSS h64 VL
                                         (SEQ ID NO: 16)
DIVMTQSPDSLAVSLGERATINCRASESVDNYGISFMNWYQQKPGQPPKL

LIYAASNQGSGVPDRFSGSGSGTDFTLTISSLQAEDVAVYYCQQSKEVPL

TFGQGTKLEIK
```

The humanized sequences were synthesized by DNA2.0 (Menlo Park, Calif.), then cloned into pcDNA3.1-derived expression vectors as inline fusions with the human IgG1 constant domains. IgGs were expressed by transient transfection in Freestyle™-293 cells (Invitrogen, Grand Island, N.Y.) and purified by protein-A chromatography. In both binding and antagonism studies, the h64 IgG demonstrated considerably reduced potency compared to its m64 predecessor. Therefore, yeast display was utilized to restore the lost affinity.

To carry out the affinity maturation designed to restore or improve the affinity of the humanized h64IgG, the h64 antibody sequences were recloned to generate a Fab molecule in pYC2/CT-derived yeast vectors in which the FabH chain was fused to the anti-FITC scFv 4m5.3 through a (G4S)3 linker (SEQ ID NO: 29). A library of h64 variants was then generated by error prone PCR following the protocol of Chao et al. (2006, Nature Protocols, 1:755-768). H64 variants were expressed and surface captured by yeast labeled with FITC-PEG-NHS then incubated with biotinylated human IL-6. Bound IL-6 was detected with streptavidin-APC, and cells with the highest amount of bound IL-6 relative to the amount of displayed Fabs were selected on a BD FACSAria™ cell sorter. After four rounds of selection, a population of higher affinity variants was selected and sequenced. The sequence of the clone selected by affinity maturation (referred to as h64-1.4) is as follows with the selected mutations (i.e., mutated compared to the sequences of h64 VH and VL) in boldface and the CDRs are underlined. These are the variable domains of 018 (as well as the 020 and 029 IL-6a molecules described below). Note that the full Fabs include the CK and IgG1 CH1 domains. In the context of this application, reference to a "Fab" heavy chain or light chain amino acid sequence means that sequence can be part of a functioning Fab consisting of a light chain-derived sequence and a heavy chain-derived sequence.

h64-1.4 VH (018VH)(variable domain)
(SEQ ID NO: 17)
QVQLVQSGAEVKKPGSSVKVSCKAS<u>GYALSNYLI</u>EWVRQAPGQGLEWMG<u>V</u>

<u>ITPGSGTINYAQKFQG</u>RVTITADESTSTAYMELSSLRSEDTAVYYCAR<u>SR</u>

<u>WDPLYYYALEY</u>WGQGTTVTVSS h64-1.4 VL (018VL) (variable domain)
(SEQ ID NO: 18)
DIVMTQSPDSLAVSLGERATINC<u>RASESVDNYGIPFMN</u>WYQQKPGQPPKL LIY<u>AASNRGS</u>GVPDRFSGSGSGTDFTLTISSLQAEDVAVYY<u>CQQSEEVPL</u>

<u>T</u>FGQGTKLEIKRTV

The h64-1.4 variable domains were recloned into the pcDNA3.1 human IgG1 vector and expressed as a full length IgG1 in Freestyle™-HEK293 cells (Life Technologies). The resulting purified IgG was significantly more potent than the original h64 antibody in both binding and cellular antagonism studies. Testing affinity using the yeast system, the affinity increased from 343 pM for the original humanized molecule to 43 pM. The antagonist potency was about a ten-fold increase as assayed using the HEK-Blue cell system.

The h64-1.4 IgG was reformatted as a Fab for use in ocular and other indications. Additionally, another round of library generation and yeast based selections was performed to further improve affinity. After four rounds of selection, there was significant enrichment for a VH variant with the A79V mutation. Antibodies, variants and fragments thereof comprising the A79V variant are referred to as 019 IL-6a antibodies, variants, and fragments thereof.

Example 3: Format Selection

To investigate suitable formats for an antibody-based IL-6 antagonist, IL-6 antibodies selected as described supra were tested for transient expression, stability, aggregation properties, binding affinity, and IC50 using Fab, scFv($V_H$—$V_L$) and scFv($V_L$—$V_H$) forms of the 018 sequences.

Results of these studies for one of the candidate IL-6a molecules (sequences containing the 018 variable region) are shown in Table 1.

TABLE 1

| Parameter | Fab | scFv($V_H$-$V_L$) | scFv($V_L$-$V_H$) |
|---|---|---|---|
| Transient expression | 45 mg/ml | 2 mg/L | 4 mg/L |
| Stability ($T_M$) | 73° C. | 43° C. | 46° C. |
| Aggregation (SEC, MALS) | No | Yes | N/A |
| Binding affinity ($K_D$) | 240 pM | 1 nM | 720 pM |
| IC50 with 10 pM IL-6 | 255 pM | 160 pM | 125 pM |

These data demonstrate a method of identifying key features of various formats of an antibody-based IL-6 antagonist and illustrates that for IL-6 antagonists containing the 018 variable regions, the 018Fab format has the most favorable features in most key categories, i.e., expression, stability, aggregation, and binding affinity compared to an scFv configuration. The IC50 of the 018 Fab falls within a reasonable range for therapeutic use.

Example 4: Examples of IL-6a Antibodies, Fragments, and Derivatives

Applicants have identified the following sequences using methods described herein. Underlined sequences represent CDRs of the heavy and light chains. Other sequences can be found throughout the specification.

018 Heavy chain (full length; f1018HC) polypeptide
sequence in an IgG1 framework
(SEQ ID NO: 19)
QVQLVQSGAEVKKPGSSVKVSCKAS<u>GYALSNYLI</u>EWVRQAPGQGLEWMG<u>V</u>

<u>ITPGSGTINY</u>AQKFQGRVTITADESTSTAYMELSSLRSEDTAVYYCAR<u>SR</u>

<u>WDPLYYYALEY</u>WGQGTTVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSP

GK

018 Heavy chain (full length; f1018HC) nucleic
acid sequence in an IgG1 framework
(SEQ ID NO: 20)
CAAGTGCAGCTGGTGCAGTCAGGGGCCGAGGTTAAGAAGCCAGGGAGCAG

CGTCAAGGTATCTTGTAAAGCGTCTGGTTACGCCCTTTCAAACTACCTGA

TCGAATGGGTGAGGCAGGCTCCCGGCCAAGGCCTGGAATGGATGGGAGTT

```
ATCACCCCTGGGAGCGGCACCATTAATTACGCCCAGAAATTTCAGGGACG

AGTGACGATTACCGCCGACGAGTCCACCAGTACTGCCTACATGGAGCTGT

CCTCACTCCGCAGCGAGGACACGGCAGTTTACTACTGCGCCCGGAGTCGA

TGGGACCCTCTTTACTATTATGCTCTGGAATACTGGGGCCAGGGAACGAC

CGTTACAGTGTCATCTGCTAGCACAAAAGGACCATCAGTCTTCCCACTTG

CTCCTTCATCTAAGAGCACAAGTGGTGGCACTGCAGCCCTTGGCTGCCTG

GTGAAAGATTATTTCCCCGAACCTGTTACAGTTTCTTGGAACTCCGGTGC

ACTGACATCCGGAGTACACACTTTCCCAGCTGTGCTGCAGAGCTCAGGAC

TGTATAGCCTGTCTTCGGTGGTCACTGTTCCATCGTCAGTCTTGGCACA

CAGACATATATTTGCAACGTCAATCACAAGCCCTCCAACACAAAAGTGGA

TAAGAAGGTCGAGCCCAAATCTTGTGACAAGACCCATACGTGTCCTCCCT

GTCCCGCCCCTGAACTGCTGGGAGGCCCTTCTGTGTTCCTGTTCCCACCT

AAGCCAAAGGACACTCTGATGATCAGCCGGACTCCCGAGGTTACCTGTGT

GGTGGTGGATGTGTCTCATGAAGACCCTGAGGTTAAGTTCAATTGGTACG

TGGATGGCGTCGAGGTGCATAACGCAAAAACCAAGCCGAGAGAGGAGCAG

TACaatAGCACCTATAGAGTAGTGAGCGTCCTGACTGTCTTACATCAGGA

TTGGCTCAATGGTAAAGAATATAAGTGCAAGGTAAGCAACAAGGCCCTAC

CCGCACCAATAGAGAAGACCATCTCCAAGGCGAAAGGTCAGCCCAGGGAG

CCCCAGGTTTATACACTGCCTCCCTCACGCGACGAATTAACAAAGAATCA

GGTGTCTCTCACCTGTCTCGTCAAGGGCTTTTACCCTTCCGACATCGCCG

TGGAGTGGGAATCCAATGGCCAGCCTGAGAACAATTATAAGACAACTCCC

CCAGTCCTGGATTCAGATGGGTCGTTCTTTCTATATAGTAAGTTGACCGT

GGATAAGTCTCGCTGGCAACAGGGGAACGTGTTCTCTTGCTCTGTTATGC

ATGAAGCGCTGCACAATCATTATACCCAGAAGTCCCTGTCCCTGAGCCCC

GGGAAG
```

018 Fab Heavy Chain (018FabHC) polypeptide sequence in an IgG1 framework. CDRs are underlined
(SEQ ID NO: 1)
QVQLVQSGAEVKKPGSSVKVSCKAS<u>GYALSNYLIE</u>WVRQAPGQGLEWMG<u>V ITPGSGTINY</u>AQKFQGRVTITADESTSTAYMELSSLRSEDTAVYYCAR<u>SR WDPLYYYALEY</u>WGQGTTVTVSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKKVEPKSC 018 full length light chain (f1018LC) polypeptide sequence. CDRs are underlined
(SEQ ID NO: 2)
DIVMTQSPDS LAVSLGERAT INC<u>RASESVD NYGIPFMN</u>WY QQKPGQPPKL LIY<u>AASNRGS</u> GVPDRFSGSG SGTDFTLTIS SLQAEDVAVY YC<u>QQSEEVPL T</u>FGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC This is also the light chain sequence for 020 and 029 IL-6 antagonists 018 full length light chain (018LC) nucleic acid sequence in an IgG1 framework
(SEQ ID NO: 26)
```
GACATAGTGA TGACTCAAAG TCCGGACAGC TGGCGGTGT
CACTCGGCGA ACGGGCAACT ATCAACTGCC GAGCCAGCGA
GAGCGTCGAT AATTACGGCA TCCCCTTCAT GAACTGGTAT
CAGCAGAAGC CAGGACAGCC GCCCAAGCTG CTTATCTACG
CCGCTTCCAA CCGGGGATCA GGGGTGCCCG ATCGATTTAG
TGGAAGCGGT AGTGGGACCG ATTTCACACT GACCATCAGC
TCCCTTCAGG CCGAGGATGT GGCTGTCTAT TATTGTCAGC
AATCCGAGGA AGTGCCGCTC ACGTTTGGTC AGGGAACCAA
ACTGGAGATC AAGCGGACCG TAGCGGCGCC TAGTGTCTTC
ATCTTCCCAC CCTCCGACGA ACAGCTGAAG TCTGGCACTG
CTTCCGTCGT GTGCCTGCTC AACAACTTTT ACCCTAGAGA
GGCAAAAGTT CAATGGAAAG TAGACAATGC CTTGCAGTCC
GGGAACTCCC AGGAGTCTGT CACAGAGCAG GATAGTAAGG
ACTCAACCTA CAGCCTGTCC AGCACACTGA CCCTCTCCAA
AGCCGACTAC GAGAAGCACA AAGTGTACGC TTGCGAAGTT
ACGCATCAGG GCCTGTCCTC ACCCGTTACA AAAAGTTTTA
ACAGAGGGGA GTGC
```

019 Fab Heavy Chain (019FabHC, same sequence as 018FabHC except for A79V (bold/italic)
(SEQ ID NO: 3)
QVQLVQSGAE VKKPGSSVKV SCKAS<u>GYALS NYLIE</u>WVRQA PGQGLEWMG<u>V ITPGSGTINY</u> AQKFQGRVTI TADESTSTVY MELSSLRSED TAVYYCAR<u>SR WDPLYYYALE YW</u>GQGTTVTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSC 019 VH (variable region/019HC)
(SEQ ID NO: 27)
QVQLVQSGAE VKKPGSSVKV SCKAS<u>GYALS</u> <u>NYLIE</u>WVRQA PGQGLEWMG<u>V</u> <u>ITPGSGTINY</u> AQKFQGRVTI TADESTST*V*Y MELSSLRSED TAVYYCAR<u>SR</u> <u>WDPLYYYALE</u> <u>YW</u>GQGTTVTV SS The 019 antibody light chain (019LC) sequence (polypeptide and nucleic acid) is the same as the 018LC CDR1 of 018HC (VH CDR1 018):
(SEQ ID NO: 4)
GYALSNYLIE CDR2 of 018HC (VH CDR2 018):
(SEQ ID NO: 5)
VITPGSGTIN CDR3 of 018HC (VH CDR3 018):
(SEQ ID NO: 6)
SRWDPLYYYALEY CDR1 of 018LC (VL CDR1):
(SEQ ID NO: 7)
RASESVDNYGIPFMN -continued CDR2 of 018LC (VL CDR2):
(SEQ ID NO: 8)
AASNRGS CDR3 of 018LC (VL CDR3):
(SEQ ID NO: 9)
QQSEEVPLT CDR1 of 019HC (VH CDR1 019):
(SEQ ID NO: 4)
GYALSNYLIE CDR2 of 019HC (VH CDR2 019):
(SEQ ID NO: 5)
VITPGSGTIN CDR3 of 019HC (VH CDR3 019):
(SEQ ID NO: 6)
SRWDPLYYYALEY

Example 5: Epitope and Structure Mapping

Epitope Mapping

Functional epitope mapping was performed on selected candidate IL-6 antagonists. It was found that a candidate antibody (murine 64 antibody) did not reduce binding of IL-6Rα to IL-6 in an ELISA indicating that the candidate antibody is not binding to site I. Additional experiments were conducted demonstrating that chimeric murine 64 antibody reduced binding of IL-6/IL-6Rα complex to gp130 in an ELISA indicating that either Site II or Site III of IL-6 harbored the binding site for the antibody. It was also found that murine 64 antibody did not significantly block binding of a known site III binding antibody AH-65 (Immunotech, Marseille, France) to IL-6 indicating that the candidate antibody binds site II of IL-6. These data demonstrate that antibodies against site II can be generated and demonstrates a method of identifying such antibodies.

To further define the epitope, mutations in IL-6 were generated in yeast as fusions to 4m5.3 (Boder et al., 2000, Proc Natl Acad Sci USA 97, 10701-10705; Chao et al., 2006, Nat Protoc 1, 755-768). The mutations expressed were in human IL-6 with the following single or double mutations: R24E/D27E, R30E, Y31E, D34R, S118R/V121E, W157E, Q159E/T162P, K171E, and R179E. The expressed mutated IL-6 molecules were used in binding studies with 018 (Fab). Reduced affinity for 018 (Fab) was observed for R24E/K27E, Y31E, D34R, and S118R/V121R, all of which are located in site II of IL-6. Accordingly, the invention described herein includes an antibody that binds to at least one, two, three, four, five, or six of the amino acids at position 24, 27, 31, 34, 118, and 121 of human IL-6 or the equivalent site in an IL-6.

Structural Definition of a Site II Epitope

The following distances were calculated to structurally define site II. The calculations are based on the IL-6/IL-6a/gp130 hexameric crystal structure, PDB 1P9M (Boulanger et al., 2003, Science 300: 2101-2104). Helix 1 of IL-6 runs between site I and site II resulting in certain residues that fall close to site II but have side chains that point toward site I, e.g., R30. D2 and D3 refer to extracellular domains of IL-6Rα.

The following amino acids of IL-6 were determined to fall within 5 Å of gp130-D2-D3: L19, R24, K27, Q28, R30, Y31, D34, E110, Q111, R113, A114, M117, S118, V121, Q124, F125, and K128 The following amino acids were determined to fall within 7 Å of gp130-D2-D3: L19, E23, R24,I25, K27, Q28,I29, R30, Y31, D34, K41, Q102, E109, E110, Q111, A12, R113, A114, V115, Q16, M117, S18, K120, V121, L122, Q124, F125, and K128.

Accordingly, a molecule, e.g., an antibody or fragment thereof that can bind one or more of the IL-6 amino acids falling within 5 Å or 7 Å of site II can be an IL-6a.

The sequence of human IL-6 is provided below for reference (underlined sequence is the leader sequence). Amino acids within 7 Å of gp130-D2-D3 are in italics. The amino acid numbering, e.g., mutations used to define epitopes, is without the leader sequence:

Human IL-6
(SEQ ID NO: 21)
MNSFSTSAFGPVAFSLGLLLVLPAAFPAPVPPGEDSKDVAAPHRQPLTSS

ERIDKQIRYILDGISALRKETCNKSNMCESSKEALAENNLNLPKMAEKDG

CFQSGFNEETCLVKIITGLLEFEVYLEYLQNRFESSEEQARAVQMSTKVL

IQFLQKKAKNLDAITTPDPTTNASLLTKLQAQNQWLQDMTTHLILRSFKE

FLQSSLRALRQM

Experiments were conducted testing the Fab fragment of the h64-1.4 humanized antibody and demonstrated that it was able to block both cis and trans IL-6 signaling, which is due to site II targeting. The potency of the Fab fragment was unchanged in the presence of soluble IL-6 receptor (sIL-6R). This is in contrast to an anti-IL-6R IgG that had decreased potency in the presence of sIL6R, and that blocks cis signaling only.

These experiments demonstrate that an antibody or fragment of the antibody such as a Fab fragment that targets site II can be used to inhibit both cis and trans signaling of 11-6.

Example 6: Primate Studies

Because non-primate activities can differ greatly from those of primates, candidate IL-6 antagonists are typically further assessed for PK and other parameters using non-human primates. Human IL-6 differs from cynomolgus monkey and rhesus monkey IL-6 at seven sites, one of which is in site II (amino acid 28) and is the same at site II in African green monkey IL-6. This appears to decrease binding of an antibody comprising 018 sequences by only about 3-4 fold. The ability to bind to a non-human primate IL-6 is a useful feature of an IL-6 antagonist, facilitating development of the candidate as a drug, e.g., by enabling testing such as toxicology testing in non-human primates.

As with most IL-6 antibodies, anti-IL-6 antibodies described herein did not cross-react to rodent, rabbit, or canine IL-6 due to low sequence homology. However, in affinity studies, it was found that 018 Fab binds cynomolgus monkey and African green monkey IL-6 with approximately human affinity (Table 2).

TABLE 2

Monovalent affinity (018 Fab) for various IL-6 of various species

| Species | $K_D$ |
| --- | --- |
| Human | 200 pM |
| African Green Monkey | 280 pM |
| Cynomolgus monkey | 840 pM |
| Dog | >1 μM |
| Mouse | >1 μM |
| Rabbit | >1 μM |
| Rat | >1 μM |

These data further demonstrate the ability of an IL-6a as described herein to specifically bind and the ability to develop a molecule having features permitting testing, e.g., for toxicology and reproductive studies, in a suitable animal.

Example 7: Increasing Expression of an IL-6a

To increase expression of 018 Fab and 019 Fab polypeptides, constructs were made introducing five additional amino acids (DKTHT (SEQ ID NO: 30)) to the heavy chain in the CH1/hinge region using methods known in the art. The sequence of the altered 018Fab heavy chain is shown below as SEQ ID NO:24. The altered 018 sequence is referred to herein as 020 and the altered 019 sequence is referred to herein as 021. The 020 molecule (the 020Fab heavy chain and the 018Fab light chain) had improved expression compared to the parent Fab that had 018Fab heavy and 08Fab light chains. The 019 molecule exhibited no significant affinity difference compared to the 020 molecule. Expression of both 020 and 019 was increased by about two fold, respectively, and the affinities were not affected by the alteration.

```
020 Heavy chain (Fab with DKTHT (SEQ ID NO: 30)
at the carboxy terminus))
                                      (SEQ ID NO: 24)
QVQLVQSGAE VKKPGSSVKV SCKASGYALS NYLIEWVRQA

PGQGLEWMGV ITPGSGTINY AQKFQGRVTI TADESTSTAY

MELSSLRSED TAVYYCARSR WDPLYYYALE YWGQGTTVTV

SSASTKGPSV FPLAPSSKST SGGTAALGCL VKDYFPEPVT

VSWNSGALTS GVHTFPAVLQ SSGLYSLSSV VTVPSSSLGT

QTYICNVNHK PSNTKVDKKV EPKSCDKTHT
```

Figure 3A:
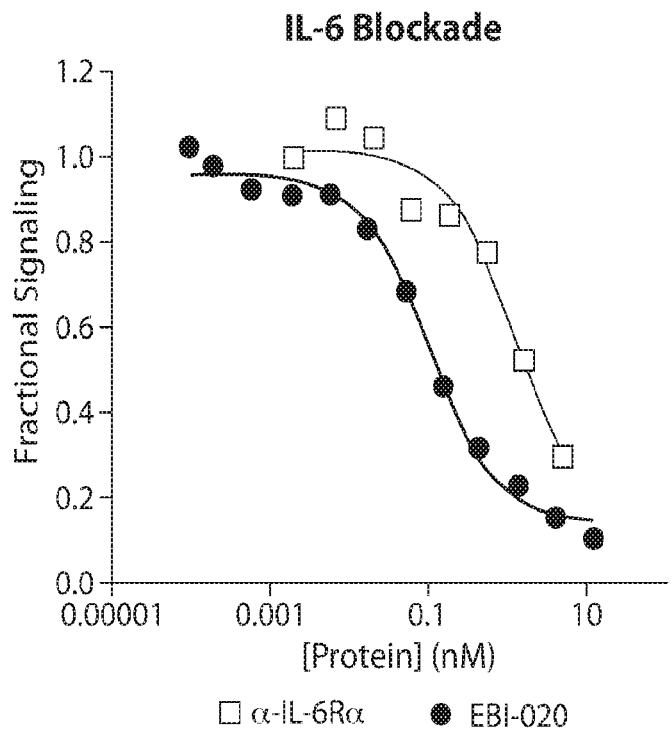
FIG. 3A is a graph illustrating an experiment in which 020 was tested for the ability to block IL-6 signaling in the absence of an excess of soluble IL-6Rα. Experiments were performed in HEK-Blue-IL-6 cells with 0.2 ng/mL IL-6 and 2 μg/mL IL6Rα.
Figure 3B:
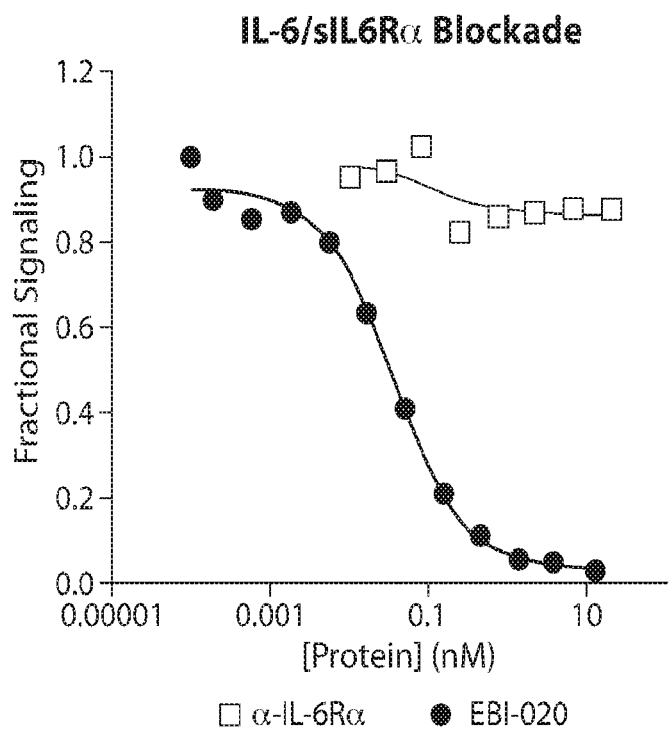
FIG. 3B is a graph illustrating an experiment in which 020 was tested for the ability to block IL-6 signaling in the presence of an excess of soluble IL-6Rα. Experiments were performed in HEK-Blue-IL-6 cells with 0.2 ng/mL IL-6 and 2 μg/mL IL6Rα.

IL-6 antagonism using the 020Fab was measured in HEK-Blue™ IL-6 reporter cells (InvivoGen, San Diego, Calif.). Cells were incubated in a mixture of 10 pM IL-6 and varying concentrations of either 020 or IL-6Rα antibody (Cell Sciences, Canton, Mass.), with or without 50 nM IL-6Rα. After 20-24 hours of incubation, 20 μL of cell culture supernatant was mixed with 180 μL of QuantiBlue™ (InvivoGen) substrate and incubated for one hour; the absorbance was then measured at 655 nm. FIG. 3A and FIG. 3B show data from these experiments, demonstrating the ability of 020 to inhibit IL-6 activity in the presence or absence of IL-6R.

Example 8: IgG2 IL-6 Antibodies 018 was reformatted into a human IgG2 isotype framework to reduce FcγR binding and reduce ADCC compared to the IgG1 formatted antibody using methods known in the art. In addition, reformatting 018 to a full-length format, e.g., an IgG2, is expected to decrease the rate of clearance from the vitreous due to the larger size of the molecule.
Construction/Purification of Anti-IL6 IgG2 Antibodies To construct human IgG2 antibodies using anti-IL-6 sequences described supra, a human IgG2 constant domain was PCR amplified from cDNA with NheI and M1uI restriction sites at the N- and C-terminal ends, respectively. The PCR product was purified, digested with NheI and M1uI restriction enzymes, and then ligated into pTT5 vector containing anti-IL6 variable domain, i.e., SEQ ID NO:1 (see above). This yielded a full-length IgG2 heavy chain sequence. Plasmids containing the full-length light chain containing the 018 sequence were used to provide light chain.

To further reduce FcRn binding and thereby reduce recycling of the IL-6a, point mutations were made in the heavy chain. The mutations were made by QuikChange® mutagenesis (Agilent Technologies, Santa Clara, Calif.). The heavy and light chain plasmids were co-transfected using poly(ethylenimine) (PEI) into 100 mL transient cultures of HEK293-6E cells and cultured to allow expression for about five days. This generated antibodies containing an anti-IL-6 site II binding moiety and IgG2 structure. Such structures containing 018 CDRs are termed herein 018IgG2 or 029. The point mutations were made at residues I253

The IgG2 molecule was well expressed and blocks IL-6 in cellular assays with slightly improved potency compared to the 020Fab.

```
029 mature sequences (CDRs underlined)
029 Heavy chain
                                      (SEQ ID NO: 11)
QVQLVQSGAE VKKPGSSVKV SCKASGYALS NYLIEWVRQA

PGQGLEWMGV ITPGSGTINY AQKFQGRVTI TADESTSTAY

MELSSLRSED TAVYYCARSR WDPLYYYALE YWGQGTTVTV

SSASTKGPSV FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLMISRTPEV TCVVVDVSHE DPEVQFNWYV

DGVEVHNAKT KPREEQFNST FRVVSVLTVV HQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK

029 Light chain
                                      (SEQ ID NO: 12)
DIVMTQSPDS LAVSLGERAT INCRASESVD NYGIPFMNWY

QQKPGQPPKL LIYAASNRGS GVPDRFSGSG SGTDFTLTIS

SLQAEDVAVY YCQQSEEVPL TFGQGTKLEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

Altered FcRn Binding

IL-6 can have certain positive systemic effects. It is therefore an advantage to engineer an IL-6a that has good retention in the vitreous but has a limited systemic half-life. The reduction or elimination of FcRn binding should reduce systemic accumulation of any drug that escapes into circulation, thereby improving safety of an IL-6a.

Accordingly, because FcRn mediated trafficking may increase the efflux of antibodies from the eye, the 020 IgG2 was further modified to ablate FcRn binding by introducing Fc mutations at residues I254, H311, or H436 (See SEQ ID NO:23) numbering according to Martin et al., Molecular Cell, 7:4, 867-877 (2001)). The mutated sites are shown in boldface in SEQ ID NO:23; I254 was mutated to A or R, H311 was mutated to A or E, H311 was mutated to N with D 313 mutated to T, and H436 was mutated to A (numbering starts after the leader sequence, which is underlined in SEQ ID NO:23. IL-6 antagonists containing such sequences are termed 018IgG2m.

```
Anti-IL-6 heavy chain (IgG2) (regular font: VH;
italic font: CH) (without leader sequence)
showing mutation sites (boldface)
                                    (SEQ ID NO: 23)
QVQLVQSGAE VKKPGSSVKV SCKASGYALS NYLIEWVRQA

PGQGLEWMGV ITPGSGTINY AQKFQGRVTI TADESTSTAY

MELSSLRSED TAVYYCARSR WDPLYYYALE YWGQGTTVTV

SSASTKGPSV FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLMISRTPEV TCVVVDVSHE DPEVQFNWYV

DGVEVHNAKT KPREEQFNST FRVVSVLTVV HQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK

Anti-IL-6 heavy chain (IgG2) (regular font: VH;
italic font: CH) with leader sequence (underlined)
showing mutation sites (boldface)
                                    (SEQ ID NO: 28)
MDWTWRILFLVAAATGAHSQVQLVQSGAE VKKPGSSVKV

SCKASGYALS NYLIEWVRQA PGQGLEWMGV ITPGSGTINY

AQKFQGRVTI TADESTSTAY MELSSLRSED TAVYYCARSR

WDPLYYYALE YWGQGTTVTV SSASTKGPSV FPLAPCSRST

SESTAALGCL VKDYFPEPVT VSWNSGALTS GVHTFPAVLQ

SSGLYSLSSV VTVPSSNFGT QTYTCNVDHK PSNTKVDKTV

ERKCCVECPP CPAPPVAGPS VFLFPPKPKD TLMISRTPEV

TCVVVDVSHE DPEVQFNWYV DGVEVHNAKT KPREEQFNST

FRVVSVLTVV HQDWLNGKEY KCKVSNKGLP APIEKTISKT

KGQPREPQVY TLPPSREEMT KNQVSLTCLV KGFYPSDIAV

EWESNGQPEN NYKTTPPMLD SDGSFFLYSK LTVDKSRWQQ

GNVFSCSVMH EALHNHYTQK SLSLSPGK
```

Accordingly, some embodiments include an antibody having the heavy chain sequence depicted in SEQ ID NO:23 with mutations at I254 (e.g., A or R), H311 (mutated to A or E), H436 (mutated to A), or D313 (mutated to T) with H311 mutated to N.

SEQ ID NO:25 therefore provides a sequence that, when mutated at I133 (e.g., I133 A or I133R), H190 (e.g., H190A or H190E), H315 (e.g., H315A), or D192 with H190 (e.g., D192T with H190N) can be used in an antibody, fragment, or derivative thereof to produce a polypeptide having reduced Fc binding at low pH, e.g., pH 5.5 or lysosomal pH and/or a polypeptide having reduced systemic half-life compared to a parent or other reference molecule that does not include the sequence.

```
                                    (SEQ ID NO: 25)
SASTKGPSV FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLMISRTPEV TCVVVDVSHE DPEVQFNWYV

DGVEVHNAKT KPREEQFNST FRVVSVLTVV HQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK

Anti-IL-6 light chain (IgG2) (regular
font: VK; italic font: CK)
                                    (SEQ ID NO: 22)
DIVMTQSPDSLAVSLGERATINCRASESVDNYGIPFMNWYQQKPGQPPKL

LIYAASNRGSGVPDRFSGSGSGTDFTLTISSLQAEDVAVYYCQQSEEVPL

TFGQGTKLEIKRTVAAPSVFIFPPSDEQLK SGTASVVCLL

NNFYPREAKV QWKVDNALQS GNSQESVTEQ DSKDSTYSLS

STLTLSKADY EKHKVYACEV THQGLSSPVT KSFNRGEC
```

Example 9: Formulation Stability

The stability of the anti-IL-6/IgG1 Fab fragment (containing the IgG1CH1 domain) was tested by determining the $T_m$ initially in PBS then in a range of buffers and excipients using differential scanning fluorimetry. It was found that citrate buffer, pH 5.5 increased the $T_m$ to more than 80° C. Accordingly, in some embodiments, an IL-6a is provided in citrate buffer and in some cases has a $T_m$ of at least 80° C.

Aggregation was tested using SEC-MALS and no aggregation was observed at 20 mg/ml in phosphate buffered saline (PBS).

Example 10: pH Sensitive Antibodies for Enhanced PK

IL-6 can have certain positive systemic effects. It is therefore an advantage to engineer an IL-6a that has good retention in the vitreous but has a limited systemic half-life. The reduction or elimination of FcRn binding should reduce systemic accumulation of any drug that escapes into circulation, thereby improving safety of an IL-6a. Accordingly, because FcRn mediated trafficking may increase the efflux of antibodies from the eye, the 020 IgG2 was further modified to ablate FcRn binding by introducing Fc mutations at residues I253, H310, or H435 (numbering according to Martin et al. (Molecular Cell, 7:4,867-877 (2001))). Such antibodies are referred to herein as IL-6 pH antibodies or anti-IL-6 pH and are further described below.

Generation of Antibodies with pH Sensitive Binding

The pKa of histidine is about 6.0 and histidines inserted at binding interfaces can disrupt binding upon side-chain protonation at low pH. Using an anti-IL-6 site II targeted antibody as described herein, a library was generated containing histidine-rich variants of CDRs from 018 and the library was screened for pH-sensitive binding using yeast display. The library generated was a combinatorial library with CDRs encoded by degenerate codons such that each residue is either a wild-type residue (i.e., the same as in the parental antibody) or a histidine residue. The screening was performed by alternating sorting for high binding at physiological pH (7.4) and low binding at endosomal pH (5.5).

A yeast-selected mutant was identified that had relatively high binding at pH 7.4 (monovalent Kd of 407 pM for the mutant compared to 192 pM for the parent molecule) and relatively low binding at pH 5.5 (monovalent Kd of 2.362 nM for the mutant compared to 195 pM for the parent). This constitutes an approximately 5.8 fold change in the affinity at pH 5.5. This mutant contained multiple histidine mutations in the light chain CDR1. Thus, the mutant demonstrated similar binding to the parent molecule at pH 7.4, and a significant loss of affinity at pH 5.5. This observation was verified using ELISA, FACS, and SPR analysis by methods known in the art.

These data demonstrate that an IL-6a that is based on an antibody can be created that has the features of an anti-IL-6 targeting site II of IL-6 that can be used to inhibit both cis and trans activity of IL-6, and have increased PK compared to a parent antibody or other antibody having a wild type Fc domain effected at least in part by altered binding at pH 5.5.

Example 11: Efficacy of Local IL-6 Blockade in Mouse Laser Choroidal Neovascularization (CNV) Model To determine whether local IL-6 blockade could be effective for treating eye disease, e.g., diabetic macular edema (DME) or wet AMD, a monoclonal anti-IL-6 antibody was locally administered in a model system for choroidal neovascularization. The laser-induced CNV model as described in Saishin et al. Journal of Cellular Physiology, 195:241-248 (2003) was employed in this Example. A laser-induced CNV model reproduces many of the pathologic processes underlying diabetic macular edema (DME), including inflammation and angiogenesis.

A monoclonal anti-mouse IL-6 antibody (MP5-20F3, which is a rat IgG1 isotype antibody purchased from Bio X Cell, catalog number BE0046) was administered to the test group by intravitreal (IVT) injection. Controls received intravitreal injection of VEGF trap or intravitreal injection of an anti-HRP isotype control antibody (a rat IgG1 against horseradish peroxidase, clone HRPN, purchased from BioX-Cell; catalog number BE0088). For all antibody groups, 20 g of protein in a 1 L volume was injected into the test eye, while the contralateral eye was left untreated as a further control.

Figure 4:
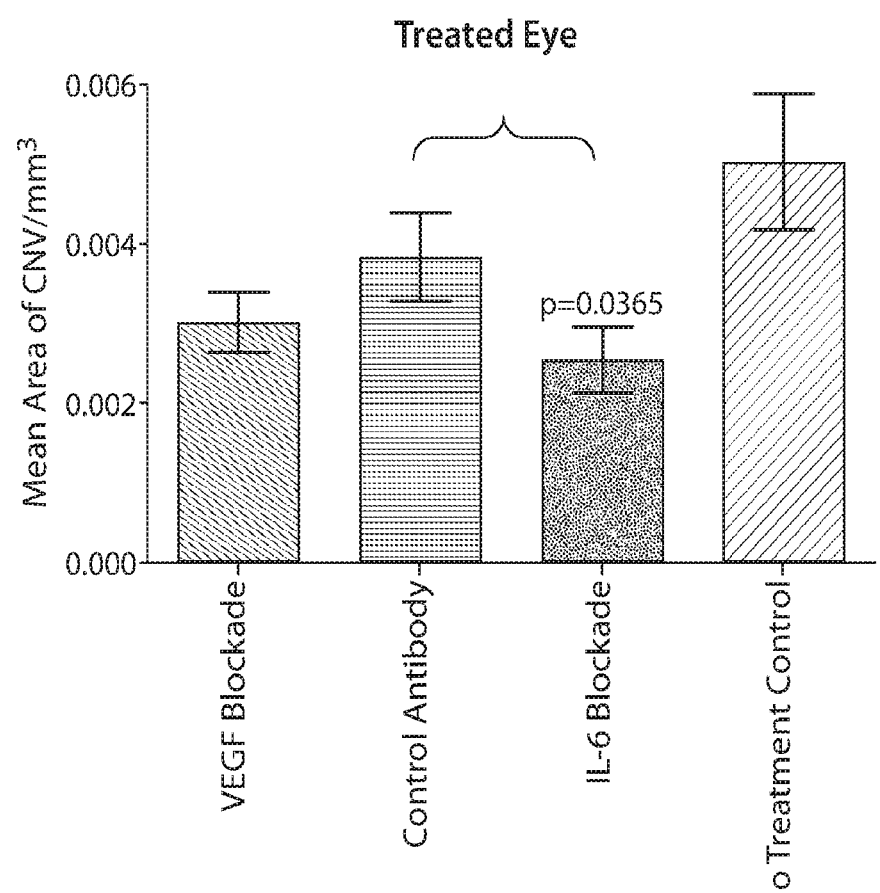
FIG. 4 is a graph illustrating the results of an experiment in which a monoclonal anti-IL-6 antibody ("IL-6 Blockade") was administered IVT in a mouse CNV model. Controls were no treatment (contralateral eye), intravitreal injection of an anti-VEGF antibody ("VEGF Blockade") or intravitreal injection of an anti-HRP isotype control antibody ("Control Antibody").

Mice were euthanized on day 7 after laser and choroidal flat mounts were stained with *Griffonia Simplicifolia* (GSA) lectin to measure the lesion area. FIG. 4 shows the results. The anti-IL-6 antibody treated group showed a statistically significant reduction in neovascularization compared to the control antibody treated group (p<0.05). On average the anti-IL-6 antibody treated group also showed reduced neovascularization compared with the anti-VEGF positive control.

These data demonstrate that an IL-6a, e.g., a monoclonal anti-IL-6 antibody, administered IVT can significantly reduce neovascularization in a mouse CNV model. The results further suggest that an anti-IL-6 antibody can produce a reduction in neovascularization at least as great, and possibly greater, than an anti-VEGF antibody. These data indicate that local inhibition of IL-6 is useful for treating eye diseases such as diseases involving vascular leakage, e.g., wet AMD or macular edema, e.g., diabetic macular edema.

Example 12: Development of an Improved IL-6 Antibody

Figure 5:
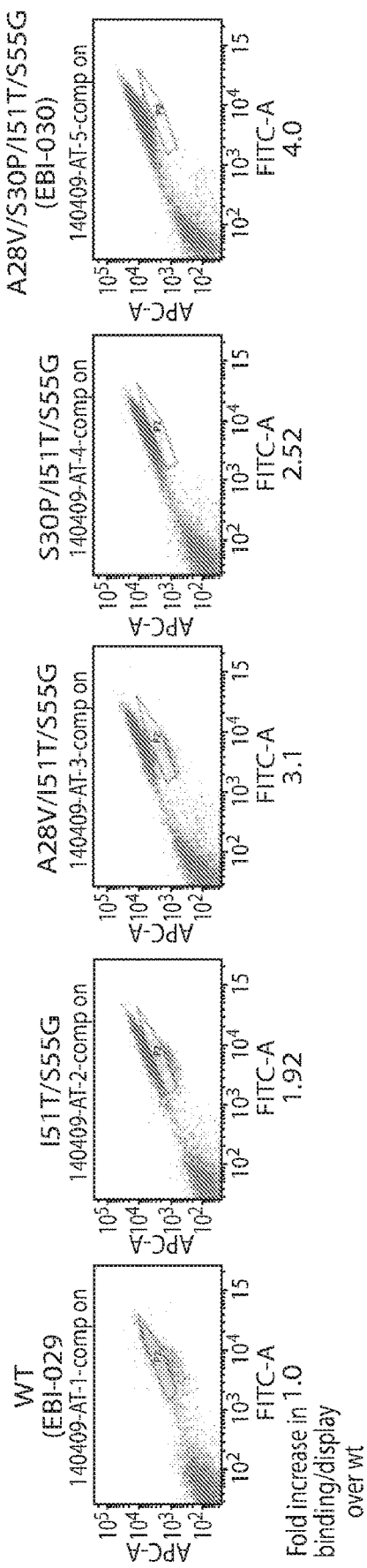
FIG. 5 shows the binding to IL-6, relative to the wild type antibody (EBI-029), in antibodies having the following mutations (1) I51T/S55G, (2) A28V/I51T/S55G, (3) S30P/I51T,/S55G, and (4) A28V/S30P/I51T/S55G (also referred to as EBI-030).

Variants of the EBI-029 antibody were generated. To better characterize the contribution of mutations A28V, S30P, I51T, and S55G, specific combinations were introduced into the wild-type EBI-029 Fab display vector and binding measured. The results are shown in FIG. 5. After overnight competition with 2 pM IL-6, all mutants had significantly higher levels of biotinylated IL-6 remaining on their cell surface relative to display compared to the wild-type EBI-029 Fab. The rank order of binding from highest to lowest affinity was A28V/S30P/I51T/S55G>A28V/I51T/S55G>S30P/I51T/S55G>I51T/S55G>wt. The quadruple mutation A28V/S30P/I51T/S55G is also referred to herein as EBI-030.

Sequences of EBI-030 are shown below.

```
030 CDR sequences:
CDR1 of 030HC (VH CDR1 030):
                                (SEQ ID NO: 31)
GYVLPNYLIE CDR2 of 030HC (VH CDR2 030):
                                (SEQ ID NO: 32)
VTTPGGGTIN CDR3 of 030HC (VH CDR3 030):
                                (SEQ ID NO: 33)
SRWDPLYYYALEY CDR1 of 030LC (VL CDR1 030):
                                (SEQ ID NO: 34)
RASESVDNYGIPFMN CDR2 of 030LC (VL CDR2 030):
                                (SEQ ID NO: 35)
AASNRGS CDR3 of 030LC (VL CDR3 030):
                                (SEQ ID NO: 36)
QQSEEVPLT 030 heavy chain variable region sequence
(mutations relative to 029 shown in bold):
                                (SEQ ID NO: 37)
QVQLVQSGAE VKKPGSSVKV SCKASGYVLP NYLIEWVRQA

PGQGLEWMGV TTPGGGTINY AQKFQGRVTI TADESTSTAY

MELSSLRSED TAVYYCARSR WDPLYYYALE YWGQGTTVTV SS 030 light chain variable region sequence:
                                (SEQ ID NO: 38)
DIVMTQSPDSLAVSLGERATINCRASESVDNYGIPFMNWYQQKPGQPPKL

LIYAASNRGSGVPDRFSGSGSGTDFTLTISSLQAEDVAVYYCQQSEEVPL

TFGQGTKLEIKRTV

030 Fab (IgG1) heavy chain polypeptide sequence
(CDRs underlined, mutations relative to 029
shown in bold):
                                (SEQ ID NO: 39)
QVQLVQSGAE VKKPGSSVKV SCKASGYVLP NYLIEWVRQA

PGQGLEWMGV TTPGGGTINY AQKFQGRVTI TADESTSTAY

MELSSLRSED TAVYYCARSR WDPLYYYALE YWGQGTTVTV

SSASTKGPSV FPLAPSSKST SGGTAALGCL VKDYFPEPVT

VSWNSGALTS GVHTFPAVLQ SSGLYSLSSV VTVPSSSLGT

QTYICNVNHK PSNTKVDKKV EPKSCDKTHT
```

In embodiments, the DKTHT sequence (SEQ ID NO:30) at the carboxy terminus of SEQ ID NO:39 is not included in the Fab sequence.

```
030 Fab heavy chain nucleic acid sequence:
                                      (SEQ ID NO: 40)
CAAGTGCAGCTGGTGCAGTCAGGGGCCGAGGTTAAGAAGCCAGGGAGCAG

CGTCAAGGTATCTTGTAAAGCGTCTGGTTACGTCCTTCCAAACTACCTGA

TCGAATGGGTGAGGCAGGCTCCCGGCCAAGGCCTGGAATGGATGGGAGTT

ACCACCCCTGGGGCGGCACCATTAATTACGCCCAGAAATTTCAGGGACG

AGTGACGATTACCGCCGACGAGTCCACCAGTACTGCCTACATGGAGCTGT

CCTCACTCCGCAGCGAGGACACGGCAGTTTACTACTGCGCCCGGAGTCGA

TGGGACCCTCTTTACTATTATGCTCTGGAATACTGGGGCCAGGGAACGAC

CGTTACAGTGTCATCTGCTAGCACAAAAGGACCATCAGTCTTCCCACTTG

CTCCTTCATCTAAGAGCACAAGTGGTGGCACTGCAGCCCTTGGCTGCCTG

GTGAAAGATTATTTCCCCGAACCTGTTACAGTTTCTTGGAACTCCGGTGC

ACTGACATCCGGAGTACACACTTTCCCAGCTGTGCTGCAGAGCTCAGGAC

TGTATAGCCTGTCTTCGGTGGTCACTGTTCCATCGTCGAGTCTTGGCACA

CAGACATATATTTGCAACGTCAATCACAAGCCCTCCAACACAAAAGTGGA

TAAGAAGGTCGAGCCCAAATCTTGTGACAAAACACACACA 030 can also be produced as an IgG2 Fab
heavy chain polypeptide sequence:
                                      (SEQ ID NO: 54)
QVQLVQSGAEVKKPGSSVKVSCKASGYVLPNYLIEWVRQAPGQGLEWMGV

TTPGGGTINYAQKFQGRVTITADESTSTAYMELSSLRSEDTAVYYCARSR

WDPLYYYALEYWGQGTTVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERK
```

Example 13: Expression and Purification of Variant Fab Fragments

VH domain inserts containing the following mutant combinations, A28V/I51T/S55G, S30P/I51T/S55G, and A28V/S30P/I51T/S55G (EBI-030), were generated from the yeast display vectors by double digest with BamHI-HF/NheI-HF. Inserts were purified by 1% agarose gel electrophoresis and ligated into a pTT5 derived mammalian expression vector containing a leader sequence, human IgG1 CH1 domain, and C-terminal His tag. Transformants were selected on LB-Amp, miniprepped, and the inserts confirmed by sequencing. Transient transfections were performed in HEK-6E cells (Canadian Research Council) for each mutant Fab heavy chain paired with the wild-type EBI-029 light chain (disclosed herein as SEQ ID NO:12) using PEI as a transfection reagent. The wild-type EBI-029 Fab was also expressed as a control (the wild-type Fab heavy chain is disclosed herein as SEQ ID NO:24). Supernatants were harvested after 5 days and the expressed Fabs purified by affinity chromatography using Ni-NTA agarose (Life Technologies). Purified protein was buffer exchanged into PBS, pH 7.4 by several rounds of concentration/dilution and protein concentration and purity determined by Absorbance 280 and SDS-PAGE.

Example 14: Variant Antibodies Showed Improved Binding as Assessed Using Surface Plasmon Resonance Affinities of the variant 029 Fab molecules for IL-6 were measured by Surface Plasmon Resonance (SPR) on a Reichert SR7000Dc Spectrometer. Human IL-6 at 20 µg/mL in 10 mM sodium acetate, pH 4.5 was immobilized on a 500-kDa carboxymethyl dextran chip via standard amine coupling. Serial dilutions of each Fab molecule in 10 mM HEPES, 150 mM NaCl, pH 7.3 were injected at 25° C. with a 25 L/min flow rate. After 4 minutes, loading was stopped and dissociation measured by flowing running buffer (10 mM HEPES, 150 mM NaCl, pH 7.3) for 5 minutes. Sensogram traces fit poorly to a 1:1 binding model, potentially due to mixed orientations of IL-6 on the chip or non-specific antibody binding: Instead, curves were fit to a 2 species (low affinity and high affinity species, labeled "low affinity" and "high affinity" in table 3) fit using TraceDrawer software where ka1, kd1, and KD1 are the association rate, dissociation rate, and equilibrium binding constant for the low affinity species, and ka2, kd2, and KD2 are the association rate, dissociation rate, and equilibrium binding constant for the high affinity species. All mutant Fabs had significantly slower dissociation compared to the wt EBI-029 Fab with the following rank order of highest to lowest affinity—A28V/S30P/I51T/S55G (EBI-030)>S30P/I51T/S55G>A28V/I51T/S55G>WT (EBI-029).

TABLE 3

SPR results for mutant antibodies

| Fab | ka1 ($*e^4$) | kd1 ($*e^{-4}$) | KD1 (nM) | ka2 ($*e^5$) | kd2 ($*e^{-4}$) | KD2 (nM) |
|---|---|---|---|---|---|---|
| WT | 5.48 | 6.08 | 11.1 | 2.94 | 4.27 | 1.45 |
| A28V/I51T/S55G | 8.06 | 2.91 | 3.6 | 3.65 | 1.45 | 0.40 |
| S30/I51T/S55G | 7.18 | 2.18 | 3.04 | 3.29 | 0.95 | 0.29 |
| A28V/S30P/I51T/S55G | 7.95 | 2.70 | 3.39 | 3.25 | 0.66 | 0.20 |

Low affinity | High affinity

Figure 6:
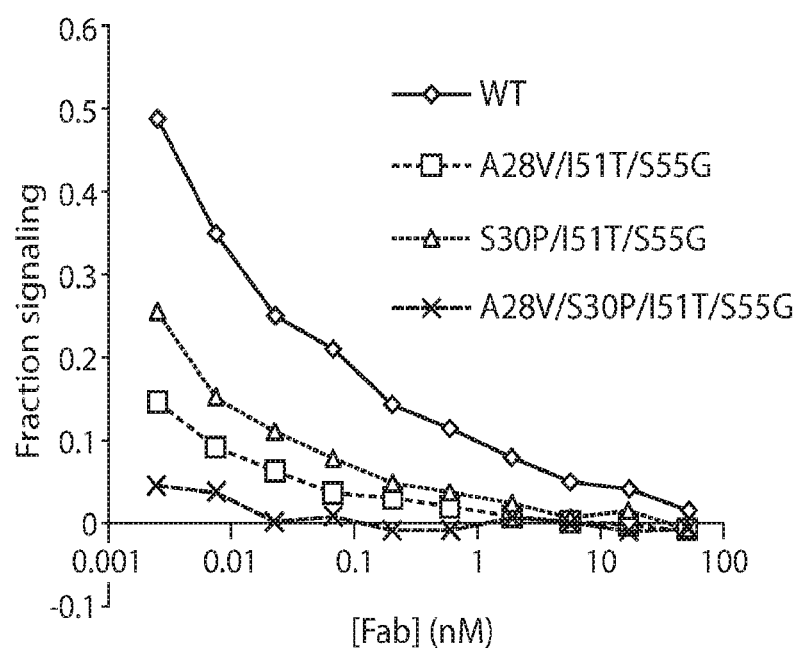
FIG. 6 shows the fractional signaling in HEK-Blue™ IL6 reporter cells treated with IL-6 and one of the following Fabs: (1) WT (EBI-029), (2) A28V/I51T/S55G, (3) S30P/I51T/S55G, (4) A28V/S30P/I51T/S55G (EBI-030).

Example 15: Variant Antibodies Showed Improved Antagonistic Potency in HEK-Blue™ IL6 Reporter Cells The HEK-Blue™ IL6 reporter cell line (Invivogen) was used to compare the potency of IL6 signaling inhibition between the different mutant EBI-029 Fab fragments. HEK-Blue™ IL6 cells are a modified HEK293 line stably expressing the IL-6R gene and containing a secreted alkaline phosphatase reporter gene under control of the IFNβ minimal promoter fused to four STAT3 binding sites. To measure IL6 antagonism, 10 µL of 400 pM human IL-6 (R&D Systems 206-IL-010/CF) was mixed with 10 µL of each Fab variant at a range of concentrations in a 96 well plate and incubated at RT for 30 minutes. HEK-Blue™ IL6 cells in log phase were trypsinized and resuspended in assay media (DMEM, 4.5 g/l glucose, 10% Heat inactivated FBS, 2 mM L-glutamine, Pen-Step) at 280,000 cells/mL. 180 µL of cell suspension was added to each well of IL-6/Fab mixtures to bring the final IL-6 concentration to 20 pM. The cells were incubated at 37° C./5% $CO_2$ for 20 hours. 20 µL of supernatant from each well was then mixed with 180 µL of Quanti-Blue™ reagent (Invivogen) and incubated at 37° C. for 40 minutes before measuring absorbance at 650 nM on a SpectraMax M5 plate reader. The background signal from wells with no IL-6 was subtracted and then divided by IL-6 treated cells with no inhibitor to derive a fractional signaling value. All mutants showed significantly greater potency compared to the wt EBI-029 Fab with the rank order of antagonistic potency as follows: A28V/S30P/I51T/S55G (EBI-030)>A28V/I51T/S55G>S30P/I51T/S55G>WT (EBI-029). These results are shown in FIG. 6.

Figure 7:
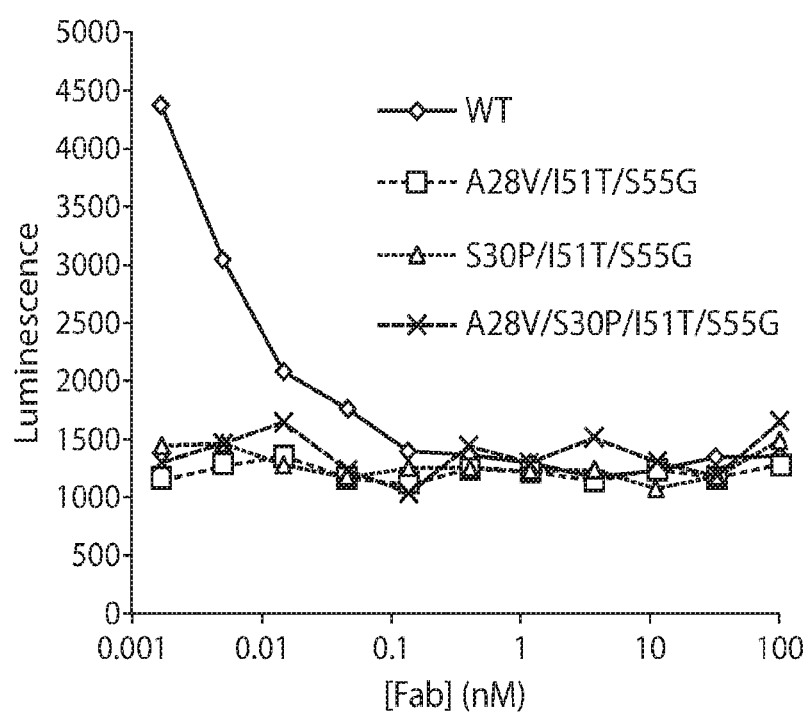
FIG. 7 shows the luminescence (a measure of IL-6 induced proliferation) in T1165.85.2.1 cells treated with IL-6 and one of the following Fabs at the concentration shown: (1) WT (EBI-029), (2) A28V/I51T/S55G, (3) S30P/I51T/S55G, (4) A28V/S30P/I51T/S55G (EBI-030).

Example 16: Variant Antibodies Showed Improved Antagonistic Potency in T1165 Proliferation Assay T1165.85.2.1 cells (R&D Systems) are a murine plasmacytoma cell line that proliferates in response to mouse, rat, or human IL-6. To measure antagonism from the EBI-029 Fab mutants, 25 µL of 2 ng/mL human IL-6 (R&D Systems 206-IL-010/CF) was mixed with 25 µL of each Fab variant at a range of concentrations in a 96 well plate and incubated at RT for 30 minutes. T1165 cells in log phase were pelleted and resuspended in assay media (90% RPMI 1640, 10% FBS, 2 mM L-glutamine, Pen-Strep) at 2×105 cells/mL. 50 L of cell suspension was added to each well of IL-6/Fab mixtures to bring the final IL-6 concentration to 0.5 ng/mL. The cells were incubated at 37° C./5% C02 for 72 hours. 100 µL of Cell-Titer Glo® reagent (Promega) was added to each well and incubated at RT for 10 minutes. Luminescence was measured on a SpectraMax M5 plate reader. All mutants showed significantly greater potency compared to the wt EBI-029 Fab with no measurable IL-6 signaling over the range of Fab concentrations tested (see FIG. 7).

Example 17: Drug Like Properties Comparison of Variant Antibodies

Thermal stability of each Fab variant was determined by differential scanning fluorimetry (DSF). 2 µL of protein at 2.5 or 5 mg/mL was mixed with 18 µL PBS and 2 µL of 50× Sypro Orange in a BioRad 96 well PCR plate. The plate was run in a BioRad CFX96 RT-PCR System with a linear temperature increase from 25° C. and 95° C. and fluorescence measured over time. The $T_m$ was calculated as the lowest point of the first derivative of the melt curve. All variants had measured $T_m$ values between 76 and 78° C., consistent with the measured $T_m$ of the wt EBI-029 Fab at 76° C.

To measure aggregation, samples were assessed by SEC-MALS using an Agilent 1260 HPLC combined with a Wyatt miniDawn TREOS light scattering instrument and Wyatt Optilab rEX refractive index instrument. 20-100 g of protein was injected and run at a flow rate of 1 mL/min. All variants had molecular weights between 45000 and 52000 Da as measured by light scattering, consistent with the wild-type EBI-029 Fab.

These results indicate that EBI-030 behaves similarly well compared with EBI-029 in terms of its drug like properties.

Example 18: Production of Full Length EBI-029 and EBI-030 IgG2 Antibodies and IgG2 Antibodies with Mutant Fc Domains Reformatting EBI-029 and EBI-030 to IgG2 and Mutant Fc IgG2

The heavy chain variable domains of EBI-029 and EBI-030 including the leader sequence (MDWTWRIL-FLVAAATGAHS; SEQ ID NO:49) were PCR amplified from the Fab vectors using primers that introduced an N-terminal EcoRI site and C-terminal NheI site. PCR products were purified on a 1% agarose gel and double digested with EcoRI-HF & NheI-HF. pTT5 based backbone vectors containing the wild-type IgG2 heavy chain sequence or a variant IgG2 domain with an H311 Å mutation (H311 corresponds to the numbering in SEQ ID NO:41; this corresponds to H310 in the numbering provided in Martin et al., Molecular Cell, 7:4, 867-877 (2001)) were similarly digested EcoRI-FH/NheI-HF and purified on a 1% agarose gel. Inserts were ligated into the digested backbone using Quikligase enzyme (New England Biolabs), transformed in TOP10 cells (Life Technologies), and selected on LB-Amp. Clones were miniprepped and sequenced to confirm the insert. The H311A mutation was selected to reduce Fc binding affinity for FcRn in order to reduce systemic accumulation of molecules that escape from the ocular tissue.

Expression and Purification of IgG2 Variants by Transient Transfection

EBI-029 IgG2, EBI-029 IgG2-H311A, EBI-030 IgG2, and EBI-030 IgG2-H311 Å were expressed by transient transfection in HEK-6E cells. pTT5 vectors containing each heavy chain were cotransfected with the EBI-029 LC plasmid using PEI as a transfection reagent. Supernatants were harvested after 5 days and the expressed IgG2 molecules purified by affinity chromatography using Protein-A agarose. Purified protein was buffer exchanged into PBS, pH 7.4 by several rounds of concentration/dilution and protein concentration and purity determined by Absorbance 280 and SDS-PAGE.

CHO Stable Pool Production

Stable CHO pools producing EBI-029 IgG2, EBI-030 IgG2, or EBI-030 IgG2-H311 Å were generated using the Freedom CHO-S kit (Life Technologies) according to manufacturer's instructions. In short, each heavy chain was cloned by standard digestion/ligation into the pCHO 1.0 vector in combination with the EBI-029 LC. Constructs were transfected into CHO-S cells using Freestyle MAX reagent and stable pools selected with increasing concentrations of Puromycin and MTX. Following two rounds of selection, pools were screened for antibody production by analytical Protein-A chromatography and the highest producers were selected for scale-up and subcloning.

Sequences are presented below.

```
030 Heavy chain polypeptide sequence (in
IgG2 framework, CDRs underlined):
                                    (SEQ ID NO: 41)
QVQLVQSGAE VKKPGSSVKV SCKASGYVLP NYLIEWVRQA

PGQGLEWMGV TTPGGGTINY AQKFQGRVTI TADESTSTAY

MELSSLRSED TAVYYCARSR WDPLYYYALE YWGQGTTVTV

SSASTKGPSV FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLMISRTPEV TCVVVDVSHE DPEVQFNWYV

DGVEVHNAKT KPREEQFNST FRVVSVLTVV HQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK
```

030 light chain polypeptide sequence (in IgG2 framework, CDRs underlined):
(SEQ ID NO: 42)
DIVMTQSPDS LAVSLGERAT INC<u>RASESVD NYGIPFMN</u>WY QQKPGQPPKL LIY<u>AASNRGS</u> GVPDRFSGSG SGTDFTLTIS SLQAEDVAVY YC<u>QQSEEVPL T</u>FGQGTKLEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC 030 heavy chain nucleic acid sequence:
SEQ ID NO: 43
CAAGTGCAGCTGGTGCAGTCAGGGGCCGAGGTTAAGAAGCCAGGGAGCAG

CGTCAAGGTATCTTGTAAAGCGTCTGGTTACGTCCTTCCAAACTACCTGA

TCGAATGGGTGAGGCAGGCTCCCGGCCAAGGCCTGGAATGGATGGGAGTT

ACCACCCCTGGGGGCGGCACCATTAATTACGCCCAGAAATTTCAGGGACG

AGTGACGATTACCGCCGACGAGTCCACCAGTACTGCCTACATGGAGCTGT

CCTCACTCCGCAGCGAGGACACGGCAGTTTACTACTGCGCCCGGAGTCGA

TGGGACCCTCTTTACTATTATGCTCTGGAATACTGGGGCCAGGGAACGAC

CGTTACAGTGTCATCTGCTAGCACCAAGGGCCCATCGGTCTTCCCCCTGG

CGCCCTGCTCCAGGAGCACCTCCGAGAGCACAGCGGCCCTGGGCTGCCTG

GTCAAGGACTACTTCCCCGAACCGGTGACGGTGTCGTGGAACTCAGGCGC

TCTGACCAGCGGCGTGCACACCTTCCCGGCTGTCCTACAGTCCTCAGGAC

TCTACTCCCTCAGCAGCGTGGTGACCGTGCCCTCCAGCAACTTCGGCACC

CAGACCTACACCTGCAACGTAGATCACAAGCCCAGCAACACCAAGGTGGA

CAAGACAGTTGAGCGCAAATGTTGTGTCGAGTGCCCACCGTGCCCAGCAC

CACCTGTGGCAGGACCGTCAGTCTTCCTCTTCCCCCCAAAACCCAAGGAC

ACCCTCATGATCTCCCGGACCCCTGAGGTCACGTGCGTGGTGGTGGACGT

GAGCCACGAAGACCCCGAGGTCCAGTTCAACTGGTACGTGGACGGCGTGG

AGGTGCATAATGCCAAGACAAAGCCACGGGAGGAGCAGTTCAACAGCACG

TTCCGTGTGGTCAGCGTCCTCACCGTCGTGCACCAGGACTGGCTGAACGG

CAAGGAGTACAAGTGCAAGGTCTCCAACAAAGGCCTCCCAGCCCCCATCG

AGAAAACCATCTCCAAAACCAAAGGGCAGCCCCGAGAACCACAGGTGTAC

ACCCTGCCCCCATCCCGGGAGGAGATGACCAAGAACCAGGTCAGCCTGAC

CTGCCTGGTCAAAGGCTTCTACCCCAGCGACATCGCCGTGGAGTGGGAGA

GCAATGGGCAGCCGGAGAACAACTACAAGACCACACCTCCCATGCTGGAC

TCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGC

ACAACCACTACACGCAGAAGAGCCTCTCCCTGTCTCCGGGTAAA 030 light chain nucleic acid sequence:
SEQ ID NO: 44
GACATAGTGATGACTCAAAGTCCGGACAGCCTGGCGGTGTCACTCGGCGA

ACGGGCAACTATCAACTGCCGAGCCAGCGAGAGCGTCGATAATTACGGCA

TCCCCTTCATGAACTGGTATCAGCAGAAGCCAGGACAGCCGCCCAAGCTG

CTTATCTACGCCGCTTCCAACCGGGGATCAGGGGTGCCCGATCGATTTAG

TGGAAGCGGTAGTGGGACCGATTTCACACTGACCATCAGCTCCCTTCAGG

CCGAGGATGTGGCTGTCTATTATTGTCAGCAATCCGAGGAAGTGCCGCTC

ACGTTTGGTCAGGGAACCAAACTGGAGATCAAGCGGACCGTAGCGGCGCC

TAGTGTCTTCATCTTCCCACCCTCCGACGAACAGCTGAAGTCTGGCACTG

CTTCCGTCGTGTGCCTGCTCAACAACTTTTACCCTAGAGAGGCAAAAGTT

CAATGGAAAGTAGACAATGCCTTGCAGTCCGGGAACTCCCAGGAGTCTGT

CACAGAGCAGGATAGTAAGGACTCAACCTACAGCCTGTCCAGCACACTGA

CCCTCTCCAAAGCCGACTACGAGAAGCACAAAGTGTACGCTTGCGAAGTT

ACGCATCAGGGGCTGTCCTCACCCGTTACAAAAAGTTTTAACAGAGGGGA

GTGC

030 Heavy chain polypeptide sequence with the H311A mutation (311A is boldface and CDRs are underlined), also referred to herein as the 031 heavy chain polypeptide sequence:
(SEQ ID NO: 47)
QVQLVQSGAE VKKPGSSVKV SCKAS<u>GYVLP NYLIE</u>WVRQA PGQGLEWMGV <u>TTPGGGTINY</u> AQKFQGRVTI TADESTSTAY MELSSLRSED TAVYYCARS<u>R WDPLYYYALE Y</u>WGQGTTVTV

SSASTKGPSV FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLMISRTPEV TCVVVDVSHE DPEVQFNWYV

DGVEVHNAKT KPREEQFNST FRVVSVLTVV AQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK 031 heavy chain nucleic acid sequence:
(SEQ ID NO: 48)
CAAGTGCAGCTGGTGCAGTCAGGGGCCGAGGTTAAGAAGCCAGGGAGCAG

CGTCAAGGTATCTTGTAAAGCGTCTGGTTACGTCCTTCCAAACTACCTGA

TCGAATGGGTGAGGCAGGCTCCCGGCCAAGGCCTGGAATGGATGGGAGTT

ACCACCCCTGGGGGCGGCACCATTAATTACGCCCAGAAATTTCAGGGACG

AGTGACGATTACCGCCGACGAGTCCACCAGTACTGCCTACATGGAGCTGT

CCTCACTCCGCAGCGAGGACACGGCAGTTTACTACTGCGCCCGGAGTCGA

TGGGACCCTCTTTACTATTATGCTCTGGAATACTGGGGCCAGGGAACGAC

CGTTACAGTGTCATCTGCTAGCACCAAGGGCCCATCGGTCTTCCCCCTGG

CGCCCTGCTCCAGGAGCACCTCCGAGAGCACAGCGGCCCTGGGCTGCCTG

GTCAAGGACTACTTCCCCGAACCGGTGACGGTGTCGTGGAACTCAGGCGC

TCTGACCAGCGGCGTGCACACCTTCCCGGCTGTCCTACAGTCCTCAGGAC

TCTACTCCCTCAGCAGCGTGGTGACCGTGCCCTCCAGCAACTTCGGCACC

CAGACCTACACCTGCAACGTAGATCACAAGCCCAGCAACACCAAGGTGGA

CAAGACAGTTGAGCGCAAATGTTGTGTCGAGTGCCCACCGTGCCCAGCAC

CACCTGTGGCAGGACCGTCAGTCTTCCTCTTCCCCCCAAAACCCAAGGAC

-continued
ACCCTCATGATCTCCCGGACCCCTGAGGTCACGTGCGTGGTGGTGGACGT

GAGCCACGAAGACCCCGAGGTCCAGTTCAACTGGTACGTGGACGGCGTGG

AGGTGCATAATGCCAAGACAAAGCCACGGGAGGAGCAGTTCAACAGCACG

TTCCGTGTGGTCAGCGTCCTCACCGTCGTGGCCCAGGACTGGCTGAACGG

CAAGGAGTACAAGTGCAAGGTCTCCAACAAAGGCCTCCCAGCCCCCATCG

AGAAAACCATCTCCAAAACCAAAGGGCAGCCCCGAGAACCACAGGTGTAC

ACCCTGCCCCCATCCCGGGAGGAGATGACCAAGAACCAGGTCAGCCTGAC

CTGCCTGGTCAAAGGCTTCTACCCCAGCGACATCGCCGTGGAGTGGGAGA

GCAATGGGCAGCCGGAGAACAACTACAAGACCACACCTCCCATGCTGGAC

TCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGC

ACAACCACTACACGCAGAAGAGCCTCTCCCTGTCTCCGGGTAAA

Example 19: EBI-030 vs. EBI-029 IgG2 Potency Comparison in HEK-Blue-IL6 Assay The HEK-Blue™ IL6 reporter cell line (Invivogen) was used to compare the potency of IL6 signaling inhibition between EBI-029 and EBI-030 IgG2 antibodies. Three protein preps purified from HEK-6E cells were compared—EBI-029 IgG2, EBI-030 IgG2, and EBI-030 IgG2-H311Å (also referred to as 031 or EBI-031), along with a prep of EBI-030 IgG2 produced in a stable CHO pool. Additionally, Tocilizumab, an approved anti-IL6R antibody, was included as a control. To measure IL6 antagonism, human IL-6 (R&D Systems 206-IL-010/CF) at 400 pM was mixed with varying concentrations of each antibody in a 96 well plate and incubated at RT 30 for 30 minutes. HEK-Blue™ IL6 cells in log phase were trypsinized and resuspended in assay media (DMEM, 4.5 g/l glucose, 10% Heat inactivated FBS, 2 mM L-glutamine, Pen-Step) at 280,000 cells/mL. 180 µL of cell suspension was added to each well of IL-6/Fab mixtures to bring the final IL-6 concentration to 20 pM. The cells were incubated at 37° C./5% $CO_2$ for 20 hours. 20 µL of supernatant from each well was then mixed with 180 µL of Quanti-Blue™ reagent (Invivogen) and incubated at 37° C. for 40 minutes before measuring absorbance at 650 nM on a SpectraMax M5 plate reader.

Figure 8:
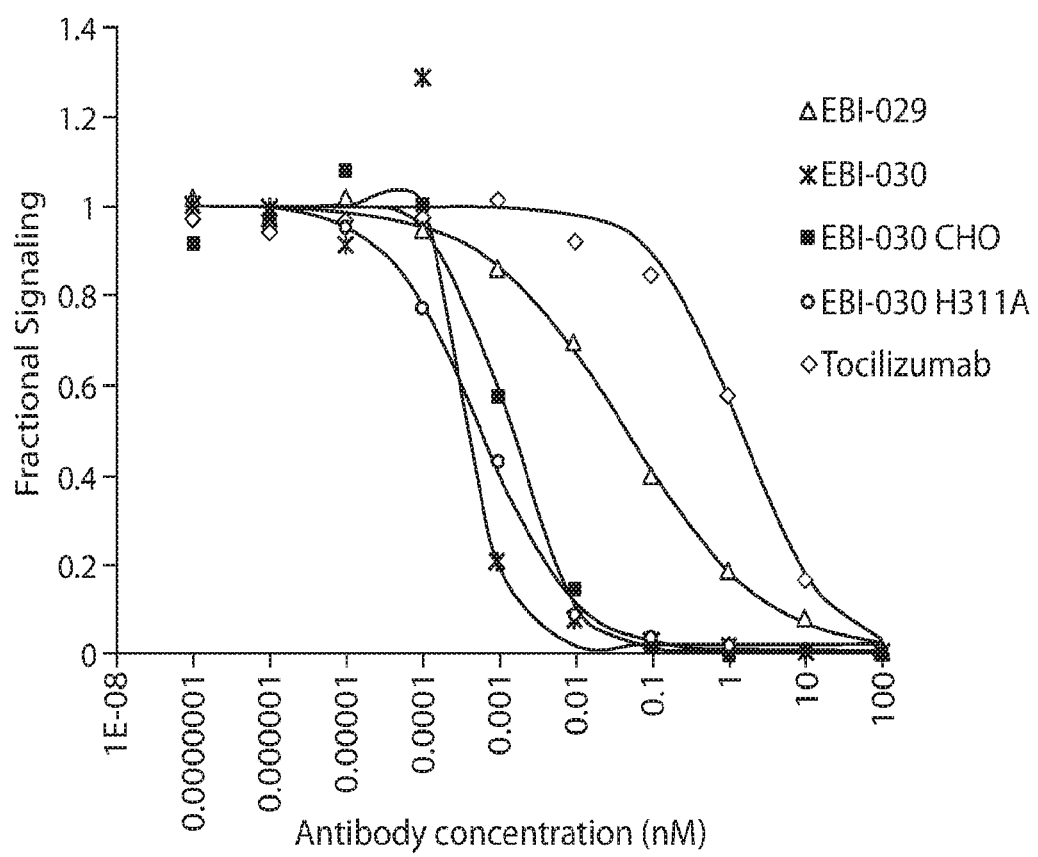
FIG. 8 shows fractional signaling in HEK-Blue™ IL6 reporter cells treated with 20 pM IL-6 and various concentrations of (1) EBI-029 IgG2 (EBI029) produced in HEK-6E cells, (2) EBI-030 IgG2 (EBI030) produced in HEK-6E cells, and (3) EBI-030 IgG2-H311A (EBI030 H311A) produced in HEK-6E cells; (4) tocilizumab (TOCI), and (5) EBI-030 IgG2 produced in a stable CHO pool (EBI-030 CHO).

The results are shown in FIG. 8 and in Table 5. EBI-030 (including EBI-030 produced in HEK cells with or without the H311Å mutation and EBI-030 produced in CHO cells) showed greatly improved potency (about a 50 fold decrease in IC50 and >100 fold decrease in IC90) compared with EBI-029. The increase in potency was greater than the increase in affinity measured by SPR.

TABLE 5

| | IC50 and IC90 values | |
|---|---|---|
| | IC50 (pM) | IC90 (pM) |
| EBI-029 | 47 | 4350 |
| EBI-030 | 0.9 | 1.1 |
| EBI-030 CHO | 1.4 | 11 |
| EBI-030-H311A | 0.6 | 12.4 |
| Tocilizumab | 1490 | 23700 |

EBI-031 (also referred to herein as EBI-030 IgG2-H311A) had an IC50 more than 75 fold less than that of EBI-029 and an IC90 about 350 fold less than that of EBI-029. EBI-030 produced in HEK cells had an IC50 more than 50 fold less than that of EBI-029 and an IC90 approximately 4000 fold less than that of EBI-029.

Figure 9:
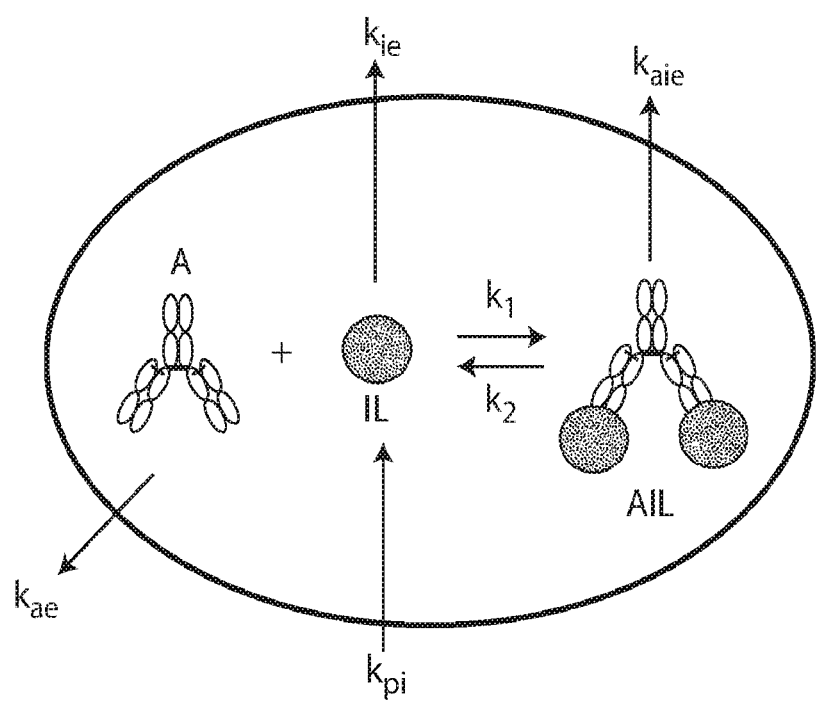
FIG. 9 depicts the pharmacokinetic model described in Example 20.

Example 20: Modeling Analysis of Increased Potency on Duration of Vitreal IL-6 Blockade The effect of increased potency on the extent and duration of IL-6 blockade following intravitreal administration was simulated using a pharmacokinetic model (FIG. 9). Differential equations describing changes in free antibody (A), free IL-6 (IL), and the antibody/IL-6 complex (AIL) were defined as follows:

$$d/dt(A) = -A*kae - A*IL*k1 + AIL*k2$$

$$d/dt(IL) = kpi - IL*kie - A*IL*k1 + AIL*k2$$

$$d/dt(AIL) = -AIL*kaie + A*IL*k1 - AIL*k2$$

where kae is the rate of free antibody clearance from the vitreous, k1 is the association rate for antibody/IL-6 binding, k2 is the dissociation rate for the antibody/IL6 complex, kpi is the rate of IL-6 production, kei is the rate of free IL-6 clearance from the vitreous, and kaie is the rate of antibody/IL-6 complex clearance from the vitreous. Starting parameter values and rates were defined as shown in Table 6.

TABLE 6

| Starting parameter values and rates | |
|---|---|
| Parameter | Value |
| Initial antibody concentration - $A_0$ | 3000 nM |
| Initial IL-6 concentration - $IL_0$ | 0.01 nM |
| Initial complex concentration - $AIL_0$ | 0 |
| Association rate - k1 | 8.64 $nM^{-1}d^{-1}$ |
| Dissociation rate - k2 | Varied from 0.0086 $d^{-1}$ to 0.86 $d^{-1}$ |
| Antibody clearance rate - kae | 0.037 $d^{-1}$ |
| IL6 clearance rate - kie | 0.69 $d^{-1}$ |
| IL6 production rate - kpi | 0.0069 nM $d^{-1}$ |
| Complex clearance rate - kaie | 0.037 $d^{-1}$ |

$A_0$ was calculated based on the assumptions of a 50 µL dose of 50 mg/mL antibody into a human eye with a 5 mL vitreal volume. $IL_0$ was estimated based on clinically measured values for vitreal IL-6 in DME patients of ~200 µg/mL. k1 was estimated based on typical antibody association rates of $1E5\ M^{-1}s^{-1}$, while k2 was varied to simulate potency values ranging from 100 pM to 1 pM. kae was derived from measured vitreal clearance half-times in the rabbit of ~11 days scaled by 1.8 as previously measured for human PK. kie was estimated at a clearance half time of 24 hours, and kpi was calculated as $IL_0*kie$.

Figure 10:
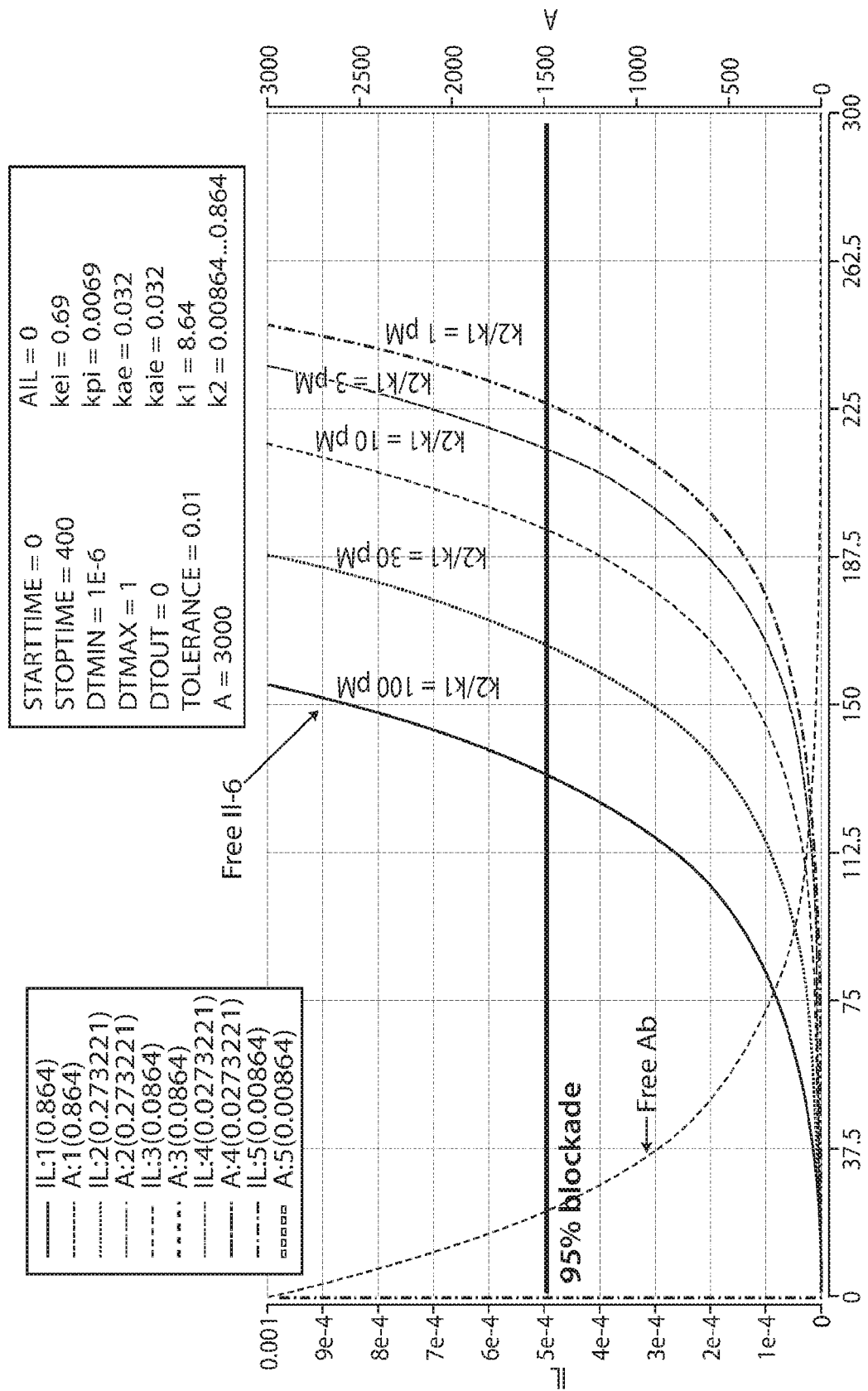
FIG. 10 depicts the effect of increasing antibody potency on the duration of IL-6 inhibition in the eye, as simulated using the pharmacokinetic model described in Example 20.

Simulations of free antibody and free IL-6 were performed using Berkeley Madonna software over a 300 day time course (FIG. 10). A cut-off of 95% IL-6 blockade was selected to measure duration of inhibition. The model predicts that increasing the antibody potency significantly extends the duration of IL-6 inhibition in the eye from 130 days for k2/k1=100 pM to 200 days for k2/k1=10 pM to 225 days for k2/k1=1 pM.

Example 21: Pharmacokinetics of IL-6a

Pharmacokinetic (PK) experiments were performed in male New Zealand White Rabbits by PharmOptima (Portage, Mich.). All animals were 12-13 months of age and weighed 2.61-3.42 kg. The following proteins were compared—EBI-029-IgG2 (SEQ ID NO:11 and SEQ ID NO:12), EBI-029-IgG2-H311 Å (SEQ ID NO:10 and SEQ ID NO:12), EBI-030 (SEQ ID NO:41 and SEQ ID NO:42), EBI-030-IgG2-H311 Å (SEQ ID NO:47 and SEQ ID NO:42), EBI-029 Fab (SEQ ID NO:24 and SEQ ID NO:12), Eylea® (VEGF trap), and Tocilizumab (TCZ; anti-IL6R antibody). All proteins were formulated at 13.8 mg/mL in PBS, pH 7.4. EBI-029-IgG2, EBI-029-IgG2-H311A, EBI-030, EBI-030-IgG2-H311A, EBI-029 Fab, and Tocilizumab do not bind to their target antigens in the rabbit, while Eylea® does bind to rabbit VEGF.

For the investigation of intravitreal PK, 9 animals were injected with 50 µL of test article in each eye. Prior to injection, Lidocaine hydrochloride (injectable 2%), 0.5% Proparacaine, or 0.5% Tetracaine was applied to the ocular surface. Injections were performed into the mid-vitreous with a BD 300 µL insulin syringe (31G×⅝₁₆ inch needle) inserted through the dorsotemporal quadrant of the eye. For the investigation of systemic PK, 3 animals were injected with 100 µL of test article through the ear vein.

Serial blood samples were collected from 3 animals in both the IVT and iv arms at 0.083, 1, 4, 8, 24, 72, 168, 240, and 336 hours and diluted 1:1 with Citrate-Phosphate-Dextrose solution and placed on ice. Plasma was harvested by centrifugation of the chilled blood samples at 4000 rpm for 10 minutes at 4° C. and stored frozen at −80° C.

Ocular tissues were harvested from both eyes of all animals in the IVT arm at 0.25, 24, 168, and 336 hours post dose. Animals were euthanized via intravenous barbiturate overdose. To harvest aqueous humor, immediately following euthanasia, a syringe with needle was inserted under the cornea and the aqueous humor slowly withdrawn. Aqueous humor was transferred to a pre-labeled tube and placed on dry ice or frozen at −80° C. To harvest vitreous humor, a small slice was introduced in the sclera of an enucleated eye using a scalpel and vireous was withdrawn through the opening via syringe. The sample was measured via the graduations on the syringe, transferred into a pre-labeled tube, and placed on dry ice or frozen at −80° C.

To harvest retina and choroid, a small slice was introduced with a scalpel in the sclera of an enucleated eye, parallel and caudal to the limbus. Scissors were used to continue the opening around the globe of the eye, separating it into two halves. The posterior globe was positioned so that the interior was facing upward. Using a gill knife, retina was carefully collected from the globe. Once retina was collected from the globe, choroid was collected in a similar manner from the remaining globe. Both samples, separately, were transferred to pre-weighed and pre-labeled Precellys® tubes, weighed, and placed on dry ice or frozen at −80° C. Retina and choroid tissues were diluted ten-fold in Phosphate Buffered Saline (PBS), homogenized, and stored at −80° C.

Protein concentrations in each tissue were assessed by ELISA. For EBI-029-IgG2, EBI-029-IgG2-H311A, EBI-030, EBI-030-IgG2-H311A, and EBI-029 Fab, Costar half-volume plates were coated with 1 µg/mL human IL-6 in PBS for 1 hour at RT. Wells were blocked with PBS containing 2% BSA, washed, and then incubated with a range of dilutions for each sample using PBS+5% rabbit plasma+0.05% Tween-20 as the diluent. A standard curve using purified protein was also included on each plate. Samples were incubated at RT for 60 minutes then washed three times with 300 µl PBS containing 0.05% Tween-20. Anti-kappa-HRP (Genway Inc.) diluted 1:10,000 in PBS, 1% BSA, 0.05% Tween-20 was then added to each well and incubated for 30 minutes. Wells were washed as above then 3,3',5,5'-tetramethylbenzidine (TMB) substrate was added and the signal measured at 450 and 550 nm on a Spectramax plate reader. Protein concentrations were calculated based on the standard curve using Softmax Pro 6 software. Each ELISA was repeated on at least 3 independent plates and the average half-time was reported.

For tocilizumab, protein concentrations were determined by ELISA as above except that anti-Tocilizumab Fab (Bio-Rad HCA252) was used as the capture reagent and anti-human-IgG-Fc-HRP (Sigma A0170) was used as the detection antibody. Two different ELISA assays were used to measure free and total Eylea®. For free Eylea®, wells were coated with recombinant VEGF (R&D Systems) and bound protein was detected with anti-human-IgG-Fc-HRP (Sigma A0170). For measuring total Eylea®, anti-human Fc antibody (Sigma 12136) was used for capture and anti-human IgG-CH2-HRP (BioRad MCA647P) was used for detection. Each ELISA was repeated on at least 3 independent plates and the average half-time was reported.

Summary of Results

Figure 11:
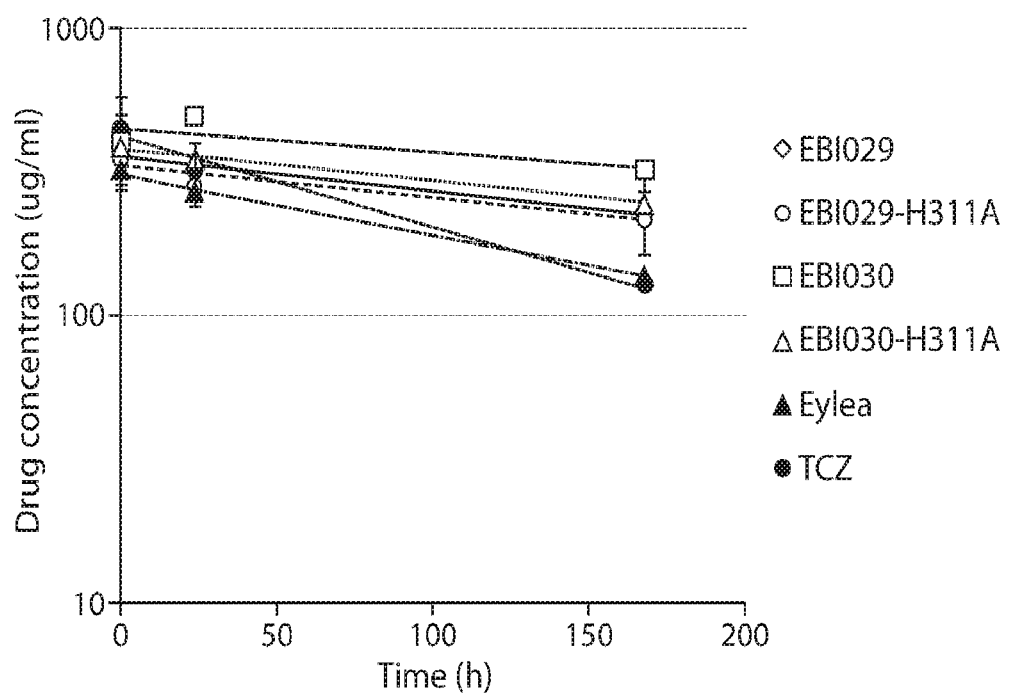
FIG. 11 shows the drug concentration of EBI-029, EBI-029-H311A, EBI-030, EBI-030-H311A, Eylea®, and tocilizumab (TCZ) in the vitreous over time following intravitreal administration.
Figure 12:
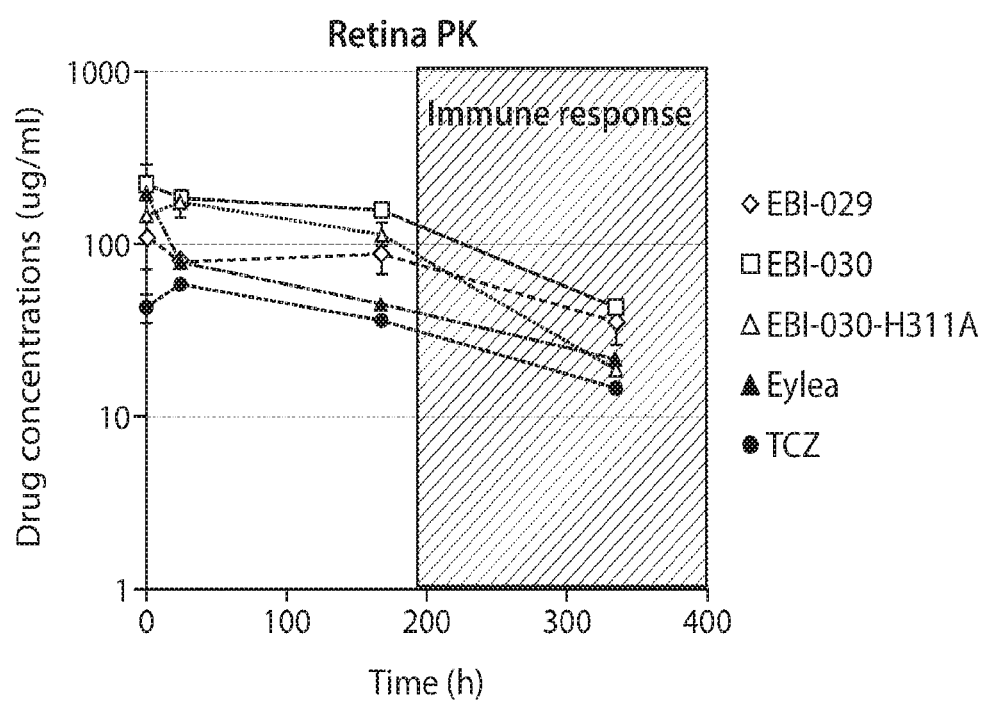
FIG. 12 shows the drug concentration of EBI-029, EBI-030, EBI-030-H311A, Eylea®, and tocilizumab (TCZ) in the retina over time following intravitreal administration.
Figure 13:
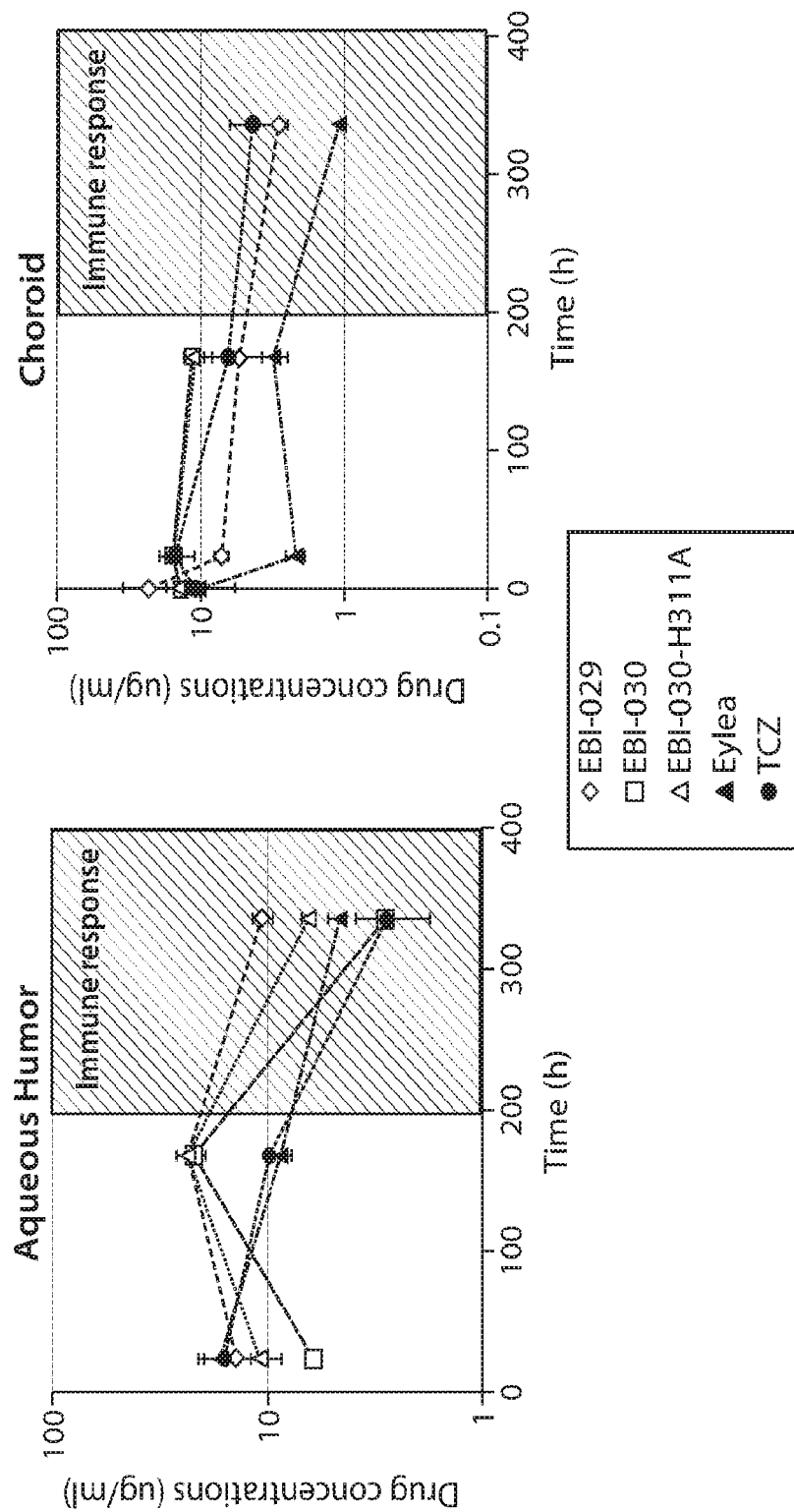
FIG. 13 shows the drug concentration of EBI-029, EBI-030, EBI-030-H311A, Eylea®, and tocilizumab (TCZ) in the aqueous humor over time following intravitreal administration.
Figure 14:
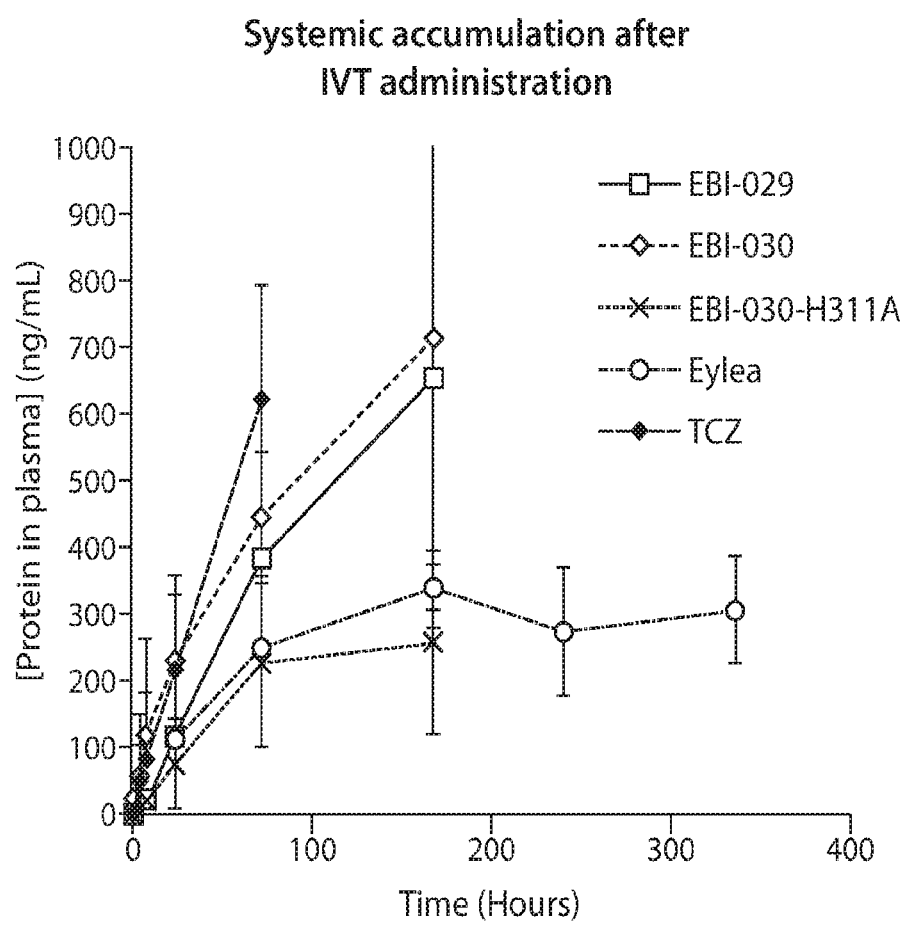
FIG. 14 shows the drug concentration of EBI-029, EBI-030, EBI-030-H311A, Eylea®, and tocilizumab (TCZ) in the choroid over time following intravitreal administration.
Figure 15B:
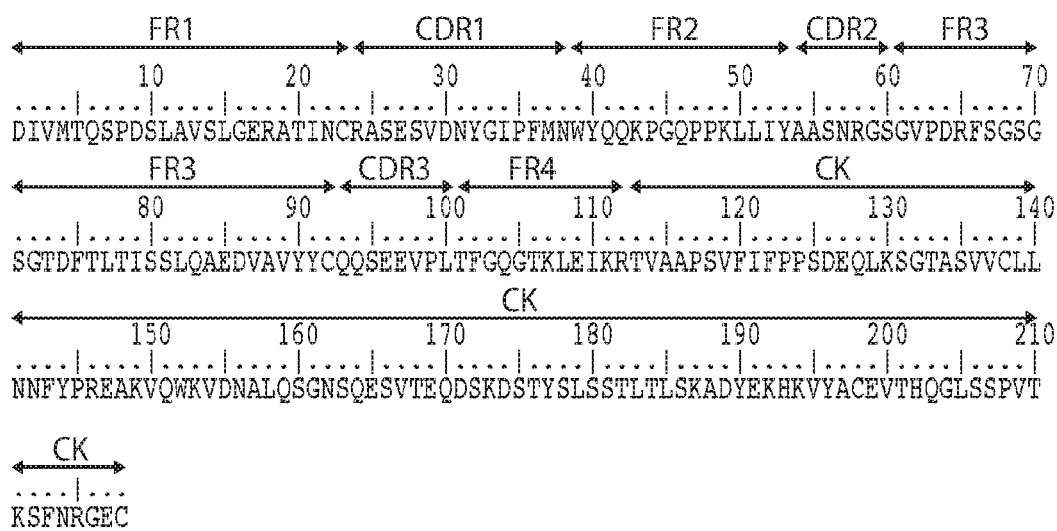
FIG. 15B depicts the locations of FR1, CDR1, FR2, CDR2, FR3, CDR3, FR4, and CK in light chain sequence (EBI-029, EBI-030 and EBI-031 have the same light chain sequence) (SEQ ID NO: 12).

In most animals, robust antibody formation against the injected protein was observed at the 240 and 336 hour timepoints. Because this antibody formation may affect protein clearance or interfere with the ELISA, data analysis was limited to the time points up to and including 168 hours. For intravitreal PK, all of the EBI-029 and EBI-030 IgG2 proteins were cleared significantly more slowly ($T_{1/2}$=9.3, 9.0, 15.7, and 9.8 days for EBI-029, EBI-029-H311A, EBI-030, and EBI-030-H311A, respectively) compared to Eylea® ($T_{1/2}$=6.3 days), Tocilizumab (T/2=4.8 days), or the EBI-029 Fab fragment ($T_1/2$=3.9 days) (FIG. 11, Table 7). Similar trends were observed in the retina, choroid, and aqueous where EBI-030 and EBI-030-H311 Å accumulated at higher levels compared to Eylea® and Tocilizumab (see FIG. 12 and FIG. 13). All proteins were detectable in the plasma following IVT administration with EBI-029, EBI-030, and Tocilizumab accumulating at significantly higher levels than Eylea® or EBI-030-H311 Å (see FIG. 14). Similarly, Eylea® and EBI-030-H311 Å were cleared more quickly from the plasma following IV administration, with the EBI-030-H311 Å half-time approximately half that of the wild-type IgG2 due to reduced FcRn binding (Table 7).

TABLE 7

Pharmacokinetic results

| Vitreous PK | |
|---|---|
| Molecule | $T_{1/2}$ (days) |
| EBI-029 | 9.3 |
| EBI-029-H311A | 9.0 |
| EBI-030 | 15.7 |
| EBI-030-H311A | 9.8 |
| EBI-029 Fab | 3.9 |
| Eylea ® | 6.1 (free), 6.3 (total) |
| Tocilizumab | 4.8 |

| Systemic PK after IV administration | |
|---|---|
| Molecule | $T_{1/2\beta}$ (hours) |
| EBI-029 | 77 |
| EBI-030 | 69 |
| EBI-030-H311A | 33 |
| Eylea ® | 37 (free), 42 (total) |
| TCZ | 50 |

Example 22: EBI-031 Solubility at High Concentrations

Purified EBI-031 was concentrated from 3 mg/mL to 142 mg/mL in PBS, pH 7.4 using an Amicon Ultra-15 spin concentrator. The pre- and post-concentration preps were assessed for aggregation by running on a Tosoh G3000SWXL 7.8×30 SEC column combined with a Wyatt miniDawn TREOS light scattering instrument and Wyatt Optilab rEX refractive index instrument. 20 µg of protein was injected and run at a flow rate of 1 mL/min in PBS. The mass fraction for the peak at the expected molecular weight of ~150 kDa was approximately equal for the two concentrations (90.9% for the 3 mg/mL and 91.3% for the 142 mg/mL prep) indicating that there was no significant increase in protein aggregation during concentration. These results demonstrate that EBI-031 can be concentrated to up to 142 mg/mL with little measurable aggregation (<10% aggregation).

Example 23: EBI-031 Blocks Cis- and Trans-IL6 Signaling

Figure 16A:
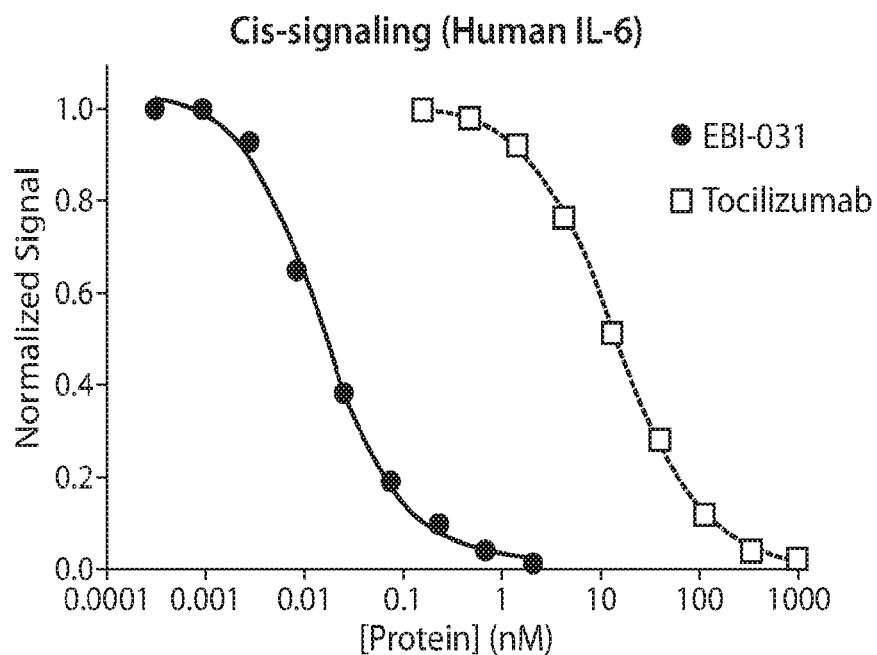
FIG. 16A shows the fractional signaling in HEK-Blue™ IL-6 reporter cells treated with 20 pM IL-6 and various concentrations of EBI-031 or tocilizumab.

The HEK-Blue™ IL6 reporter cell line (Invivogen) was used to compare the potency of EBI-031 and tocilizumab for blocking cis- and trans-IL6 signaling. For cis-signaling, free IL-6 (final concentration=20 pM) was mixed with EBI-031 or tocilizumab at a range of concentrations in a 96 well plate and incubated at RT for 30 minutes. HEK-Blue™ IL6 cells in log phase were trypsinized and resuspended in assay media (DMEM, 4.5 g/l glucose, 10% Heat inactivated FBS, 2 mM L-glutamine, Pen-Step), and 50,000 cells were added to each well in a final volume of 200 µL. Plates were incubated at 37° C./5% $CO_2$ for 20 hours. 50 µL of supernatant from each well was then mixed with 150 µL of Quanti-Blue™ reagent (Invivogen) and incubated at 37° C. for 40 minutes before measuring absorbance at 650 nM on a SpectraMax M5 plate reader. The background signal from wells with no IL-6 was subtracted and then divided by IL-6 treated cells with no inhibitor to derive a fractional signaling value. EBI-031 (IC50=14.2 pM) blocks free IL-6 with >900 fold greater potency compared to tocilizumab (IC50=12.9 nM) (FIG. 16A).

Figure 16B:
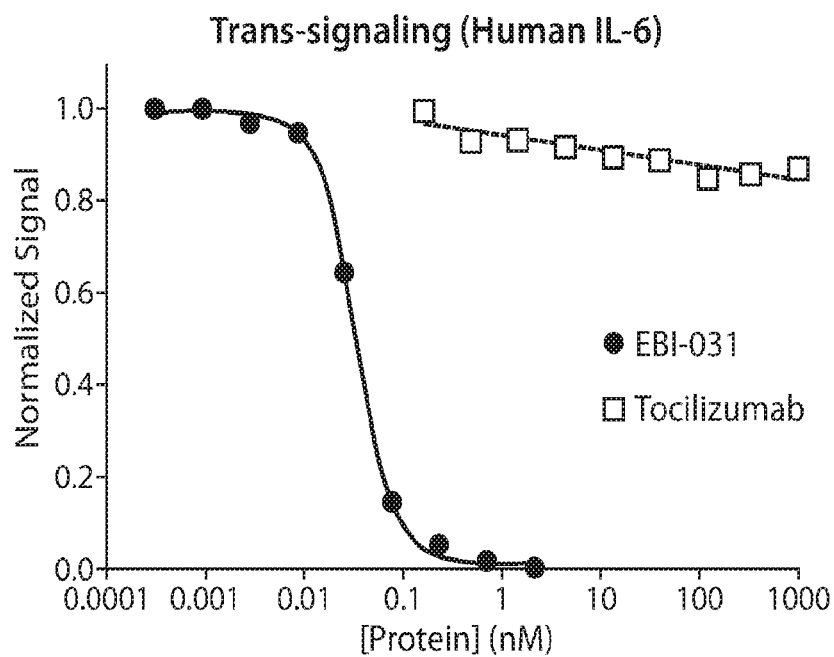
FIG. 16B shows the fractional signaling in HEK-Blue™ IL-6 reporter cells treated with 200 pM hyper IL-6 and various concentrations of EBI-031 or tocilizumab.

To measure trans-signaling blockade, experiments were performed as above except using hyper IL-6 at a final concentration of 200 pM instead of free IL-6. Hyper IL-6 is a genetic fusion between IL-6 and the soluble IL-6 receptor (Fischer et al., Nature Biotechnology 15:142-145 (1997). EBI-031 blocked hyper IL-6 potently (IC50=32 pM), while tocilizumab was unable to significantly inhibit signaling out to a 1 pM concentration (FIG. 16B).

These results show that EBI-031 binds human IL-6 at site 11, or the site that contacts gp130, with pM affinity and blocks signaling of IL-6 and the IL-6/sIL-6Rα complex in cellular assays >900 fold more potently than tocilizumab.

Figure 17:
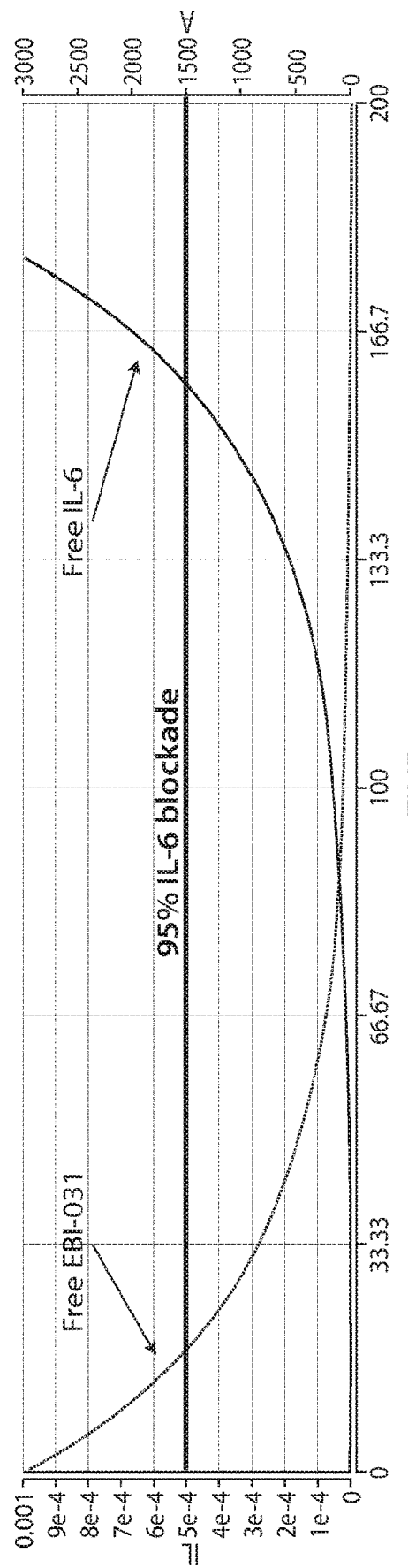
FIG. 17 shows results of computational simulations described in Example 24.

Example 24: Computational Simulations for Intravitreal EBI-031 Suppression of IL-6 Signaling Computational simulations were performed as described in Example 20 to predict the length of time that an intravitreal administration of EBI-031 in humans should suppress 95% of IL-6 signaling. k2 was set to 0.12 d−1 such that k2/k1=14 pM as measured in the potency assay. T1/2 clearance was set to 18 days based on the measured intravitreal clearance half-time in rabbits scaled by 1.8 for humans. All other parameters are described in Table 6. The model predicts that EBI-031 should block 95% of IL-6 signaling for ~150 days after intravitreal administration (FIG. 17). These modeling results indicate that EBI-031 can substantially block IL-6 signaling in the eye for a long period of time, e.g., up to about 6 months.

Example 25: Characterization of EBI-031 Isoforms

Figure 18:
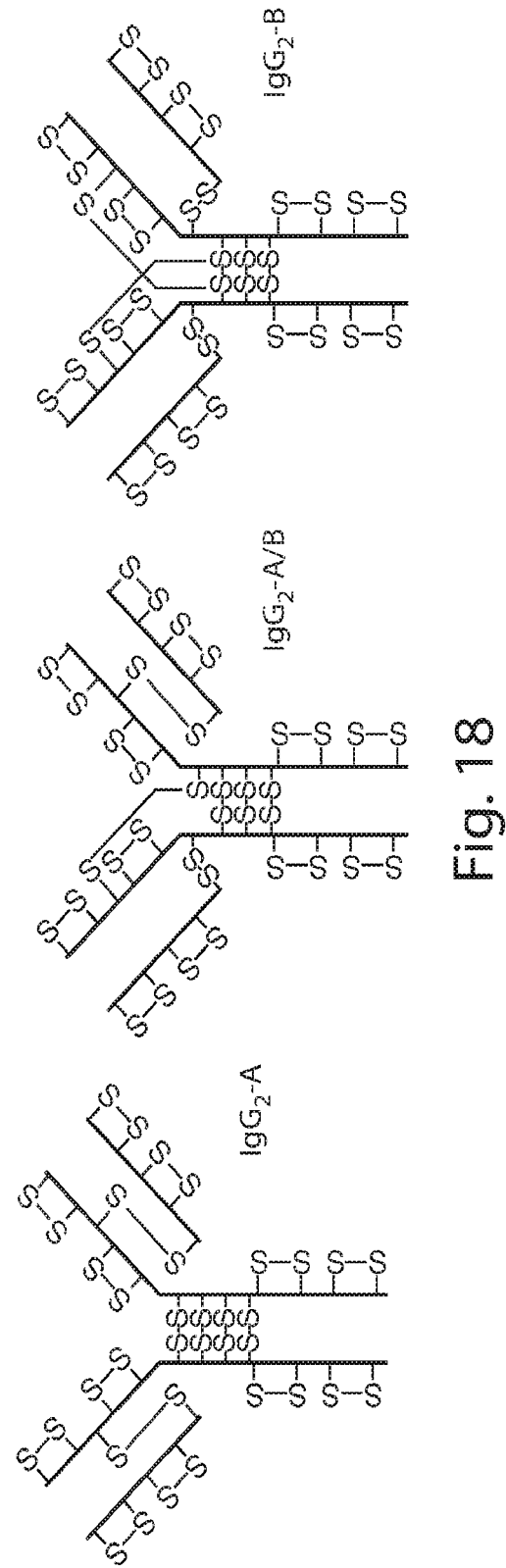
FIG. 18 shows a schematic diagram of the three different structural isoforms of IgG2 antibodies due to disulfide shuffling.

EBI-031 is an IgG2 antibody. As discussed previously, IgG2 antibodies exist in three different structural isoforms, IgG2-A, IgG2-B, and IgG2-A/B isoforms (FIG. 18). In this example, experiments were performed to identify the structural isoforms in EBI-031 samples.

RP-HPLC Analysis

Reversed-phase high-performance liquid chromatograph (RP-HPLC) was used to resolve the various structural isoforms of EBI-031. An enhanced analytical RP-HPLC method that has been used previously for resolving IgG2 disulfide-mediated structural isoforms (see, Dillon et al., *Journal of Chromatography A*, 2006, 1120:112-120) was optimized for resolving EBI-031.

EBI-031 samples containing approximately 30 µg was loaded onto a Zorbax 300SB-C8 column (150 mm×2.1 mm, 5.0 µm, 300 Å). The column temperature was set at 75° C. Mobile phase A was water containing 0.1% TFA, and mobile phase B was 55% IPA, 40% ACN, 4.9% water and 0.1% TFA. The flow rate was 0.5 mL/min. The column was initially equilibrated with 90% mobile phase A and 10% mobile phase B for 2 min followed by a 2 min step gradient from 10 to 25% B. Elution was achieved with a linear gradient of 25-32% B over 21 min. UV absorbance was monitored at 214 nm and/or 280 nm.

Figure 19:
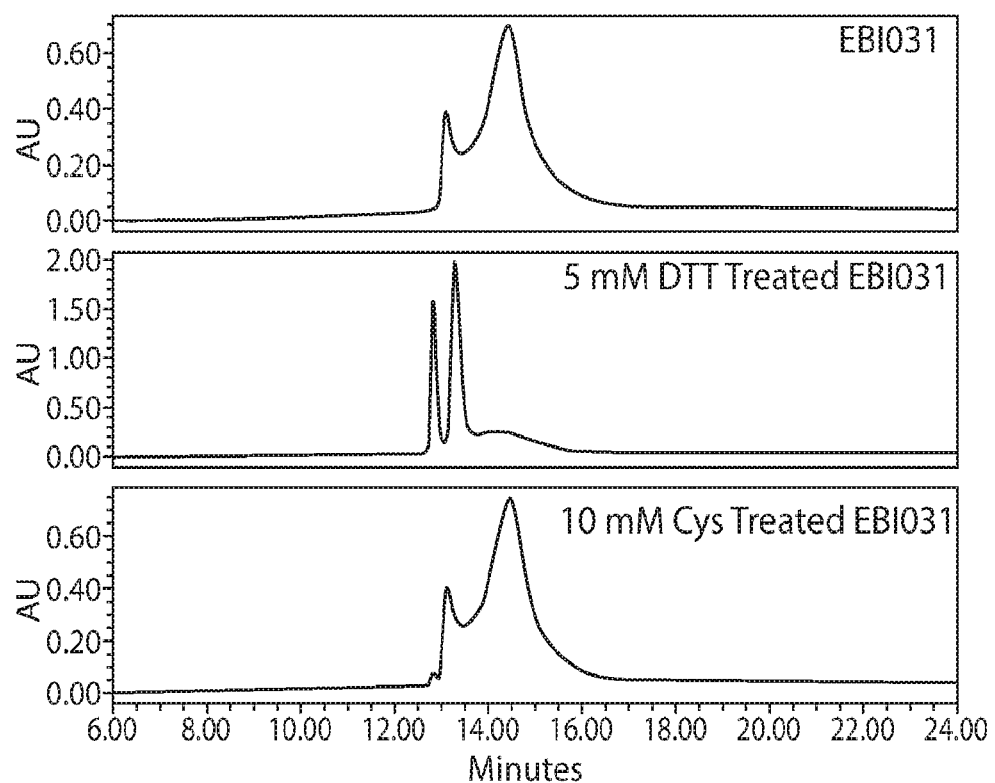
FIG. 19 shows RP-HPLC chromatograms of EBI-031 samples: untreated (top panel), 5 mM DTT (middle panel), 10 mM cysteine (bottom panel).

In order to determine whether the resolution was disulfide-related, the samples were treated with 5 mM DTT and 10 mM cysteine at room temperature for 2 min and then analyzed on the RP-HPLC method (FIG. 19). Treatment with DTT, which is a potent reducing agent, causes reduction of the IgG2 antibody, resulting in elution into early peaks (Peak 0 and Peak 1) (FIG. 19, middle panel). Treatment with cysteine, which is a milder reducing agent compared to DTT, shifts the isoform distribution towards the early peaks (Peak 0 and Peak 1) as well, though not to the extent seen with the DTT-treated sample (FIG. 19, bottom panel).

The data demonstrates that the RP-HPLC method resolved the structural isoforms with different disulfide connectivity. The different disulfide bonding structures were confirmed by non-reduced peptide mapping and mass spectrometry analysis: the early eluting peak (Peak 1) contains the IgG2-AB isoform and the late eluting peak (Peak 2) contains the IgG2-A isoform. Importantly, there was no IgG2-B isoform B (Peak 0) detected in the EBI-031 sample (FIG. 19, top panel).

Comparison of Different EBI-031 Samples

Using the RP-HPLC analysis described above, EBI-031 samples collected from different EBI-031-expressing cell lines were analyzed to compare the isoform distribution of the antibodies produced. EBI-031 samples were collected from a 200 L scale culture of a clonal cell line, a 10 L scale culture from a parental cell line, and a stably transfected pool of cells. EBI-031 was purified using a three-step chromatography method from the clonal and parental EBI-031 expressing cell lines. EBI-031 was purified from the stably transfected pool of cells using Protein A purification. The samples were analyzed by the methods described above.

Figure 20:
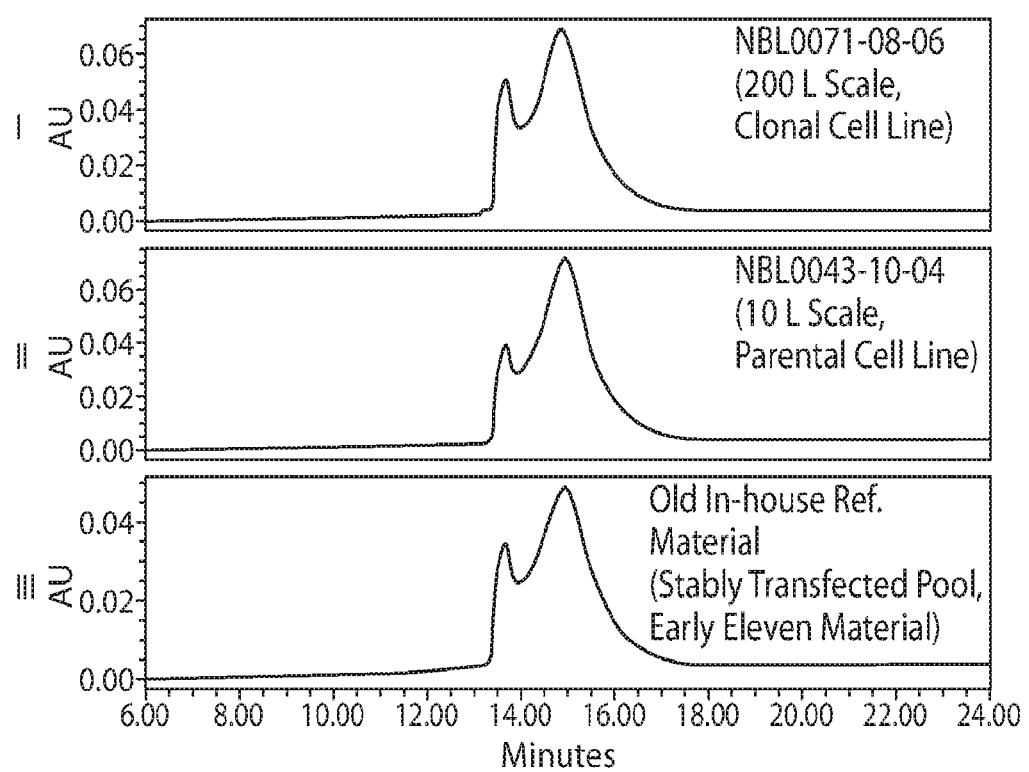
FIG. 20 shows RP-HPLC chromatograms of EBI-031 samples collected from different EBI-031 cell lines: a 200 L scale culture of a clonal cell line (top panel), a 10 L scale culture from a parental cell line (middle panel), and a stably transfected pool of cells (bottom panel).
Figure 21:
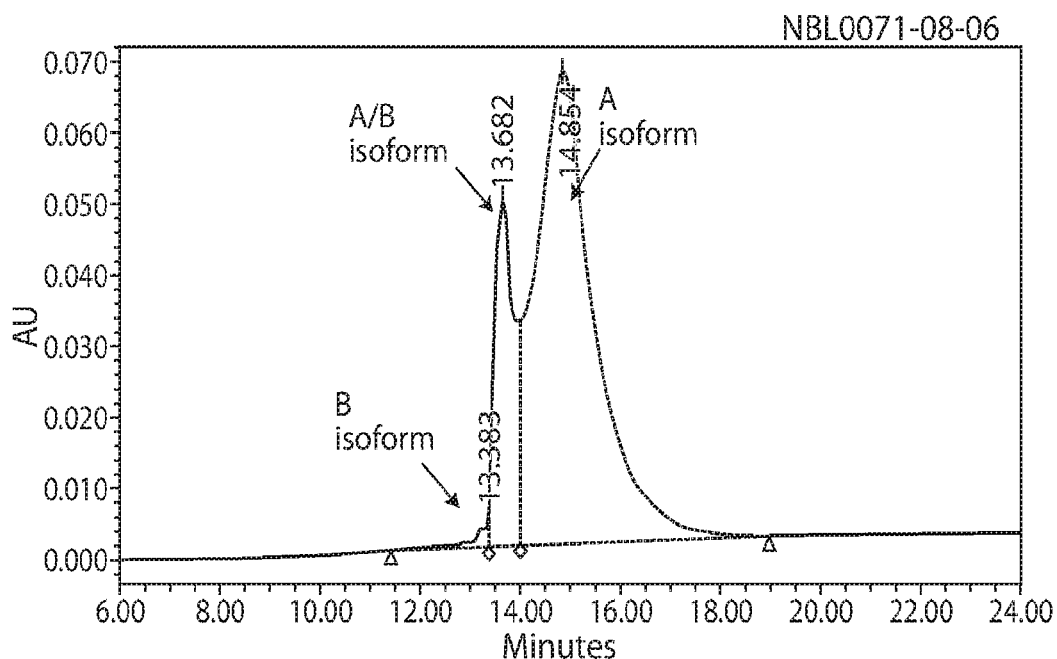
FIG. 21 shows the RP-HPLC chromatogram of EBI-031 collected from a 200 L scale culture of a clonal cell line, and designates and quantifies which isoforms are represented by each peak in the chromatogram.

The results shown in FIG. 20 show that all three EBI-031 samples contained isoforms IgG2-A and IgG2-A/B, but no substantial amount of IgG2-B. This data demonstrates that the EBI-031 IgG2 antibody is produced in a less heterogeneous mixture than other IgG2 antibodies, whether the production is from a clonal EBI-031-expressing cell line, a parental EBI-031-expressing cell line, or from a heterogeneous cell population that stably expresses EBI-031. FIG. 21 shows the distribution of the isoforms from the EBI-031 sample from the 200 L scale culture of a clonal EBI-031-expressing cell line, e.g., the top panel of FIG. 20. The areas under the curves were also measured, and the distributions among the isoforms are shown in the table below the figure.

Example 26: Pharmacokinetics in Primate Studies

The pharmacokinetics of EBI-031 was investigated in primate studies. Two male African green monkeys were tested. 50 g 1 of 50 mg/mL of EBI-031 was intravitreally injected into the eye. Madonna software was used for curve fitting.

The data from the primate study was modeled using a curve fit. Differential equations describing the changes in antibody in the vitreous (A) and antibody outside of the vitreous, e.g., systemic, (Ap) were defined as follows:

$d/dt(A)=-A*kae$ $d/dt(Ap)=A*kae(Dil)-Ap*kape$

The starting parameter values and rates are defined as shown in the table below:

TABLE 8

Starting parameter values and rates

| Parameter | Value |
|---|---|
| Dil - Dilution | 100 |
| kae - Rate of vitreal elimination | 0.2 |
| kape - Rate of systemic elimination | 1.4 |
| Init A - Initial Antibody in vitreous | 1000000 |
| Init Ap - Initial Antibody outside of vitreous | 0 |

Figure 22A:
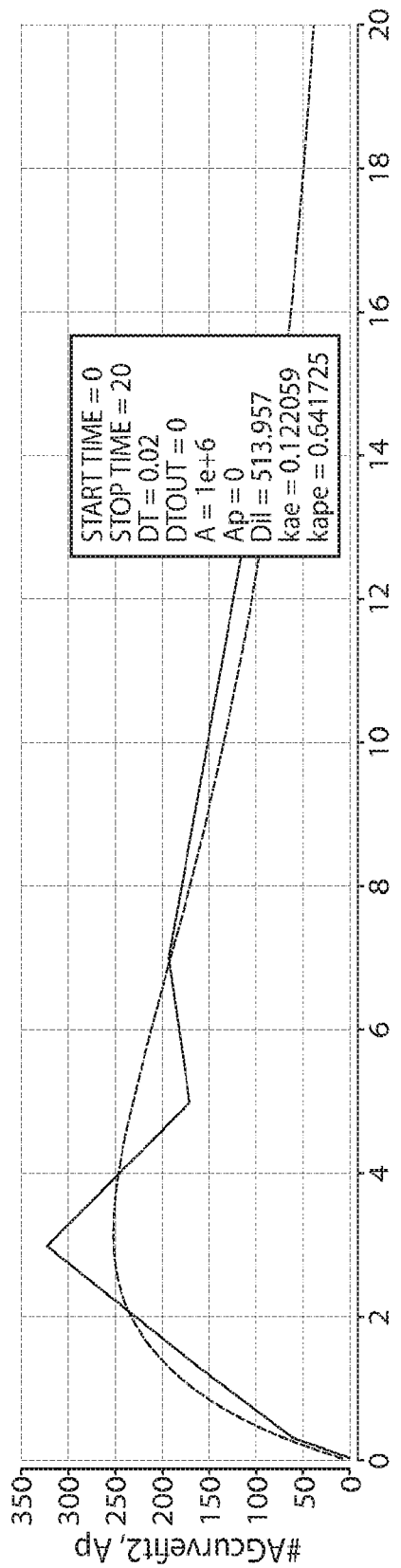
FIG. 22A is a graph showing the pharmacokinetic data from an African green monkey (K797), as described in Example 26.
Figure 22B:
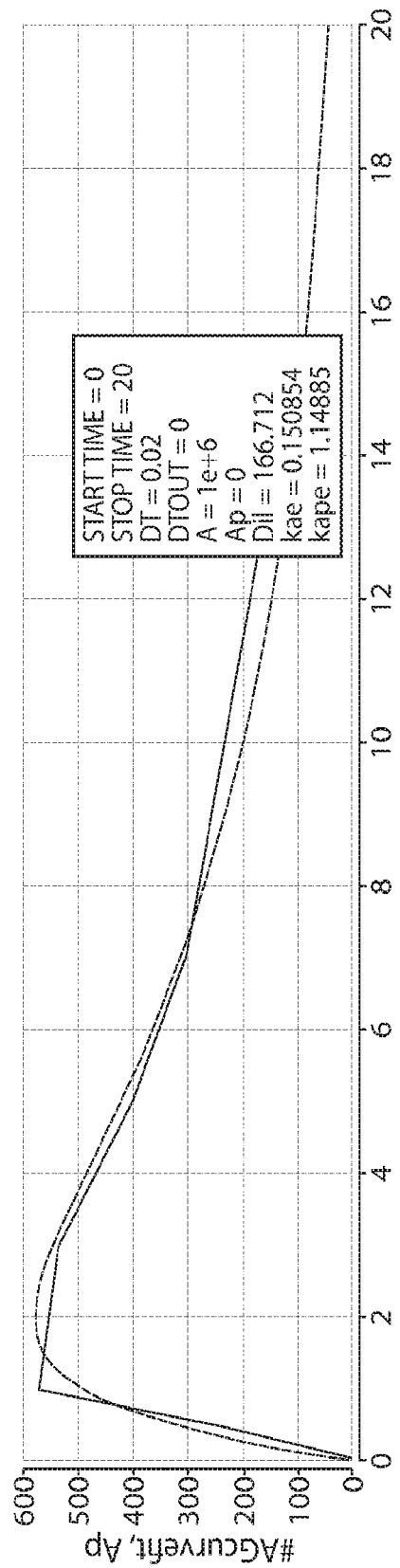
FIG. 22B is a graph showing the pharmacokinetic data from an African green monkey (K679), as described in Example 26.
Figure 23:
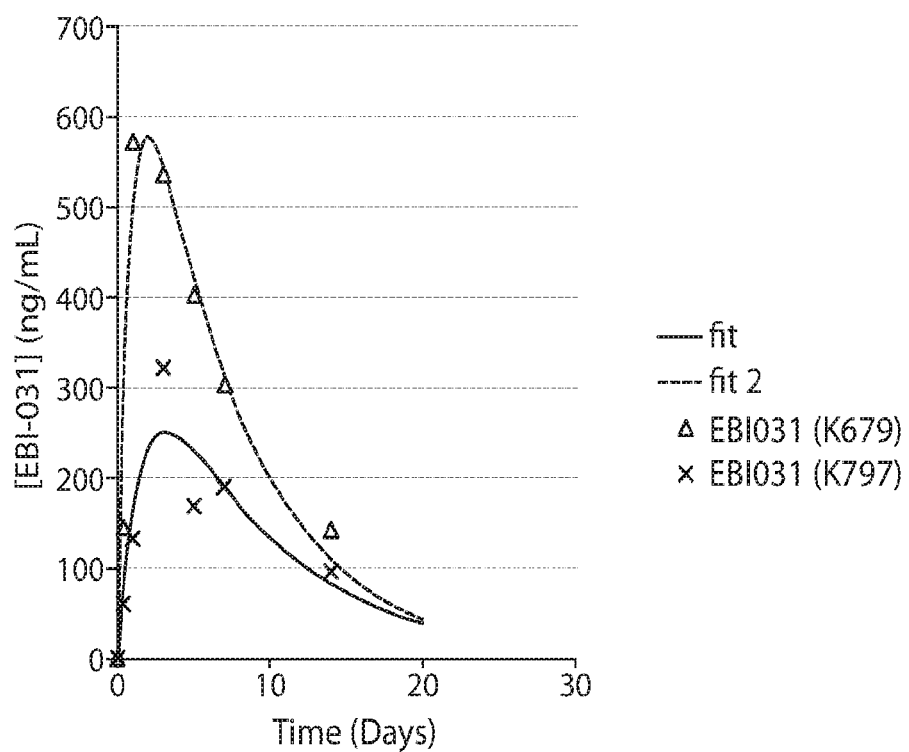
FIG. 23 is a graph showing the pharmacokinetic data from both African green monkeys (K797 or K679) and fit curves.

Other considerations included for fit include: dilution and both rate constant were floated for fit. Initial A was held constant (2×50 ml of 50 mg/mL in 5 mL eye). The results of the modelling as shown in FIGS. 22A, 22B, and 23 showed that vitreal elimination rate constants resulted in half lives of 4.6 and 5.7 days, respectively for the two monkeys. The average vitreal elimination rate constant was calculated to be 5.2 days. Systemic elimination was modeled as 1.1 days, and 0.63 days (average 0.85 days). These results demonstrate that the half-life of EBI-031 in the vitreous was significantly longer than the systemic half-life in primates.

Example 27: Pharmacokinetics of EBI-031

Another pharmacokinetic (PK) experiment was performed, where 50 µl of a 20 mg/mL solution of EBI-031 was injected intravitreally into the eyes of rabbits. Time points examined were 1, 3, 7 and 14 days (e.g., 24, 72, 168, and 336 hours). Two animals (four eyes) were analyzed for each time point. The methods for administering the EBI-031 formulation, harvesting the ocular tissue, and determining protein concentration were performed as described in Example 21.

Figure 24A:
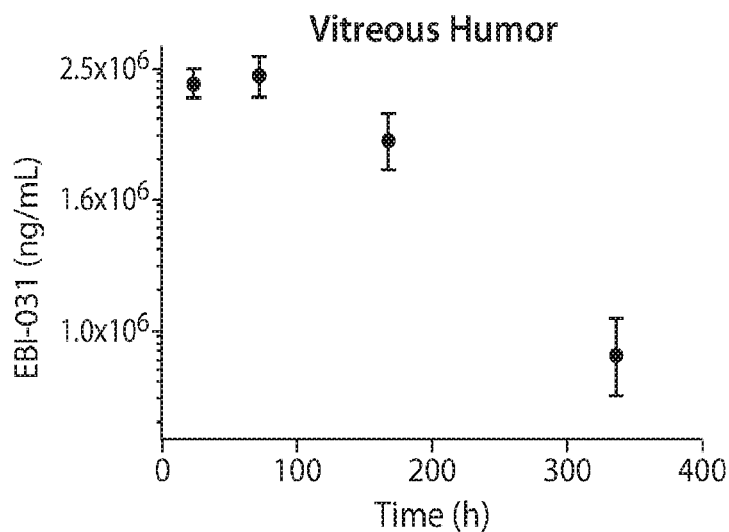
FIG. 24A shows the drug concentration of EBI-031 in the vitreous humor over time following intravitreal administration.
Figure 24B:
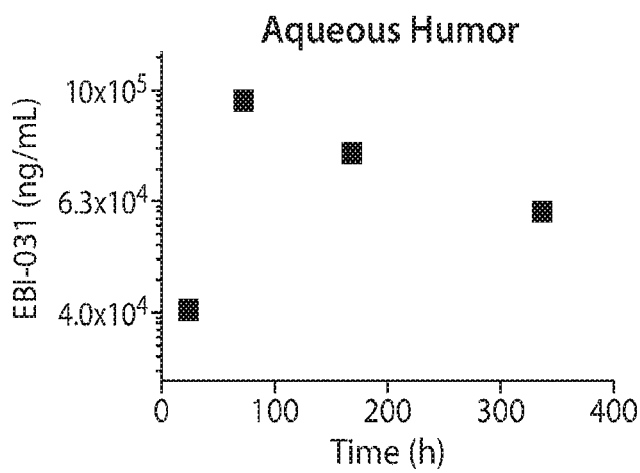
FIG. 24B shows the drug concentration of EBI-031 in the aqueous humor over time following intravitreal administration.
Figure 24C:
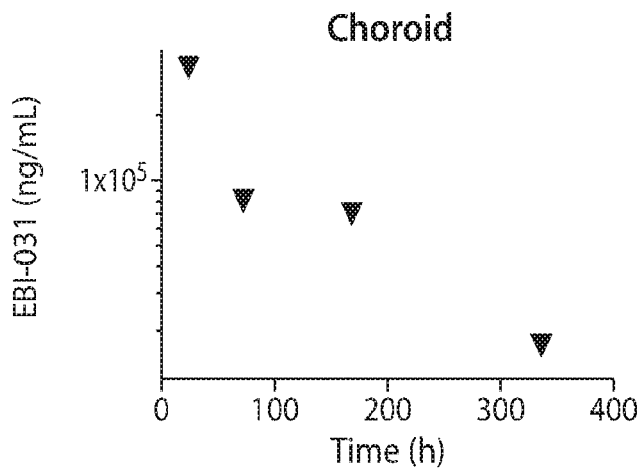
FIG. 24C shows the drug concentration of EBI-031 in the choroid over time following intravitreal administration.
Figure 24D:
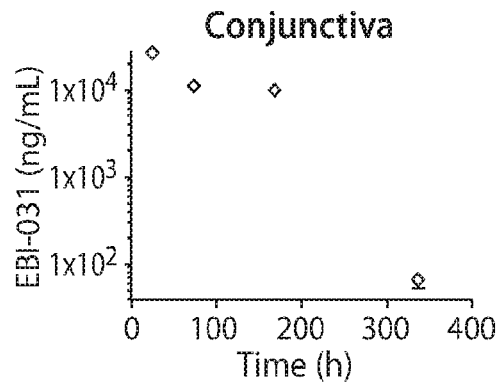
FIG. 24D shows the drug concentration of EBI-031 in the conjunctiva over time following intravitreal administration.
Figure 24E:
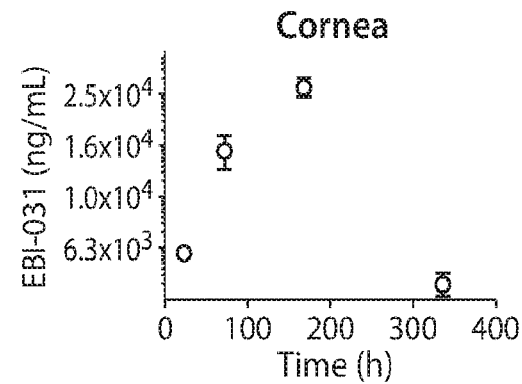
FIG. 24E shows the drug concentration of EBI-031 in the cornea over time following intravitreal administration.
Figure 24F:
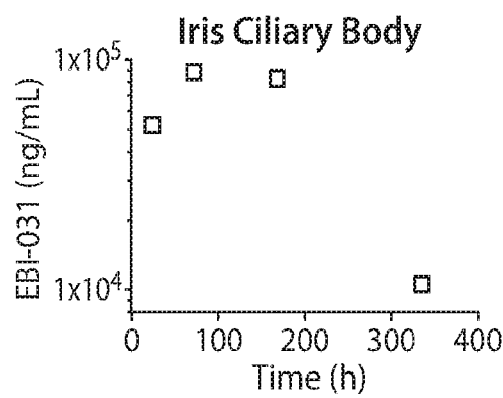
FIG. 24F shows the drug concentration of EBI-031 in the iris ciliary body over time following intravitreal administration.
Figure 24G:
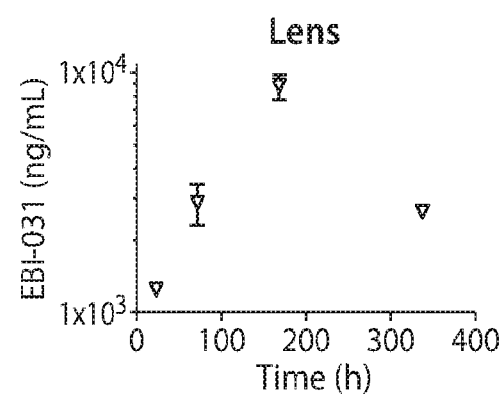
FIG. 24G shows the drug concentration of EBI-031 in the lens over time following intravitreal administration.
Figure 24H:
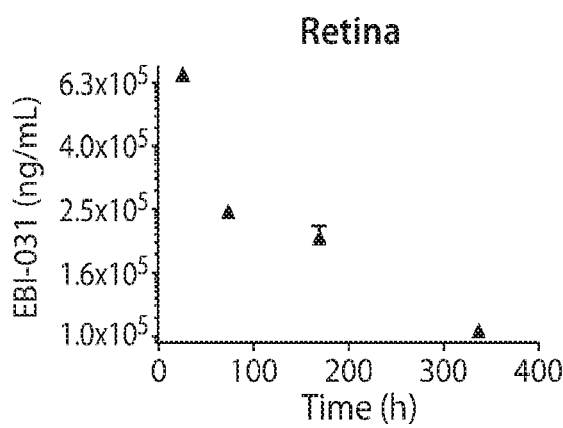
FIG. 24H shows the drug concentration of EBI-031 in the retina over time following intravitreal administration.

The results are shown in FIGS. 24A-24I. When analyzing the protein concentration for days 1-14 in the vitreous humor, the EBI-031 half-life was determined to be 8.95 days (FIG. 24A). However, a strong antibody response was detected on Day 14, which can affect these results. When the protein concentration for days 1-7 in the vitreous humor was analyzed, EBI-031 half-life was determined to be 18.88 days.

Figure 24I:
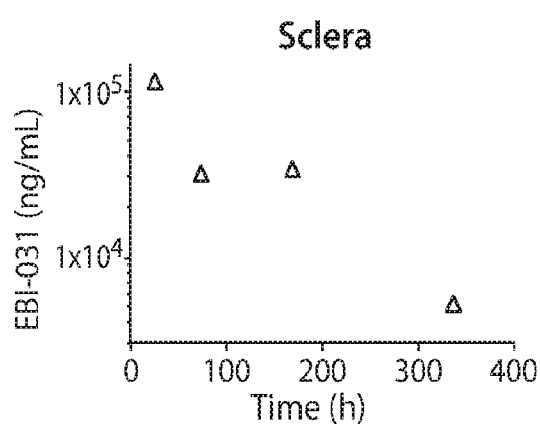
FIG. 24I shows the drug concentration of EBI-031 in the sclera over time following intravitreal administration.

EBI-031 was also detected in other compartments of the eye after intravitreal injection. EBI-031 had also permeated to the aqueous humor (FIG. 24B), the choroid (FIG. 24C), the conjunctiva (FIG. 24D), the cornea (FIG. 24E), the ciliary body (FIG. 24F), the lens (FIG. 24G), the retina (FIG. 24H), and the sclera (FIG. 24I). The drug concentration in these tissues were one to two orders of magnitude lower than the concentrations detected in the vitreous.

Other embodiments are within the scope of the following claims.

What is claimed is:

1. An isolated anti-IL-6 antibody or antigen binding fragment thereof comprising:
   a) a heavy chain variable (VH) domain comprising a VH CDR1 comprising the sequence of SEQ ID NO:31, a VH CDR2 comprising the sequence of SEQ ID NO:32, and a VH CDR3 comprising the sequence of SEQ ID NO:33, and
   b) a light chain variable (VL) domain comprising a VL CDR1 comprising the sequence of SEQ ID NO:34, a VL CDR2 comprising the sequence of SEQ ID NO:35, and a VL CDR3 comprising the sequence of SEQ ID NO:36.

2. The isolated antibody or antigen binding fragment of claim 1, wherein the VH domain comprises an amino acid sequence that is at least 90% identical to SEQ ID NO:37.

3. The isolated antibody or antigen binding fragment of claim 1, comprising an amino acid sequence that is at least 90% identical to SEQ ID NO:39, SEQ ID NO:41, or SEQ ID NO:54.

4. The isolated antibody or antigen binding fragment of claim 1, wherein the VL domain comprises an amino acid sequence that is at least 90% identical to SEQ ID NO:38.

5. The isolated antibody or antigen binding fragment of claim 1, comprising a light chain comprising an amino acid sequence that is at least 90% identical to SEQ ID NO: 42.

6. The isolated antibody or antigen binding fragment of claim 1, wherein the VH domain comprises SEQ ID NO:37 and the VL domain comprises SEQ ID NO:38.

7. The isolated antibody or antigen binding fragment of claim 1, comprising a heavy chain comprising SEQ ID NO:41 and a light chain comprising SEQ ID NO:42.

8. The isolated antibody or antigen binding fragment of claim 1, comprising (a) a heavy chain comprising amino acids 1-225 of SEQ ID NO:39 or comprising SEQ ID NO:54 and (b) a light chain comprising SEQ ID NO:42.

9. An isolated antibody or antigen binding fragment of claim 1, further comprising a heavy chain comprising the VH domain, wherein the heavy chain comprises SEQ ID NO:47.

10. An isolated antibody or antigen binding fragment of claim 1, further comprising a heavy chain comprising the VH CDR1, the VH CDR2 and the VH CDR3, wherein the heavy chain comprises SEQ ID NO:41 comprising 0, 1, 2 3 or 4 mutations at positions selected from I254, H311, I254, and H346.

11. The isolated antibody or antigen binding fragment of claim 10, wherein the mutation at position I254 are selected from I254 Å and I254R.

12. The isolated antibody or antigen binding fragment of claim 10, wherein the mutation at position H311 are selected from H311A, H331E and H311N.

13. The isolated antibody or antigen binding fragment of claim 10, wherein the mutation at position D313 is D313T.

14. The isolated antibody or antigen binding fragment of claim 10, wherein the mutation at position H436 is H436A.

15. The isolated antibody or antigen binding fragment of claim 1, further comprising a light chain comprising the VL domain, wherein the light chain comprises SEQ ID NO:42.

16. An isolated anti-IL-6 antibody or antigen binding fragment comprising a heavy chain sequence comprising SEQ ID NO: 47 and a light chain sequence comprising SEQ ID NO:42.

17. The isolated antibody or antigen binding fragment of claim 1, wherein the antibody is an IgG2 antibody.

18. The antibody or antigen binding fragment of claim 17, wherein the antibody or antigen binding fragment is an IgG2-A isoform or an IgG2-A/B isoform, but not an IgG2-B isoform.

19. A pharmaceutical composition comprising the antibody or antigen binding fragment of claim 1 and a pharmaceutically acceptable carrier.

20. A method of treating an IL-6 associated disease, the method comprising administering to a subject a therapeutically effective amount of the antibody or antigen binding fragment of claim 1, wherein the IL-6 associated disease is an ocular disease characterized by an elevated level of IL-6 in the vitreous.

21. The method of claim 20, wherein the IL-6 associated disease is diabetic macular edema (DME), diabetic retinopathy, uveitis, dry eye (e.g., dry eye disease or dry eye syndrome), age-related macular degeneration (AMD), proliferative diabetic retinopathy (PDR), retinal vein occlusion (RVO), neuromyelitis optica (NMO), corneal transplant, corneal abrasion, or physical injury to the eye.

22. The method of claim 21, wherein the antibody or antigen binding fragment is delivered to the vitreous of the subject's eye.

23. The method of claim 22, wherein the IL-6 associated disease is diabetic macular edema.

24. The isolated antibody or antigen binding fragment of claim 1, wherein the VL domain comprises amino acids 1-111 of SEQ ID NO:38.

25. The isolated antibody or antigen binding fragment of claim 1, wherein the VH domain comprises SEQ ID NO:37 and the VL domain comprises amino acids 1-111 of SEQ ID NO:38.

26. A pharmaceutical composition comprising the antibody or antigen binding fragment of claim 25 and a pharmaceutically acceptable carrier.

27. A method of treating an IL-6 associated disease, the method comprising administering to a subject a therapeutically effective amount of the antibody or antigen binding fragment of claim 26, wherein the IL-6 associated disease is an ocular disease characterized by an elevated level of IL-6 in the vitreous.

28. The method of claim 27, wherein the IL-6 associated disease is diabetic macular edema (DME), diabetic retinopathy, uveitis, dry eye (e.g., dry eye disease or dry eye syndrome), age-related macular degeneration (AMD), proliferative diabetic retinopathy (PDR), retinal vein occlusion (RVO), neuromyelitis optica (NMO), corneal transplant, corneal abrasion, or physical injury to the eye.

29. The method of claim 28, wherein the antibody or antigen binding fragment is delivered to the vitreous of the subject's eye.

30. The method of claim 29, wherein the IL-6 associated disease is diabetic macular edema.

31. A pharmaceutical composition comprising the antibody or antigen binding fragment of claim 16 and a pharmaceutically acceptable carrier.

32. A method of treating an IL-6 associated disease, the method comprising administering to a subject a therapeutically effective amount of the antibody or antigen binding fragment of claim 31, wherein the IL-6 associated disease is an ocular disease characterized by an elevated level of IL-6 in the vitreous.

33. The method of claim 32, wherein the IL-6 associated disease is diabetic macular edema (DME), diabetic retinopathy, uveitis, dry eye (e.g., dry eye disease or dry eye syndrome), age-related macular degeneration (AMD), proliferative diabetic retinopathy (PDR), retinal vein occlusion (RVO), neuromyelitis optica (NMO), corneal transplant, corneal abrasion, or physical injury to the eye.

34. The method of claim 33, wherein the antibody or antigen binding fragment is delivered to the vitreous of the subject's eye.

35. The method of claim 34, wherein the IL-6 associated disease is diabetic macular edema.

* * * * *

UNITED STATES PATENT AND TRADEMARK OFFICE
CERTIFICATE OF CORRECTION

PATENT NO. : 11,142,571 B2
APPLICATION NO. : 15/524727
DATED : October 12, 2021
INVENTOR(S) : Michael March Schmidt et al.

It is certified that error appears in the above-identified patent and that said Letters Patent is hereby corrected as shown below:

In the Claims

Claim 12, Column 135, Line 3, please replace "H331E" with --H311E--

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*